United States Patent
Piel

(10) Patent No.: US 7,771,972 B2
(45) Date of Patent: Aug. 10, 2010

(54) GENE CLUSTER OF PEDERIN BIOSYNTHESIS GENES

(75) Inventor: Jörn Piel, Jena (DE)

(73) Assignee: Rheinische Friedrich-Wilhelms-Universitaet Bonn, Bonn (DE)

( * ) Notice: Subject to any disclaimer, the term of this patent is extended or adjusted under 35 U.S.C. 154(b) by 1528 days.

(21) Appl. No.: 10/496,377

(22) PCT Filed: Nov. 21, 2002

(86) PCT No.: PCT/EP02/13085

§ 371 (c)(1),
(2), (4) Date: May 24, 2004

(87) PCT Pub. No.: WO03/044186

PCT Pub. Date: May 30, 2003

(65) Prior Publication Data

US 2005/0118590 A1    Jun. 2, 2005

(30) Foreign Application Priority Data

Nov. 22, 2001  (EP)  .................................. 01127395

(51) Int. Cl.
*C12P 1/00* (2006.01)
*C12P 21/04* (2006.01)
*C12P 21/06* (2006.01)
*C12P 19/34* (2006.01)
*A01N 43/04* (2006.01)

(52) U.S. Cl. ........................ 435/91.1; 435/41; 435/69.1; 435/71.1; 435/71.3; 530/388.21; 536/24.5

(58) Field of Classification Search ........................ None
See application file for complete search history.

(56) References Cited

OTHER PUBLICATIONS

Albertini et al., (Accession No. AAA85144, submitted Jun. 20, 1994).*
Kellner et al., (J. of Heredity. 2000: 91(2): pp. 158-162).*
Du et al. (Chem. Biol. Aug. 2000; 7(8): 623-642).*
Kellner et al., (Entomologia Experimentalis et Applicata. 1999. vol. 93, pp. 41-49).*
Kellner, Rupert LL: "Suppression of pederin biosynthesis through antibiotic elimination of endosymbionts in *Paederus sabaeus*", Journal of Insect Physiology, vol. 47, No. 4-5, Apr. 2001, pp. 475-483, ISSN: 0022-1910.
Cardani C. et al., "The Biosynthesis of Pederin", Tetrahedron Letters, vol. 30, 1973, pp. 2815-2818, ISSN: 0040-4039.
Beyer S. et al., "Metabolic diversity in myxobacteria: identification of the myxalamid and the stigmatellin biosynthetic gene cluster of Stigmatella aurantiaca Sg a15 and a combined polyketide-(poly)peptide gene cluster from the epothilone producing strain *Sorangium cellulosum* So ce90", Biochimica ET Biophysica Acta. Gene Structure and Expression, Elsevier, Amsterdam NL, vol. 1445, No. 2, May 14, 1999, pp. 185-195, ISSN: 0167-4781.
Database EMBL 'Online!, "*Pseudomonas fluorescens* NCIMB 10586 mupirocin biosynthetic gene cluster", Apr. 2, 2001, Database accession No. AF318063.
Narquizian R. et al., "The pederin family of antitumor agents: structures, synthesis and biological activity", Ernst Schering Research Foundation Workshop, Germany 2000, No. 32, 2000, pp. 25-56, ISSN: 0947-6075.
Rodriguez Eduardo et al., "Combinatorial biosynthesis of antimicrobials and other natural products", Current Opinion in Microbiology, vol. 4, No. 5, Oct. 2001, pp. 526-534, ISSN: 1369-5274.
Cane David E. et al., "The parallel and convergent universes of polyketide synthases and nonribosomal peptide synthetases", Chemistry & Biology (London), vol. 6, No. 12, Dec. 1999, pp. R319-R325, ISSN: 1074-5521.
Piel Joern, "A polyketide synthase-peptide synthetase gene cluster from an uncultured bacterial symbiont of Paederus beetles", Proceedings of the National Academy of Science of the United States, vol. 99, No. 22, Oct. 29, 2002, pp. 14002-14007, ISSN: 0027-8424.

* cited by examiner

*Primary Examiner*—Robert B Mondesi
*Assistant Examiner*—J. Hines
(74) *Attorney, Agent, or Firm*—Crowell & Moring LLP

(57) ABSTRACT

The present invention relates to the cloning, sequencing and analysing of a gene cluster encoding a modular polyketide synthase enzyme involved in the biosynthesis of the antitumor compound pederin. This novel cluster represents the first example of genes from an unculturable symbiont encoding the biosynthesis of a drug candidate.

10 Claims, 4 Drawing Sheets

Pederin, from *Paederus* beetles

Figure 1:
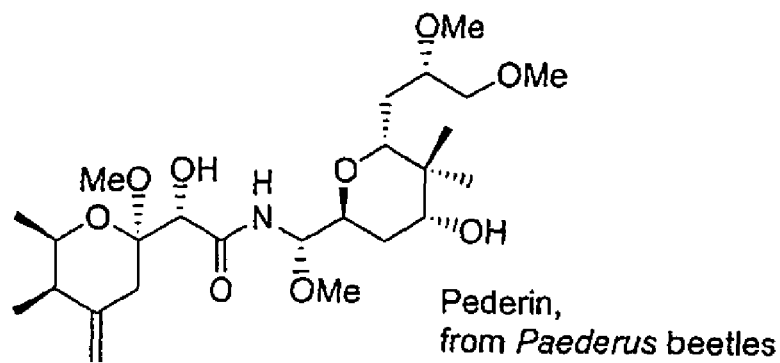
Figure 1:
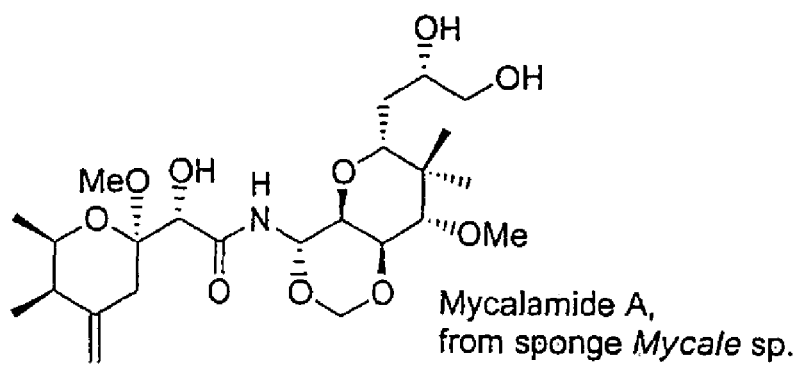
Figure 1:
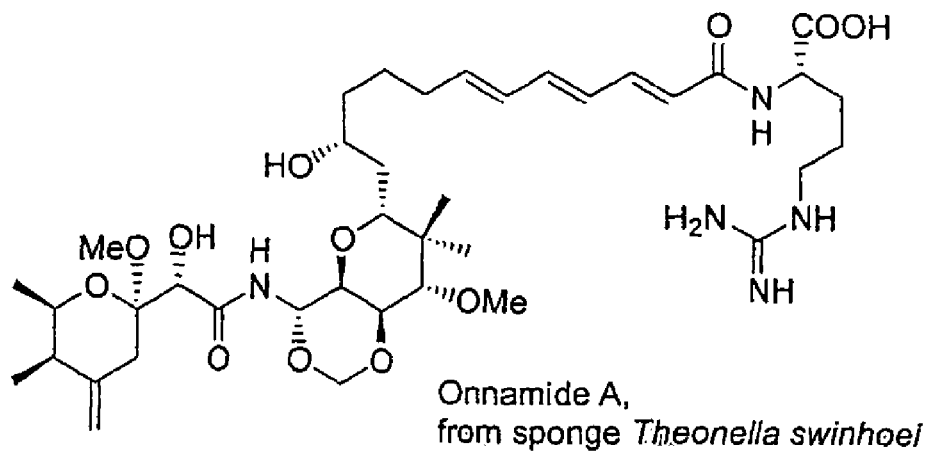

Mycalamide A, from sponge *Mycale* sp.

Onnamide A, from sponge *Theonella swinhoei*

SEQUENCE LISTING

```
<160> NUMBER OF SEQ ID NOS: 26

<210> SEQ ID NO 1
<211> LENGTH: 52659
<212> TYPE: DNA
<213> ORGANISM: Unknown
<220> FEATURE:
<223> OTHER INFORMATION: Bacterial Symbiont of Paederus fuscipes
<220> FEATURE:
<221> NAME/KEY: misc_feature
<223> OTHER INFORMATION: Sequence of the pederin biosynthetic gene
      cluster. Differences in the sequence are dependent on whether the
      DNA was sequenced from the cosmid or the genome.
<220> FEATURE:
<221> NAME/KEY: gene
<222> LOCATION: (274)..(1212)
<223> OTHER INFORMATION: PedA putative methyltransferase
<220> FEATURE:
<221> NAME/KEY: gene
<222> LOCATION: (1226)..(2620)
<223> OTHER INFORMATION: PedB putative FMN-dependent oxidoreductase
<220> FEATURE:
<221> NAME/KEY: gene
<222> LOCATION: (2796)..(3800)
```

<223> OTHER INFORMATION: PedC putative acyltransferase
<220> FEATURE:
<221> NAME/KEY: gene
<222> LOCATION: (3919)..(5013)
<223> OTHER INFORMATION: PedD putative acyltransferase
<220> FEATURE:
<221> NAME/KEY: gene
<222> LOCATION: (5243)..(6064)
<223> OTHER INFORMATION: PedE putative methyltransferase
<220> FEATURE:
<221> NAME/KEY: gene
<222> LOCATION: (6309)..(32114)
<223> OTHER INFORMATION: PedF mixed type I polyketide
      synthase/nonribosomal peptide synthase
<220> FEATURE:
<221> NAME/KEY: misc_feature
<222> LOCATION: (6309)..(8489)
<223> OTHER INFORMATION: module 1 PKS
<220> FEATURE:
<221> NAME/KEY: misc_feature
<222> LOCATION: (8586)..(11618)
<223> OTHER INFORMATION: module 2 NRPS
<220> FEATURE:
<221> NAME/KEY: misc_feature
<222> LOCATION: (11817)..(15236)
<223> OTHER INFORMATION: module 3 PKS
<220> FEATURE:
<221> NAME/KEY: misc_feature
<222> LOCATION: (15381)..(20192)
<223> OTHER INFORMATION: module 4 PKS
<220> FEATURE:
<221> NAME/KEY: misc_feature
<222> LOCATION: (20334)..(25508)
<223> OTHER INFORMATION: module 5 PKS
<220> FEATURE:
<221> NAME/KEY: misc_feature
<222> LOCATION: (25686)..(29315)
<223> OTHER INFORMATION: module 6 PKS
<220> FEATURE:
<221> NAME/KEY: misc_feature
<222> LOCATION: (29478)..(32114)
<223> OTHER INFORMATION: module 7 incomplete PKS
<220> FEATURE:
<221> NAME/KEY: gene
<222> LOCATION: (32142)..(33443)
<223> OTHER INFORMATION: PedG putative flavin-binding monooxygenase
<220> FEATURE:
<221> NAME/KEY: gene
<222> LOCATION: (33467)..(52267)
<223> OTHER INFORMATION: PedH mixed type I polyketide
      synthase/nonribosomal peptide synthetase
<220> FEATURE:
<221> NAME/KEY: misc_feature
<222> LOCATION: (33467)..(33863)
<223> OTHER INFORMATION: module 1 incomplete PKS
<220> FEATURE:
<221> NAME/KEY: misc_feature
<222> LOCATION: (34070)..(38558)
<223> OTHER INFORMATION: module 2 PKS
<220> FEATURE:
<221> NAME/KEY: misc_feature
<222> LOCATION: (38678)..(42209)
<223> OTHER INFORMATION: module 3 PKS
<220> FEATURE:
<221> NAME/KEY: misc_feature
<222> LOCATION: (42314)..(45836)
<223> OTHER INFORMATION: module 4 PKS
<220> FEATURE:
<221> NAME/KEY: misc_feature
<222> LOCATION: (45944)..(48128)
<223> OTHER INFORMATION: module 5 PKS
<220> FEATURE:
<221> NAME/KEY: misc_feature
<222> LOCATION: (48336)..(52267)
<223> OTHER INFORMATION: module 6 NRPS

<400> SEQUENCE: 1
gatctatgag gccatctgta tcccatcgat tgtaagtcgt gggcgagctg gctttgccac    60

```
agacgaccca tacctccacc tgggtgggat acgctgaagc aagtcagtgc aggtgattta    120
cgaggaaagc agctaagcta agaacctgtt tacgagtcga agttgtgtcc gataagggtt    180
tcgaaatatt tttcagcaca ggtggactgc actttcccgg cagttctcac ctgattttcc    240
cagctcgcga gatcgtgaac aggttcggta tggctacttt tgcgcgcaga tgaaaaggca    300
gtgcttggtg atcgagttca actggtagta agaccagagc atctcggtca gctgaacgat    360
atcgagttca cccttataaa aggcttcatg cacgcgcttg accgcgtaga tgaagtgtgc    420
tccccatact tcgtcactga catcctctat ctcgacctgg ctgaagcctg tgtccttgag    480
taaccgccgg tattcttccg tatcattcag atggttgatt gcgctcggga aaatcgggta    540
ctgctccagt ctttcggaag agctgaacag gacatccgat agtactagac gaccgcccgg    600
cctgagaatc cgacgcgctt cttcgagaaa tttctggcgt gtttcgaagt ggaaggcggc    660
ttcgatgcat aggatgttgt cgaagaatcc ctcttcgaag gaaagatcaa ccgcgttcat    720
cacctgcgca tggcaaccgg ggacatttcg gcgagtcgct tcgatctgtt tttccgagat    780
attgatggcc cagatattat ctgctgggta atactcgagc aggtgtcgtg tggatgcccc    840
catgccgcaa gcggcgtcca gtatgcgtcc tgattttttcc ggaatgaagt cgagcaacgc    900
atcctgcaaa cgttcagaag cctcgtgttg agtcgttgtg gtttcgtccc aatagccgat    960
gttccgatag tccgagccgt cgaccaatag gctggtcaac ccctcgctga aaacgtgtg    1020 gtcgtaatgc tgattgatat ggcttgcgag gcgctctttt tcatcgtttg aattagtgtt    1080
cgacgcctct gatccgtgcg cgtctttcga cggggcagcg ccgaagtcga agattttctg    1140
caggtcgatc ggtacgtaac cgatgccgtc gacatgtgag gaaatgcatt cgaatagccg    1200
ttgcttaagc acttgagtgt cgttctcaag ttgaaactgc tgcatggtca tgtgtaaagc    1260
tcatcctatt agtagtgaga gaggcgatgc gtttattgag atattccgcg caggcatcca    1320
tcagatagtc ggccatctta gtgacatcac ggttttttcca gtcttccaag ggcgtgtctt    1380
taacccatct attgaaggca ccgagcgcag ggccggtatg aatctgatag tcggtccgct    1440
gttcatggtt gccctctagt gcaaggcgca ttgtgtgaac gaagtaccag cgaaaaatca    1500
gtgccatctt gagcttagga tcacgttcgg cttttctcgat atgggcggga gatgccttgc    1560
ggtaatagcg ttcggtttcc tgatagatat catcgaagct gcgcttgaaa tacttatcct    1620
gtagctcctt gcgcacagtc ggagccagct gttccaacga gccgttgtta cgccacaggt    1680
catagagcct gttggccctg accgaaagaa aaacgctctt tttcagaact tgtattttcg    1740
aaccgagttc gaacatatcg ccggccggcg cgtatgccgt gtcctgaaca tcgatgcttt    1800
gcagcatctt tttcaccgtc tcgctggtac cggcttgaac cgtacattga ttgatcgatc    1860
cggtgacgat gaactcggct cccagcatga acgcggaagc ggcggattcg ggggtgccga    1920
taccgccggc ggaacccact ctgactgggc tctgaaagcg gtattgctgc tgcaaggtat    1980
cgcgtaaacg gatgatgcgc ggcagtacca cgctggtaac ggccatgtcc gtgtggcctc    2040
ccgaatcggc ctcgacgcaa acgtctgagg ctactgcgat acgacccgcc agctcggcct    2100
cttgttcatt aatccgacct tcagttagta gtaggctgac tatagatgcg ggcaccggac    2160
taagaaaaag ctgtgcgatt tctgggcgtg aaacttttgc cataagggta ttggctgcct    2220
gcactttacc gctggcatca agatgcagac ccttgagccg aaggtaacc agcgcgggag    2280 ttatctgcat gaaagctgcg gcttcgatgt gccgcacgcc gtaacgcagt aacaggtcga    2340
tcagatgatt ttcttttctcg agatcggcaa ggttagccag cacattgatt ccgtaaggct    2400
```

-continued

```
cgcctcggtt cagcccttgt tggatacgtt gaatggcggt ttcgatttct tccagagtca    2460
tacccccggc tccatagaaa ccgacataac ccgcctttcc catggcaatt accaaatcag    2520
atgacccaat agctttcgcc atagcgccgg ctacatacgc ataccgtact tggtaatctt    2580
ctttgaagag gcgggagccg agttttcag cagttatcat gttggaatct cgacaatatt    2640
tcctttgtct ggaccaaagt gagatagtgt tttacttgat ttctccagtt caatattaag    2700
gttacgctta tttgaattgc tcggaaaaga gagattaatt ggcccttggc tattttgttt    2760
caatctcaaa ggcttcaccc tggggatatc gtcaactaac gttggtcgag ttcgagcaga    2820
cgcaggcgag caatttcgat gttttcaaga tcgcggccga acggtgtcat ggttggtagt    2880
attcgataat ggatcgaaga gggcagattg tatttagtag ccgctgccat gtttccagct    2940
gggccgaggt ctagatatac ggcgttaggg ctggattgat gaaaagtatt gatcgcaagg    3000
tgaaatgcta tcggttgtcg aatgacatgc caccaataag ttgatgagaa cgggttaat     3060 tgctcaggga ccgcaatgc gcaagagatg accgtgtat gcaggcgccg acaaatttgc      3120
tcgggaaatt gctggatgaa tatttcatgc acctcatcca tccaagaaga gtggaatgct    3180
atcgacacgg gcagaagttg acaggcgata ttctgtttag tcaagctttt acgggtttgc    3240
aggattccgg tgcggggggcc ggataccacg aagcagtgat cgaagtttat ccccgcgagt   3300
tcgcaatctt tcgaaaacgc cggggttgtc gagaaggtat caatatgatc gatgacgagt    3360
aacatggctc ctgcgttaca gtattcatcg aaaagtcggg cttgtttgat gaggttgaag    3420
aggatgttct ccacatgggt atcgccggcc agggaaatgg cgatgaattc tcccaagctg    3480
gcgccgatga gaaagtccgg cgcgggaagt ccccgagcta gcaaggattt ggcgagtgcg    3540
tattgaacca taaataaagc ggggtgggta tggatgagtc gatcgaaggg tagacttcgt    3600
tcgtgcccag tgtcatagat tatatccaag agggattgcc ctatgtaatc gcgcacattg    3660
tcgtcgagtg atttcatcca ggcatgaaac gtttcatctt gttcgtatag ctggcgcccc    3720
atttggaagt attgggatcc ttgcccagaa acatccaaa ctaccgggtg agtgttctgt     3780
atattttgca agtctttcat cagtgtatac caggaaaagt tgaggataga aaactgttac    3840 gttttttaaga accgtggtaa agccttttcga aggtgatatc ttatatttta agttctctca  3900
tcgatcaagg aactgtatat gaaatcgtac cttttttcccg ggcagggttc gcaacactta   3960
ggcatgggtg agcaattatt cgatcgcttt cccaatatca tcgaggcggc aaacgatatt    4020
cttggatact ccatcaaaac gctatgtctt gaagatccgc agcgtcaact caggctgact    4080
caatacactc aggtagcctt gtatgttgtt aatgcgctga cttatcgcca gcatttgcag    4140
cagggaggtg gtctccccga tttcgtggca ggtcacagct tgggtgagta taacgccctg    4200
gaaagtgctg gcgtgttcag cttcgaagat ggcctgagac tcgtgcagaa gcgtggtgat    4260
ctgatgagtc aggcgccgag gggagctatg ccgccatct tgggcatcag cgctgacagt     4320
gtcgcgggca tattggccga acagggactg acacggatcg atattgccaa ctataacgct    4380
ccgacccaaa ccattatctc cggcctggaa gcggatattc gggatgccca ggcggttttt    4440
gagtcatgcc aagctatgta cgtgccgctc aataccagtg gcgctttcca ttcacgctac    4500
atgcagtcgg ctcgtgatga gttcgcgcaa tttcttgaag cgtttgagtt ccgcgatccc    4560
caaatacctg tagtggcgaa cgtcaccgcg aagccctatg ttggtactga ggtcgttcgt    4620
acccttgcgg atcagttgac tggttccgtc cgctggctgg acagcatgcg ttttctgctc    4680
gatcaaggag tgacggagtt tcgcgagctt ggtcctggcg atgtgttgag caagttggtg    4740
gaaagtatca gatcgagcgc catgtcgaag ccggtttcgg agtttgcagc tgaaaactct    4800
```

```
cagcagttag tcgatgaatg gaaccgtacc tgtccgatag gttccagggt aagggtaaaa   4860
ggctatgacg atattctggt caccaaaagc cgagctgttc ttctatttgg gcatcgtgcg   4920
gccatctata tggaaaacta tcagggatat ttcgcacttt ccgaggtaga accactcata   4980
gagcagcagc ctttagttga aaaggtgtgg tgacctgatg tcaattggga caagtttaac   5040
tcagttgccc gaaaagggta tggacgatag tgttctcgca aaaccgattt attgatttat   5100
atgtgtggca gtgagtaaaa aaattcaagt cttgaagatg ccctgttata atgtgaata    5160 gcgagtattg ccgggcgctt tggattttt tgaaggatta agttttttat catatcgttt    5220
ctaacctatt ggagaccatg caatgcagac cgctatcgct gatgtcgaga agttgctac    5280 gctttatgat tccgcagaag ggcaagtagg ccctatttta ttcggcggac atatgcattg   5340
gggctattgg gatgaagtca ctggggaggg gaactttgcc aacgcagcag aaaggcttgc   5400
gcagattatg attgctaagg cacctataaa ggccgggcaa aaattcatcg acatgggatg   5460
tggctttgga gagtctgcct tgaagctggc caaagccaag ggttgtttcg ttgatggaat   5520
aaccattagc aaggagcaac agctcagtgc aattactcgg gctgaagcag agcaactgca   5580
agagcgtgtc cgatttattc atggtagcgc actgaatata ccgtgcgaag accaatcgta   5640
tgatggtggt tggttttcg agtccatttt tcatatgggt catagaaaag cccttcatga    5700
ggctgcgcga gtactcaagc ctggttctac tttattatta acggatttgc ctcttcttcc   5760
tgagagtacc gaagctttta aggagttcgt ttgggaacac attcattcgc gttttgtctc   5820
tcgcgaagat tatcctgagc tattagccga agcggagttc gaactcatcg aaatagatga   5880
tattactgat aatgtcatgc cctggctgga gcccaagttg aaggaagcga tcgaactgca   5940
tcgaccgcag gtcgaggcca ttattcctaa tgatacggag aaggcgatcg acgattggct   6000
ctatctgttc gagtacatga gcgagaactt aggctacatg atcgtgatgg ctaaaaagct   6060
gtaaacatct gttgttcacg acctgttgtg cgtcgggaaa ccgcgtctat aacagcttct   6120
aagtgctcat aagtatgggc aatattcgct ttctcagccg ttcaggtgat tttctttccg   6180
ttcgtgaggg cgtgaacagg ctcaaatgtc attatttttc ttcttccgtt atgttgcagc   6240
ggtggaatga gaggacgatg gcgatatagc tactgttcgt tcgggaagca taactctggg   6300
agaggtgcat gagcgttaat attcatcagc agcttaaaga aatcgaagat gccctgctca   6360
ataatagtgg ggtggctgtt acgctggatg tcgagtcttc agataagttg cggaaaagag   6420
aggcggaaga ttctcctgaa gcgatcgcta ttgtcggcct ttccggatat ttcccgcaaa   6480
gtgcgtcggt ggatgagttt tggcgtcact tggatcagga tgcgactctg attgaggaga   6540
ttcctgatag ccgtttcgat tggcgcaaag tgtttgatcc tacgggtgag cgtccgggta   6600
gtagctgtag caaatgggga ggcttcatcc ccgacataag gggttttgac ccggcctttt   6660
ttaatatccc gggcgctgaa gcgatcacgc tggacccgcg tcagcggctg ctactgatgt   6720
ccgcttatca gacgctcaat gatgcgggct atgcatcgca agcgctcaga cagagtaaga   6780
cgggggtttt cgttgccctg caggacaatg agtacctgca actgctcgcg gatgcgggca   6840
ttgatcctgg acagtggtat gcgcagactt gtttgctggc taaccgtatt tcctatttct   6900
tcgactggcg cgggacgagc gaggttgttg atgctcaatg tcccggtgca gccgtggcga   6960
tccaccgcgc cgtcagcgct ttgcgcaatg gcagatagca gctggcgtta gttggcgcgg   7020
cgaacctgtt gctgcgccct gagccttttg tgttgctatc cgagtcgggt caattgagcg   7080
agagcgcatc ggtccattcg tttggcgctc aggcgcaggg gcatctgcgt gccgaagggg   7140
```

```
tgtgcagtct gttgctcaag ccgctcacta aagcactggc cgatggtgat ccaatttatg    7200
cttcgatcaa gcactcagcg gtgaatttca acgggcaagg tggagcgtcc attgccgcgc    7260
caaatgtcga cagccatgtt gatctgatca agagttgcta tcaacaggca agagtcgatc    7320
cgcggcaggt acgttacatc gaggcgcaag gcatgggcaa tgtcttggcc gatttggtcg    7380
agtggcaggc ttttaatcgg gcgcttactg atattgcccg ccagcagcgg gtttcgcttc    7440
cgcctggtaa ttgcctgatc agtacgctca accaatgat ggggcatatg gagtcggcgt    7500
cggctctggg tgcgctgttc aaggttattc gtagcttgca tacgaggacc attcacaaga    7560
ttgctcactt tactcagtac catccggata tggattacca agggcaaccc tgcgccattg    7620
ccggtgaaac ggtggcttgg ccgcagatgg aggggctgcg gctagctggc attcattgtt    7680
atggaatggg gggagtcaac gctcacctgc tggttgagga gagcgtggca ggttactacg    7740
acgatagtga acttgggaca gtttcttcgt tgctagaaca cgtcctcatt gttctttcgg    7800
ctaaaacatc ggaaagccta agaatgatgg cgcgccggct tcagcaattt cttcagaaag    7860
cggatgctgt tcccgcgttg cgcgacatcg cttacacctt acaggtcggt agggacgcat    7920
tcgagcatcg cctggctcta gtcgtcgatt cgcagcaaca gttgattgag gggctggagt    7980
gctatttgga agaacggcaa ccgtcgcagg gggaaggagc tgtttaccag gggcaggtcg    8040
cctcagaatc gcagagcttg ccgttcacgg aggatgatct ggcggcagta gcacgttgct    8100
gggtcgcggg gggagcggtg ttatggccag ttccagttgg tccgaagaaa ccccgtcggg    8160
tacggctgcc cgcttatcct ttcgacaagc gtgcatattg ggttgatagt gccgtagttg    8220
aagctgagcg tgcgcctaat agcaaggcgc cggcgtctat gctgagtggc gaacggagta    8280
tcggcgacta tctgagagcg aaattgggag aagtcctgca ggtgccggtg gagcgtatag    8340
atccgcagca gcatctgtat gatttgggtg tcgattcgat tgtcgccatg aaactgctgc    8400
gtaatctggc gcgcgctttt ggcatcccgg tacgtggccg ggatctatta cagtattcga    8460
ccgttcaggc attgtctagg catctggcgc agtatctgga tcgggaccag gttgagtcgg    8520
tcggcgaaga tgaggaaccg cgtcagttga tggcttcacg gcgctgttcg ttgtccgaag    8580
gccagaaagg tctgtgggtg ctccagcagt tggcgtcgcg gatgactgcc tataacatcc    8640
cattgtgcgt gcgtatcgct caggtcctgg atatcacagc cttgcgagag gcatttgctt    8700
ggctgctcga acaatatccc atattgacta gtgttttcgt ccaggataat ggcgagcttt    8760
tccgagagtg ccacgtagcg gctgcattgc ccttctggca ggaagagacc aacactctgg    8820
atcaagcgca agtcaggatg cgcctgaagt gttttggcca agcagccctt cgagttggaaa    8880 agggcccgtt ggtgcggcta catgtcctca gttgcggtga gcatgaccat tatctgctgc    8940
tatgtgtaca tcatattgtc tttgacggag gttccttct cccggtattt ggcggtctgc    9000
tccagaccta tcagctaatt tcccagggac agacgctggc gaagagcact cgaactggcg    9060
aacagtacgc tgactttgtg ctgtgggagc aacgcatgct ggcgagtgcc gaggggcagc    9120
ggcatcgagc gtactggaag cggcaactgt ccggtgagct gccggtattg agcctgttca    9180
ccgacaatcc gcgcgatgcc ggccagcgct ttacaggcga tacctatggt ttccagctgg    9240
atgtgaatct gagtcggaag attagaaatt ttgctaaaca gcaacggttg aatctgtcca    9300
cattattcct ggcactgttc aagctgctgc tgcatcgtta cagcggccag agtgagctga    9360
tcatcggcat gccggagcag gggcgctccg aggagcgttt cgaggggtt gtcggctatt    9420 tcgtgaacat gttgccgata cgcagtcggg gcgtgggcag caaaccccctg gcggagttcg    9480 ctcgtgacct gcaactgagc atggcggatg cgatggacca tgccgtctac ccgtttccgg    9540
```

```
tgatggtcag ggatttgggt cgcgctcccg ctgaagacct tgcgccgatt tttcaggttg    9600
ccttcgaata ccagaacgta ttttccgctc aggatttgcg cctgttcaat cagagctatc    9660
gggaatcgtt gggggtgact ttcctggagg agttcgtgca ggaaggcgag tacgagttgg    9720
ctctggaggt tcgtgaggga gagatcgatt tcgccctgaa tctcaaattc aacccgacgc    9780
tctaccggat ggcgactatt gccaggatgg ccgagcatct gctgattctt gctgaacatg    9840
ccatcgacgc tccgctaagt ccctgccggg aactgacgat gttgagcgag cgggaacggc    9900
atctcttact gcatgagtgg aacgctacca ctgaacctta tccgtcttgt tgtttccatc    9960
agctctttga gaagcaggcg cgtgcgatgc cgcaggctat cgctgcgatt tttcaagagc   10020
agcggttgag ctatgccgaa cttgatgaga aagcgagcg gctggccatc tatcttcagc   10080
aatgtggcgt tcagcctaat cgaattgtgg cggtttgcct cgaacgttcc cttgacatgc   10140
tagtggcact catcggtatt gcccgttcgg gagccgcctg gttgccgttg gatccgaact   10200
atcctgatga tcgcttacgc ttcatgctca gtgacagcca ggcgcagcta ctgctgaccg   10260
aggaagggtt gcgggataag acagccgcta tcgtctccca gcggtgggt gagcgtttgc   10320
agatcgttgc catggatgga cactggccgg aaatcgagcg gcaggcgcgg acgagtgagt   10380
tgcagatgcg tgatgacccg cggaacttgg catatgtgat ctatacgtcg ggcagtaccg   10440
ggatacccaa aggagtgatg atcgagcatc gttcgttagt caacttcctg tattctatgc   10500
tcaatcgtcc gggtttgcgg gctaatgacc gcttgctggc cgttaccacc tattgcttcg   10560
atattgctgg gttggagctg cttgtaccat tgctgtgcgg tgcgtgttgc tgtatctgtg   10620
ctactgacaa actcaatgat tccgaggctt gcagggaga gatcgaacgt ctgcagccaa   10680
cggtaatgca ggcaaccccc tcgacctgga ccttgttgtt tcatggggt tggaacaacc   10740
gccaaggcgt gaagatactt tgtggcggcg aaccactgcc accggccttg cgtcagcgtt   10800
ttgccgagag cgccagccag acttggaatc tcttcgggcc gactgagact acgatttggt   10860
ctacggtatc gcggctcgac ttgacgaagg actcggtcga catcggtaca cccatcgcta   10920
ataccgggt ctatatcctg aatggtgatg atcagttggt tccgattggg gtgccggcg   10980
agctatgtat cgcgggcgac ggtttagcta ggggatatct cggcaatcca cagctcacgg   11040
cgcagaagtt cattgccaac cccttcgaac cgggaaaccg actctatcgg acgggcgatc   11100
tggcgcgttg gcgcgaagat ggtgttctgg agcatctggg ccgtctcgat cagcaagtca   11160
aggtacgtgt ttaccggatt gaactttcgg atatcgaaac ttggctgaac cggcatccgt   11220
ctgtcgcgca aagtttagtg gtcggacatg agcaagcggg tgggatgctg ctcgttgcct   11280
actatgtgaa agactctgaa tgggcgtccg tgtcttcaac cgaactcaga aactacttag   11340
ctgaacactt accggagtat atggtcccgg cttttttcg tgccctgtcg aacatgccac   11400
tgatgcccaa tggtaaggtg gatcgcaaag cgttgagcgc acgtgagctg gtggccgaag   11460
agtcggaaag cggcggtcgg ctgccgtgct cagatatag gcgtgaggtg ctcgatatat   11520
ggcgatcgtt gctggctgtt gagggaattg gcgtctcggt cggttttttc gaggtgggcg   11580
ggaattcgat tctgtcagtg atgctggcgc agcagatcag cgaagcgttc gggatcagat   11640
tcgccgcaac cgatttgttc aagtacccca ccattcggga tatcagcctg ttgatcggtg   11700
aaactcgcga acggagtgag acgaagactg ggacgatggc cggtgacggc agcggcaagg   11760
ctgactctgt acttcaggcg caggcgcgcg cagacagtc tgtcactggc tatcccgatt   11820
actatcagga tagcctggct attattggta tctcgtgcaa tatgccgggt gcgaggacac   11880
```

```
tcaggcaatt ctgggaaaac ttgcggcaag gcaaggaaag ctctactcgc ttgagcgaac    11940
gggagctgcg tcgtgccggt gtgccagaag agctcatccg ccatccagac tttgtgccca    12000
tgcaatacag catggagggc aaggagttgt tcgacccgga cttttcaat ctgtccgcga     12060 agaatgcgct cttcatggac ccgcagtatc gggtgctgtt gcagcaggcg tggcaggcga    12120
tcgaggacgc cgggtatgta gcgcaagata tccccgagac agcagtattt atgtcggcca    12180
gcaataactt ctacaagact tgctgcata gcgctggagc cgtggaaacg acggacgaat     12240
acgcggcttg gatagccggg cagggtggga ccatcccgac gatgatctcc taccagttag    12300
gcttcaaggg gccgagcttc gctgtgcact ccaactgttc gtcttcgctg gttgggctat    12360
atctggccag tcagtgcctg cggcttaagg aagcgaagta tgccctggtc ggtggtgcca    12420
cgctgttccc ggtggcgggt accgggcatc tgtatacgcc tgatatgaat ctctccagcg    12480
acggccattg caaggctttt gatgccgatg ctgatggact ggtcggaggt gaaggggcgg    12540
tggtgctgat ggttcgcaag gcgctcgatg ctatccggga tggtgatcct atctatgcgc    12600
tgatccgtgg cgttgccgtg aataacgatg gttcagacaa ggtcgggttc tatgcgccga    12660
gtgtcaacgg acaggcggcg gtgatccaaa aagcgctgga cattaccgga gtagatccgc    12720
agagcgttgc ttatgtcgaa gctcacggta ccggtacccg gctcggcgat ccggtcgaaa    12780
tcatggctct gaacgaggtt tatcgacgct atacagagaa aagacagttt tgccgtattg    12840
gctcggtcaa gcctaacata ggccatttgg acaccgttgc cgggttggct gggatgctca    12900
aggtcgtctt gagtctgaag catgctgagt tcttcccatc gattaactac cgcgagccca    12960
atccagcgat cgacttcact tcctctccgt tcgaggttgt cacgcagtta acgccgtggc    13020
ctgctggaaa cgaaccgcgg cgtgccgcgc tcagctcgtt cggtatcgga ggtaccaata    13080
ctcacgcgat tctagaggag tatgtagccc gtaccgatgc cgacaggtgg gaagacaacc    13140
agggtgtacc gctgccggag caagtagtgg tgctttccgc gaagactcag gatcggctgc    13200
aagccagtgt cgttaagctg tacgagtatc tgttacgcgc acaggcaaca acggaacagc    13260
tcgatctgca agacttggcg tacacccttc aggtggggcg tcaggctatg gactggcggg    13320
tggcttttct ggtcaaggat ctgcacgacc tcagtgaaaa gttggagcgg ttttttacagg    13380 gtgattcgct ggtgcaagat tgcttccagg ggcgggtagc tacgtcggta atggacgctg    13440
ccgcgacgcc gctgccggtt gcgcaagacc gcgagcaggc cgcgatagcc aaagcctggg    13500
tcaccggtcg gttggtcgat tggaaagaat taccgcgccg gggaacgcct caccgtatca    13560
gtctgccgac ttatccattt gcggaagaac gttattgggt agagatgccg gagttgcccg    13620
gtaggtcgga gagcgaagag cagactaaag agtggatcga gggacaggct gagcgcactt    13680
tgctggttgt gcatccgttg tggcaagctc atgcggtggt gaagcgcgag cgtccgctca    13740
tctttaccga acacctagtt tggttgtgtg ggttcgatgt ctccctggtt agggcattaa    13800
ctagatgtct tcctgaggga taccgcattg tcagcctgac gccggaaggt cggggagtag    13860
cgcagcgtta ccaatccctt tgtttgcaaa tgctcgaaag gctccagaaa tgcatcggtg    13920
atgcgacgaa gctcacgctg atacagctcg tgttgcccga cgaggggag tattcgctgt     13980 tcagcggttt gcacgctctg ctaaaaaccg tttcccagga aaacccacag aaggtcgcgc    14040
aactgatccg agtgagcagc ggagagacg ctcgttcgct ggctgacaag ctgatcgaga     14100
acacctttgc gcctgacgat agtcacctgc gttatgcgcc ttcgcgcatg cgtttggatt    14160
ggcaaacgct gcgcaggag gaaaccgttc tcgacatgcc gtggaaggag ggtggagttt     14220
acttattgac cggcggagcg ggcggccttg gtgttctgtt cgcggaagag attgcccgtc    14280
```

```
gggtacggaa ggccactctg gtactggtgc aacgctcgcc cttgtcagcg gcggcccggc    14340
gggccgagcg tatcgcggca ctgcgctctg attcgatcac cgtcatttgt cggcaagccg    14400
atatcagctg cgcaacctcc tgttcgcagc tgatcgctga tatcgcggag caatgtggaa    14460
cgatcgatgg catcctgcat accgcaggtg ttgtacggga tgctttcatt ctcaacaaga    14520
gcgcggcgga gtttcaggag gtattagctg ctaaggttgc tggtacagtg aatctggatc    14580
gtgcgactca ggcgttgggt ttggactttt tcctcctgtt ttcttctgcc gctgcagcat    14640
tcggtaatgc cggtcaggct gactactgcg cagctaacgc tttcctcgac gcttatgcct    14700
atgagcgcaa ccaacgggtg gctgccggtc agtgccgtgg tcatacgctt ccgtcggtt    14760 ggccattgtg gcgtgacggc ggtatgcgcc tcaatgagga ggcgcagcag gcgatgcggt    14820
ataccactgg attagtgccg atggacagcc ggagtggtat tcgagggctg tatcgcagct    14880
tggccgcaag gctcgggcat accctggtgt tggaagggga tgcgaccgcc attggctccc    14940
tgttggcaaa cgggacggcg cggtccgtct cggagctggg agtaccggcg gcgaatggca    15000
acgacctcga cgagacgctc aaagacaaaa ctatctatca actgaagcgt ttgttagcac    15060
aggtaatcgg tcgagcggtc gagcgcattg agtcatgtga accgatggat cggtatggtc    15120
tcgactccat cgctattacc cagctcaacc gtaagctgga agaacagttc ggcggccttt    15180
ccaaaacgct cttttaccaa taccagactg tggaggcgct ggctgaatat ctggtgctca    15240
ataaaacagt gtcctgccgc gcctggacgg gcttgcgcga tgagtcggtg ctggtcgcgg    15300
atgccgcacg ccgtggtctg ccgttgccgg agacggcacc cgtggtagag cgaaatgtat    15360
tgccggtggg taatgctgtt caggaaccca tcgcaatcat cggactaagt ggacgttatc    15420
ctcaggctga aaccttggaa gagttctggg agaacctcca ggctggtaag gattgtgtaa    15480
gcgagattcc cgaggatcgt tggcgactgg aaaacttctt ccaccccgat ccgaaggaag    15540
cggtggcgca gggtaagagt tacagcaaat ggggcggctt tatcgagggt ttcgctgaat    15600
tcgatccgct gttcttcaat atttctcccc gtgaagcact tgccatggac cctcaggagc    15660
ggctgttctt gcaatgcgcc tggcatgtgt tggaagacgc cggctacacg cgtcagtcct    15720
tacagcaggg cgggcataag gttggtgtat ttgtcgggat taccaagacc ggtttcgatc    15780
tgtatggccc ggaactgtgg catcgtgggg aaaggctgtt cccccacacc tcgtttagct    15840
cggtggctaa tcgggtctcc tattgcttga acctgaaagg gccgagcatg ccgattgata    15900
ccatgtgttc gtcttcgttg accgcgatcc acgaggcgtg tcagcacctg cgccagggtg    15960
actgtgatat ggccattgtc ggtggtgtga atatgtacgt tcacccgtcg acttatgtgg    16020
ggttatgttc ggcttatatg ctctctcggg atggtcaatg caggagcttc ggccagggcg    16080
gaaacggttt cgtaccggga aagggattg gtgcggttct gcttaagcct ctggcacgag    16140
cgcaggaaga cgacgatctg attcacgccg tcatccgtag tagtagtgtt aatcatggtg    16200
gcagaaccaa tggttacacg gtgcccaacc ccaatgctca ggcggaactg atcggcgatt    16260
gcctgaagaa agcgggggtc gacgcacgta gcattggtta catagaagcg cacggcaccg    16320
gcaccgaact tggcgatccg attgaggtga acggtctggc acaagccttt ggtcaggaag    16380
cgggtgagca tagccggtgc tttctaggct cggtcaagtc caacctgggg catttggaag    16440
cagctgccgg tatggccgga ttaaccaaag tcatcttgca gatgcgtcat gggcagattg    16500
tccctagtct gcatgctcag gtgttgaatc cgaacatcga ttttgcagcg actcccttta    16560
ctgttccgca gcaactggtc gagtggcggc gtacgatcct ccaggagagc ggtcggtccc    16620
```

```
gggagctgcc tcgcagagcg ggattgtcct cgttcggtgc gggaggctcg aacgcccacc   16680
tgatactgga agagtacatt gcgccggaac cggctcaacg tccccgtttc ggagagccgg   16740
gcaccgcggc ggttattctg ctgtcggcta agacgcccga gtgtctgcgt cgggtggtga   16800
gcgatctgct agcgttcatc gagagtgagc ttacacgtac cgttgatccc gatcagacgc   16860
tatttgatat cgcctatacc ttgcaggtgg gccgcgaagc tttggatgag cgcttagggc   16920
tggtggctgt ttctttgcaa gagctgagcc ggcagttggc ggcttttcta ggcgaagaag   16980
ccgagcagcc gttgctctat cggggcaggg tgcagaggaa taaggacgcc ttgcaggctt   17040
tggccaacga tgaggagttt caggaaaccg tcgataaatg gctggcccgg cgcaagtatt   17100
ccaaactgct gaagttctgg gtaacggggc tgtcggtgga ctggacgcgt ctgtactcgg   17160
atgttttacc gcgacggatc cgcctgccgg tttatccgtt cgttcgccaa cgttattggc   17220
tggacgcata ttcgctggag ccaatggtgc ctacggagca gccgtcggtc gtccctgtgg   17280
atgcggaggt atctggctct gacgctgggc gagaagccga tcttatgatg ttgggtcctg   17340
tgtgggacgc cgtggttgag caggggactg aggatttccc gccggccggc gcacggatag   17400
ctatggtggg gggaagcgag gcgcagaaac gagcggtatt tgagcaatat cccaaggcgc   17460
ttgagctagc tgccggcgcg gtcggcgccg ccagcattgc ccggctgggt cggcttgatc   17520
atgtggtctg gttcgcgccg gcgagccaga ctcaaggcat ggccgatgag cgcatcatcg   17580
acgcccaacg agacggtgtg ctggcgttgt tccagctggt gaaggtgctc ttggccgaag   17640
gctatggggt ggcagagttc ggcatgaccg tcatcacgac tcaggcattg caacatgcg    17700
ataccgagcg gatcgatcct acccatgccg ctgtacatgg cttggtcggc agtttggcca   17760
aggagtatcc gaagtggcgt ttgcgggcgc tggatatcga tgcgcgggct gaatggccgg   17820
tgccgggatt gtggcgattg ttacctcaca cgcgagggga aagtcgtgta tggcgaggct   17880
gtgaatggtt cgccagagg ctggtggcac tgaacggcat gcctgtagct aaagggcgag    17940
cttaccgtcg gcaggggtc tacgttgtca tcggtggagc gggcggcctg ggtatgacgt    18000
ggagtcgtat gatgatccgg gatcatcagg cgcagatcgt ctggctggga cgttcggcca   18060
aggatgcgac tgttcgagcc aagctggacg aggtggcgga cgacggggttg gctcctgact  18120
actggcagat tgatgcccgc gacgctgatg cttttgcgtca gaccttccgc caggtacgcg   18180
agcgttatgg acagattcat ggggtgattg tgtccacgct ggggggattac gaccaaagcg   18240
tggcgcagat gtccgaagcg ttgttccgcg agatcctttc cagcaagctc gatatcgggg   18300
ttcggctctc ccaatgccta cgtgacgaag cactggattt cgtggtgttc ttttcatcca   18360
tggtggcctt cggcagaagt ggcggtatgg ctgcctatag gcggcctgt gcattcaatg    18420
atacgttcgc ccggcagctg ggcaatgagc ttgcctgcg tgtcaaggtt atcaattggg    18480
gttattggaa ccttggcggc ggtacacgga tttccgcagc tttgaagagg cttgtcgagc   18540
agcgcggagt acgccctatc gaggcacgag agggtctgtg tgcgcttgca gtactgttgg   18600
acggcccgct gcggcaattg gcggtgaccc gtacttgcca gccggcggct atagaaactt   18660
ttgaggcgga acaatggctc accgtcaaag ccggcacgca ttcctgcttt gcgaatgtcg   18720
aggcttatca gcccacgcag cccatgccgc aagaaagtcc cgacgctgcg cggctgaatc   18780
tttggatcgt acgtctgttg tttgtgcagt tgcagtcgct gggtcttttt caggagacgg   18840
gattccagaa tgcgaccgca atacgccgac aggcgggat agttgataag tacgagcgtt    18900
ggtggcgcga aagcctgaat atcctcgcag aacatggcta tctgaggcta gcgggtgacg   18960
aagtagcccg catcgcgtct gctgacgaga ttggcgaatc cagccgggag cggctgtggc   19020
```

```
aagaatggcg ggaatgtaag acgcgcttct tggagcaacc acagactcac acgctggcgg    19080
tgttggtgga ggactgcctg agtcagttac cggaggtctt gcgcggtacg cggttggtca    19140
ccgatatcct gttccccaac ggttcaatgg aaaagatcga gggtctatac aaaaacaatc    19200
tgatctgtga ctacttcaac gatgtggttg ccggtgtggc gcaagcctac atccagcggc    19260
gcttagagaa cgaaccgaac gctgaaatcc gcctgttgga ggttggcgcc ggtaccggcg    19320
gcactacttc cacggtactg ccgcaactga atctatggcg tgcgttcatt gccgaatatg    19380
cctacaccga cctctccaaa tccttcttta accacgcgcg cctgcgttat ggcacggatt    19440
atccgtatat cacctatcgg ttgctgaaca tcgaagagcc actgatccag caggatatcg    19500
agatcggcac ctacgatatc ttaattgcta ccaatgtgct gcatgccacg cgcaacatgc    19560 gtaatacccct gcgtaatgct aaggcggcct tgcgcggcaa cggtattctg atccttaacg    19620
agatcagcga caaaaccatc ttcgcctcgg tattgtttgg ccttatcgat ggttggtcgt    19680
tagctgagga tgagcattgg cgcattccag gcagcccggg gctattcgcc gaaaactggc    19740
aagccttatt gcttcaggaa ggtttcgata aggtatcgtt tccagctcag gtcgcgcatg    19800
acctggggca acagatcatc gtggcgcaga ctaatggtgt cattcaccag catggcgctg    19860
gtccggtgct cgaaacggct gtcgccgata agcccttgcc tacgctggag tccgctgtag    19920
cggcagagag actggtagat aggagcagtg taccggcccg acgacaggat gtggccgcca    19980
gagtgcggga gttgattctg acagtctgg ctcaggcgtt aagcattggc cgcgagcaga    20040
ttgagcagga tatcccgttc tcggattacg gtattgattc gattctgggg gtcggtttcg    20100
tccagcgact caatgatgag ttggggctgt cgctcaatac caccttgctg ttcgattaca    20160
ccaccgtgca acgactggct gagcatattg tcgctgagta tggacacacg ctcgacgttc    20220
cggcggcatt acccggcccg gagctttcag tgagtgagcc ggcgatggac attccgttac    20280
cagcggtgca ggcggtgccg tcatcgctcc ctcggcggga ggctgtggta cagaccgatg    20340
gtatcgcggt gatcggtatg caggacagt ttccgggagc cgatagtgtc gatgcactct    20400
ggcagaacat ggttgcgggc gtcaacccgg taactgagtt gtcggaactc taccttcctt    20460
atcatgccta cagtccggag aaacagcccg gtaagagcta ttgtaagtgg ggaggggctt    20520
tacagggacg tgattgcttc gacccgttgt tcttcaatat ttccccccgc gaagcggaat    20580
cgatgaatcc gcaccagcgg ttgatccttc aggagagctg gaaagcactg aagacgctg    20640 gttatgcccc taggtcgcta tcagacagcc ggaccggcat cttttgtcggg gccgagcctt    20700 ccgcttatgt gcatgaatcg ttcgtgggcg cttctgatgc gatcgtagct tcgcggttgt    20760
cttattttct cgatctcaag gggcctgcat tcgtcgtcaa caccggctgt tcatcgtccg    20820
gtgtcgcgtt gcatctggct tgtgaaagtc tgcgcaacgg cgagactgaa gtggcgctgg    20880
cgggtggcgt atttgcggtg atggggcaga ctattctggt tggattggcg cagaccgaca    20940
tgctcagccg tacaggatgt tgctgtacct tcgatgcgga tgccgacggt atggtgatgt    21000
ctgaaggtgt gggcatggtt gtgctcaaac ggctggatca ggcactgagc gatgggata    21060 ccatctatgg agtgatccgt gcctcgggaa tcaatcagga cggagccagt aacggcatca    21120
ctgcacctag tggcattgcc cagcagcaac tgattactga cgtttatcgc cgctacgcca    21180
tcgatccgcg gcggatcact tacgtcgaag cccatggtac gggcactcgc ctgggcgatc    21240
cggtggaagc gaatgctctg gtgcgtgcgt tccgctcatt cactgagagt accggctatt    21300
gcgcggtcgg cagcatcaaa tcgcatattg ggcatacttc gtccagttcc gggtgattg    21360
```

```
gcctgatcag tattctgttg tgcctaaagc atcatcagct gcctggcatg cgacatttca   21420
aacggctaaa cccgttgatc gaattcgagc ggtcgccgtt ctatgtcaat gcgcgaatga   21480
tgccctggcg ttcgggtagc ggcgagccgt tgatggctgc cttgaattcg ttcggtcaca   21540
gcggtaccaa tgtacatctg gtggtagagg agtttgttcg gtcgaatagt gaagatcccc   21600
gcgtattgga cgatgtgagt tcgaccgcgc aacccgagtt gattttgctt tccaccaagg   21660
atgcggaacg gctatctgaa gtattaaaca atctggcgca ttttgtacgt caggcccaga   21720
atcagcccgc tgacctcgaa cggctctccc tggcggactt agcttatacg ctgcaaacgg   21780
gccgtgaagc gatggagcag cgcgttcgcg tgttggtagg ggacttggcg gggctgctcg   21840
aagcgctgtc ggcactgcgg gaggagcgtc cctgccccgt gtcggtgtgg agtggtcgag   21900
tcgaacccgg tccgagccgt ggagcggaga ctgtcaatgc tgatcagccc gccgcagagc   21960
ttctgcaacg aatcccgcag tggcttgccg agggtgctct cgatgaattg gcccaggctt   22020
gggtggctgg tgcgccgatc gattggtgcc aattgcggcg ccgacgtcca ccgcggcgcg   22080
tgcatttacc gtcctatcca ttcgcccggg aacgttattg gcggtcggag ccggcagtgc   22140
attcgcctgt ggtggctgcc ggactgcatc cgctggttca gcgtaatacc tccaccctag   22200
accggcactg ctttgaatcg agcttcgacg gcagtgagtt tttcttccgc gatcaccgag   22260
tgcaaggtca acctttgttg cctgcggtgg cttatttgga atgggcccga gcggcagcac   22320
agattgccct ggggaatgcc tgccccgatg ttgcactgaa gttgagcaat gtggtgtgga   22380
tcgggccgct gctggcggag cagccgatcg tggggacaat cactctgcaa gcccgggaag   22440
accgggggat tgattaccaa atcagtagtg tgtcggctgc tgggcagcag cctgtggtgc   22500
actgccaggg cattgctact actgagactg agaaggaagc cgcgccggtg ctggacttgg   22560
atgccttgcg gtctcgcttg acgcagaagg agattggggt cgagcgttgt tacgccgcgt   22620
tggaagccgc cggagtgaat cacggtccgg cgatgcgggg cttgcaagcg gtctcgcgaa   22680
atgctgagga agtattggcg acattgcgct tgccggcgga gacagtcggc gaggccagcg   22740
cttacgttct gcatccggct atcctcgatg ccgcgttgca agccagcatc gccctgacct   22800
tgcgcgacga cgaagtcgag ccatcgccgg agacttcgcc tagaccagtc ttgctgcctt   22860
tcgcactaga aagtttacgg gtttatgcac cttgctgcgc ttccatgtgg gcctggatac   22920
gtcttgtcgc agtggaacac gccggccagg cgttgcagcg cttggatgtg gatatctgta   22980
ctaaagaggg ggaagtctgc gtcgctctgc gtggcttcac gtcgcgctcg ctgccccgt    23040
cggggctac cgaaagccgc gcatctgctt ctgccgcttc ttcgactttg gtgagtacgg    23100
aaggcgtttc acggttcaag ggtgaggagt tctttctacg tgaccacagc ggcatgttgc    23160
ctgctgctgt gtacctggaa atggtgcggg cttttcgcca gggtaagcat gagcggaaaa    23220
ttaccgggct cagtcatgtg gtttggccca aggtcttgct ggtgagtggt gaaggacgcg    23280
aggtgcgtac ttgtctgacg aatgtcgata gaagcgcttt cctcatcagt gcctgcgaac    23340
agagctcgga agggccacag gaggtgacct attgccaggg caacctcctc ctgccagagg    23400
taatggaaga gcccggcgct gcgctggcca tcgaggccat cgcctaccgt tgcccgtcgg    23460
tgctagaggc taaacagtgc gatcgcttgc tccagtccac ccatggtccg gcattgatga    23520
gcgttcagca gctgcgttac agcgataggg aggcattggc acttctccaa ttaccggacg    23580
agctgcaaat gggttgggat gattatggat ggcatccgag tctgctcaat ggggcgatat    23640
tggctagtgt ggtttggtgt ctggctcgcg cgccgcggtc gcgcgccggg ctgccgatgc    23700
cttttcagttt ggaccggctg cgtgtcttcc agccgttcga gcggcagatg caagcctatg   23760
```

```
tgcgcagaca tggcagcgcg cgctccctgg gagaaaatct agagaaagtg gacatcgatc    23820
tgcttgactc gcagggtcgc tgcctggcct ccctcgaagg cttcaccctg gtattcgcgc    23880
ctgatgctaa ccggcttgtg tacgccattc cacagtgggt cgaacaagct ttgccggccc    23940
gcgtggcggc gtccgcacca ttagcggttc aggcaccggt ctttatcctt gccggtgccg    24000
gggagccttt acgccgggcg ttacacgata gttggccgga tgcgctgctg cacgagttgc    24060
cagagtcggc tttcgaggtg ggtgatggcc tgcggcaggc ggtcgtcgag gtattcggct    24120
ggtgtcggcg cttgcttccg tacaaaggcg ctgccttgca gcctttgttg gtgttgttgc    24180
ctgaggcgga gcgggaagtg actccccagg cgctcttggg cggtgctttg agtggtctgc    24240
ttaagactgt gcggctggag cacccgcgca tcacggccag gattatcagc tatccggtcg    24300
acgataccgt tactgccggc tggatgaagg tgttggccgc ggaaatcgca tctccggagg    24360
gtgatgttga aatccgctac gaccggcagg cacgtcggca tatcaaggtg ttgcacgaga    24420
tcacattgtc tgcygggggag cacggtgatt cacttttcag gccggacgat gtggtttggc    24480
ttaccggtgg tctcggaggg atcggccggc aaatcgcgcg ttatctgggc gtggagcgtc    24540
gggtacgcct ggcgctcagc ggtcgctcag cgattgacga taaggggggaa cgctttctcc    24600 aggagttgag acgggagggc gctgtggtga gctacctgag ggtagatgta gctgatgccg    24660
atgcggttgg gcgggcactc ctggctatcg aacaagaaca cggtggcttg acgggcatta    24720
ttcacagcgc tggtatcatt gccgacgact atctgaacag taaaaccacg gctcagttcg    24780
agcaggtact aaagcccaag gtcagcggtg ttgtgaattt ggacgcagct accgctaatc    24840
ggtctttgcg gtatttgctg gtgttttcat cgatagccgg tgttctgggt aacatggggc    24900
aggccgatta tgcagccgcc aacggcttttt tggatagctt cgcgcattac cgcgaagcat    24960
tagtgagaca gggcctgcgt tccggtaaaa gcttgtcgct gaactggccg ttgtggcgtg    25020
agggcggaat gcagatgggg cgtcacggtg aggccctgat gcagcaggcc acaggcatgc    25080
tcgccatgga aagcgcccaa gggttcgaag cgttggaagc cggcttgcga agcgcccaag    25140
cgcagatcct ggttgccttt ggtgagccgg tgagtattcg taaccggctg ctcacctttc    25200
ggatggatgc acccgagccg cctgcgcctt ctgtggtgga gatggatcgg gcaccgggtg    25260
aggaggtcgg tgagcaagag acgcaacagc tggttcgctc ggtggaagcg gagctgatca    25320
gaatagtggc cttttgttcaa cgtatacccg ccgaaaaaat caacgtgcgg cgagacatat    25380
cagcctatgg attcgattca attagcttta ccgaattcgc taatgcgctg aataaggcct    25440
acaagttgtc gctaatgccc actctattct ttgaaatagc cagtctggca gatttggcag    25500
gccatctgct tacccagcat cgtccggcat tgcttgaaaa gcatgctgtg gatgtggaga    25560
agccaagtga atgtcatagt ggcgtagctg ctcagatacc tatcccccact atgcccaagt    25620 cggagtgcat agccacgctt cccttgctac ctgtgggttc catcgaacca gagccccagg    25680
cggacctgga ggctgtcgcg gtgataggaa tggccggtaa gtttccaggt tgcgaagact    25740
tggaggattt ctggacgtgc ttgcagagct gccaggatct gatcagcgaa gtacctgagc    25800
aacgttggga ctggcggcgt ttctatggcg atccgcacca agagccgggc aagaccaaga    25860
tcaaatgggg tggttttgtc gcagatgccg actgctttga tgcgcgcttt ttcggtattt    25920
ctccagtgga agccgaagtc atggatccgc agctcaggct gttcttggag actgtctggg    25980
cggcgctcga agatgctggc tatcctgccg gtaggttggc tggagcagg accggcgttt    26040 tcgccggggt cgcgaccgct gactacaagg atttgttgat cgaggccaga gcgcggggc    26100
```

```
ttgtacagac gcccagtgaa cccttcccgt tcatgattgc taaccggatt tcctactggt   26160
tcaatttcaa cgggcccagc gaagccatcg ataccgcatg ctccagttcg ctaatcgcgg   26220
tgcacaaggc gatcgaaagc ctgcgcctgg gcagctgcga gatggccctg ccggtggtg    26280 tcaatgtctt gggtagcccg cgtatcacca ttgcgtctag ccaggcggga atgctcagtg   26340
aagatggccg atgcatgacg ttcgatgagc gagccaacgg ttatgtgcgt agcgagggcg   26400
tcgccatctt gctgctcaaa ccgctgcgca aggctattgc cgataacgat cggattcatg   26460
gtttgatccg tggcagtggc gaaaaccatg gcggtcgttc ggcctcgccc acggccccca   26520
ayggcaatgc gcagaagcgg ctgcttgtcg atatctatag ccgcgccgat attgatccgc   26580
gcaccatcag ctatatcgaa gcccatggta ctggcactgt gctgggtgat ccggtggagg   26640
ttaatggctt gaaggcggct ttccaagagc tgtatcagag ccgtgggctg gatgtgccgg   26700
agcagcctca ctgcggtctg aattcggtca aggctaacgt cggtcacctt gaagccgctg   26760
cgggtgcggt cggtatcgtc aaggtgctgc tgatgttgaa acaccggaag attccgggta   26820
atccgcatct gcggcgaccc aaccctatc tgcaattgga gggcacaccc ttctacttgg    26880
ttcgtgaaac gctggattgg ccacaaccga ccgatgtgcg tggtaatccg ctagcacggc   26940
gggctggcgt cagcagtttc ggtgtggggg atcgaatgc tcacgtgatt ctcgaagagt    27000
atcaggagcc tgagcggcag ggatggggta gtgaaccggc gtaccggcg ttgattgttc    27060 tgtcggcaaa agacgaagaa cggctggtct gcgtagcgca acgcctgcta cgtttcattc   27120
gtgattatgg cagtgagtta tatctgcatg acatcgcgta caccttgcaa gtagggcgtg   27180
aggccatgcc gcggcgccta gctttggcgg ttacctcctt ggcgcagctg gcggataggc   27240
tccagacatg gctagagcag ccgacgcaaa ccgaaggtgt tcaacaggga ctggttaccc   27300
aggaagcgga ggagcagttt gataccgttc ttggagatga agatagggct gctgctgtag   27360
aacgctgggt ggaaaaaggt cagtacgaaa aattgctgga tgcttggacg cgaggctggg   27420
cgatcgactg gaatgtactg tactgcactg ataccagacc gcggcgtatt ggcttaccca   27480
cctatccatt cgcgcgccgg cgttattggg tggcgagtgt tccccaagcg gaggataggg   27540
gcaaytctac actatccgaa cccgagccag aacagcggtc ggcaaagagc gatctactga   27600
cgtttgagga gtactgggct gaagttccat tggcagcacc cgccacggat agggtgaaaa   27660
ccttactgtg cctgtgcagt gacccggagc atcaacgccg gattgccgaa cagrtcgatt   27720
cacgggaccc tggggtccag ctgatcttca tcgagcaggg ggatgcgccc gctgagccgg   27780
atgaggcgcg ccagcggatc gatccattgc agccttcctc ctatagccgc gcgcttacga   27840
ccatcgccaa ggcgttgggg cgggtggatg cgctgctgta cctctggcct tgtgaggatc   27900
gccgttggat cagcaacgta ttaccggtgc tacatctgtt acaggcgttg tacgaaacgg   27960
gacttagacc acgcaaacta ctgttgtcgg gtgagtatgc cgatgcgctg aacgctgcc    28020 atctggactc atgggtggca tttgagcgtt ctttgggagt ggtgatgccc gagacccaag   28080
tggctgtggt ctttcgcgag cgggccgctg atacgggtga agttccccg acgtgggatt    28140 ggctggaggt gctcgtcgcg gagctattcg ctgagaagct gcgcagtgcc tgttatcggc   28200
aaggtgtacg gcatgttccc ctgatccgtc ctttggcgtg gcagcctggc agcgcaagtc   28260
cgttcaagca aggcggagtc tatttgatta ccggcggcgg tggcgggctg gggatgatag   28320
tcgccgaaca cttggcgaca gtttatgccg cgcgtctagt tttgagcgga cgctcctcga   28380 gcttagcgg ggaaaagtac gagctcttgc aagccagagg cgcgcaggtg ttgtacgttg    28440
gggctgatgt taccgacgtg catgccatgc aagaggtagt cgaccaggca cggcggcatt   28500
```

```
tcagtccgct caatggcgtg ctgcatattg ccgggctcaa tggcacggcc gaggtgctaa   28560
aggctgaggc tgatgccttc cagcgagtgc tcgacgcgaa atcaccggc agccaggtgt    28620 tggatcaagt gttacgcagg gagtcactag actttatttg ctattttgc tcatcgtcgg    28680 caattatagg tgacttcggt tcctgcgatt atgcgttggg caatcgcttc cagagcgcct   28740 atgcactta tcgtgcgcag atggtcgagt cttctgcatt atccggcaag accttggcga    28800
tcaattggcc gctctggcag gacggtggtc tgggtgtagg agatgctgag cagacgcgtt   28860
tttatctgca atcgagcggc cagcgtagtt tgtgctcgca ggaagcgctc gcgttgcttg   28920
aacagttact gacgcaggat cgggcgcagt gtctggtgtg ggcagggcag cctgacagat   28980
tgctccgctg ggtgaatcag gaaccgctcg aagcggctac agtcacggtg ccggaacctg   29040
tccgtgccgc caaggccgtg gctgagcggg ccgaactggg gggtggactc gatctgcaac   29100
aatgcctgtt gcgtgatctc aagacaaaaa tctgcgagct gctcggtact cagtacaacg   29160
aactggaaaa ccacgctaac ctggtggatt tcggtttcga ctccatcagt ctggccgaat   29220
tttctcgggt actgagccgg ttctattcac tggatatcag tccttcggta ttttcagcc    29280 actcgacatt gaaccgtttg acagcttact tcctggctga acatcggcag acgctggagg   29340
gcttctatca gcagcctcag cctgctgggc ctgagcatgc gccggtgccg accgaggttg   29400
cgcaagtgtc agtccctgtt ccggtgacgg cgttattacc tactggtaca tcgatcggta   29460
gtgcgtccca gggacaggat gagccgattg cgatcatcgg tctcagcggg cgcttcccac   29520
aagcccgcac gatcgaggag ctgtggcgga tcttggagca aggacgcgat gctatccagg   29580
aggtgccgat cgaccgtttc gactggcgga gttattacag cccgtcccag gaaatgagca   29640
agagcaacag caagtggggg ggatgcattc ctggaatcgc tgagttcgat ccgctgttct   29700
tcgagatttc accgttggaa gcggaacgca tggacccgcg tcagcggcat ctgatgcagg   29760
aagcctggtt ggcgctcgaa gatgccggct acgtcccga acaactggag tgcaacaaga   29820
tcagcatgtt cgtgggcgtt gaggaggggt gtgattatca gcgacggctg acacaacaga   29880
ccagcctgac gtcgatgcat aatggcatcc tggcttcccg gctggcttat tttctgaacc   29940
tcaaaggtcc ggtaatggcc atcaatactg cctgttcttc ggcgctggtg gctgtgcatc   30000
aggcgtgtca gagcctgcgt cacggtgaat gcgatacagc gatcgctgcg ggcgtcaacc   30060
tactggtcgc gcccgaagct tatgtcggta tgacgcaggc cggtatgctc tcgcccgacg   30120
gtaaatgtta cgttttcgac aagcgtgcca atggcttggt ccctggtgag gcggtggccg   30180
tggtcgtgct caaacggctg tcgaaagcgt tggcggatgg agatccgatt aaggcactga   30240
tccggggcag tggcatcaat tatgatgcaa aaaccaatgg tattaccgcg cccagtggtg   30300
cgtcgcagac cgaattgctt gaagggatyt atcggcagtg cgctttgcag ccccaggaca   30360
ttagttacat agtgacccat ggtactggta ctcaactggg cgatcccatc gaaatcaatg   30420
ctctttacga tgtcttcaaa ggcaagactg ataaacaggg tttctgtgcg ctgacttcga   30480
tcaaaagcaa tctgggccat acttttgctg cgtccggtct ggtcagtttg atcagcctgg   30540
tattggcgat taggcatcgg acgattccaa gcagcctgca ttgcgagcag aagaacgatt   30600
acatccgttg gcaggaaagc ccattctacg tcaatacccg caaaaagcac tgggagtgtg   30660
ctctggggca gccacggatc ggcgcagtca gtgcctttgg tatgagtggc accaatgcgc   30720
atgtagtggt gcaggagcat cagcctgccg aaccttcccg ctggtcaacg gctgctccct   30780
actacctctg ggtcgtatcg gccaagactg agacgacttt gcaagagcag atacggcaat   30840
```

```
gggaggacta cttgtcgcgg catccggacc tggatttcga ggcggtgagc tatacccctgc    30900
tgaaagggcg tcatcacttc aagtatcgct gtgcgattgt ggcgaaggac ctttcgcagg    30960
tgctccaggc gttgcgtcag gcactcgata gacagacaca agcgaatctc tgcatgggct    31020
gtgtcgatcg cgatttttct gggcagaaag ccattcgtga ctttatcgcg agccttgccg    31080
ctcaggggga ggcattgcgg gataagcctg acgactatcg tgacaatctg atcgcgctgg    31140
cggactttta ttgccagggt tatgaggtag cggacgtgca cttgttcgct ggccgtccgc    31200
aacggctgag tctgccgggt tatccgttcg ctagggaaca ctactggatc gatgagccgt    31260
cggcggctca tagagcggaa ctatctgaga ggagcttcga tacgcaacta aacccgttgc    31320
ttcagcgcaa cctctcgacc ttaagtgaac agcgatacgc cagtgctttc aagggcgacg    31380
agcgcttcat gctgcgcatc gcgcatgggc aagagttgct gattccgacg ctgttctatc    31440
tggaaatggc ccgtctggct gctcagcaga gcctcgatat gccggtacgg gcgctgaaga    31500
acatggtgtg ggcgtgtcct ttgtactatc agcaggggag cgattacgag ttgttcctta    31560
gtctgcatga gaaagacagc gacttgctgt ataccgtcga gatgcaaggt gagccggttg    31620
tgtgcggtca cttcggcgaa atcgactcca cggaggcggc tctccaattg ccggttgttc    31680
cggatattgc acggttgcgg gcgagtttgc ccgtggtgcc cgatgtggct ctaggcgcgc    31740
ccgagatggg tgtcgcgcgg atcagcgatg ttcaagccga tgcgacgacg ctattggcga    31800
ccttgaatgt gcctgcggat ggtgaagacc gctcgatgtg gttccaccct ctgcttatca    31860
atgccggttg gtggttattg caacagttcg tcggtgaccg agctgaggga ggaccgttgt    31920
taccgttctc gttgaagcag attaccgcgc cggctgctcc gccggatcag tcgctcctgc    31980
tcctgcggcg tcatgtacgc gacgttgagc aggggctgac ctgtgacatg attttctaca    32040
acagcaaggg cgagacctgt ctttatctgc aagagctaaa tgtgacgact ctcgacaggc    32100
tgtttgacct ttaacgcatc atcgctagtg aagtggatac tatgaatcag aaatttagat    32160
tatgcattat cggtggtgga ccactgggca tcggcttggg gcgtgagctg agtgaagggg    32220
ccatagatta tgacctttac gaagccgagt cggatttggg tggtgtatgg aatagagaag    32280
gcaagtgtgg ccgggtctat ccgtcgttgc atttgatttc acccaagttc aatacgcagg    32340
taccggacta tccaatgccg gatcattatc cggtgtatcc caatcacaaa atgatgctgg    32400
cgtatatgcg ttcctatgcc agggattttg gggtctacga gcatgcgatt ttcaatacgt    32460
cggtgactcg tctagaaccg gacggagagg gttgggaagt agagctgtcg agcggggagc    32520
gcaaacgcta tgaggtggtg gcggtatgta atggcgcaca acgcgtggcg cgctttcccg    32580
acccaccgca tccgggaact tttcaaggta aagttttgca ttcgatggac tacaaatcgc    32640
ctgatctggt gcgtgacaaa cgcgtactgg tggttggtgc aggtaactct ggttgcgata    32700
ttgcggtgga tgcatcacac catgctgagc aggtctatca cagcacacgg cggggctatc    32760
actacttccc aaagttcatc gacggtaaac cgacgccgca gtggatgcta caactgggta    32820
acaagtttga aaccaaggaa cagaccttgg cctatatgca gcaggtcttt aaggtggcag    32880
ggttcgatgg gatggattat ggcctgaaga agcctgacca tccgttggat ggtgcccatc    32940
cgatcatgaa ctcgcaaatc ctttatcaca tcggccatgg cgacattctg cccaaagaca    33000
atatcgagta cttcgagggc aatacggtct tttcatcga cggaacaaag gcggatgtag    33060
acctaatcat ttatgcgacc ggttatgatc gtgatttccc tttcattgat cacgcactcc    33120
tggaatggaa agacggtctc ccggacctgt tcatccatat cgtgccacgt aatctagaca    33180
acatttttctt ttttgggttc gtcaatgctg cggctggtct gggcgatggt ctgaggctgc    33240
```

```
aagggcagtt cgttagaagt tacgtcaggg cgcttcagca aaagagcaaa ggctatttca    33300
aatttattca gaccaaacag aacgataacc cggacttggg acaagattac ttcctggatt    33360
cccatcgaca tcgatgggag gtcgatttct ggaagtttat caagtgcgcg cgtagatacc    33420
gtgaaatgct ggatgaaatc tgacataact ccttcgggtg agcgtgatga ctttcaatac    33480
ttccaacgat caggacgcgg ccgcccgcga attcctcgag catgaactcg ccaaggcggt    33540
attagatcag tttaccgaga cacaatcgtc accgtccgtg gcacagataa tagatgttgc    33600
caccaactcg gtgaagaaca tctctccggc ggcggatgag acattggtca agttcaagga    33660
agagattgcc cagattgcct ccacagtgtt gaagatcccg gcggaacgcc tggatgttcg    33720
ggaaaatatg tctcgctatg gggttgattc gattgtcgtg acggaaatca tgaggtgtat    33780
ttccgaccat ctagatctgc ccattgcgcc gacggttttc ttcgaagcgg gtaatttcga    33840
agaacttgcg acaattcttt accagcgtta tcacaaacgc atcgacgaac gttaccagac    33900
ccaagcccgg gcccaggagc gagagtccgc gaaagtggcg ccacttcatg agcgcggacg    33960
ggctgttcag aagaatggcg agctcggtgt gatggaggca ctcggcagcg acgtctctggc   34020 gtggattcag cgtttccgca gcgtgacctc gtccgaggtc gctcgtccac aggcacaggt    34080
tcgccgggtc accaaagccg ctagagcgga cggcgaaata ctctacgagc ccatagcgat    34140
tattgcgatg gacggggttt tcccgcagag cgctgacctc ttggagtttg aacggcactt    34200
gcgccaagga gacgattgca tcagcgagat tcctgccgat cgttgggatt ggcgagaagt    34260
gtacggtgat ccgaaggagg gtgaattcac ccgtgtgaaa tacggtgggt tcgcacctga    34320
tatcgataag ttcgatccgc tgttcttcgg catgtctccc cgggaagccc agttaatgga    34380
tccgcagcac cggcagttca tccagtgtgt atggcggcta atcgagtcgg ctggttatgc    34440
acccaaggcg ctttcaggca gcaaggttgg gttgttcatc ggcatcaatc tgcaagatta    34500
tgcccatctg gttgatcggg ccgacgccat ggatgcactg cacctgacca gcttgggcca    34560
tatgttctgc cccaacagac tatctttcct gctcaacctg catggcccca gccaggtcat    34620
cgatactgcc tgttctagct cgtcggttgc cctgcatcgt gcggtgctga gcatccaata    34680
cgaaggttgt gaaatggcga ttgccggggg cgctaacctg ctgatttctc cggacatgca    34740
catcatgtac agcaaggttg ggatgatctg cgaggatggg cgctgtaaaa ccttctccaa    34800
ggaggccaac ggttatgtgc gcagtgacgg aattggtgct gtgctgctca gtcgctgca    34860 tcgagccgag gaggatggcg atatcattct agcggtgatc cgtggctccg cagagaatca    34920
cggaggcatg tcgacctcgc tgacggcgcc taatcccaag gctcaagcta gtctcatcgt    34980
tgaggcgcat cggaaggcca aggtcgatcc gcgtagcatc ggctacatag agtgccatgg    35040
tacgggcacg tccttgggcg atccgatcga gatcaatggc ttgaaattag cctttgaaca    35100
attgtaccgg gaagctggcc atgagttgcc gatgcgccca gctgcgggc ttggctcggt     35160 caagtccaac atcggtcatg cggagacctc cgcaggtatc gctggcgtca tcaagaccgt    35220
cctatcgctc agaaataagc gtctttatca gagtctccat agtgctgata tcaatccaat    35280
gatcgatttg gaacagtcac cgttcttcat cctacagcag ggccgggatt ggcaacgacc    35340
gttgatcgaa ggtcaggagc agccgcgccg tgcgggtatc agctctttcg gagctggggg    35400
ttccaacgcc catatcgtca tcgaggaata cttggtgccg ccgttacccg agccggtgct    35460
tcagggacct cttattatcc tgttgtcagc gaaaaacgct gctcgcctcg acgatatgac    35520
tcggcagctc ctgcactggc ttgagagcac cgagagggta ccgtctatcg ttgatattgc    35580
```

```
ctataccttg caggtgggac gcgaagcact gtcgcagcgt ttggccttga ttgtcactga  35640
tctggttgac ctcaagacca ggttgcgttc actgctagaa ggcggagagg agccgagtgg  35700
tgtttatcga ggcgatacca aggcgaacaa ggcggccttg caggaaatcg acgatgatga  35760
tcgttcgctt gagaagctca tcgcatattt tagccaagat gatgttcaca agttagccaa  35820
gctatggact caggggtcg aggtggactg gccgtccctg tacgcccgta tgcccttcgc  35880
cggccggtcg ccgcgccggg tggcactgcc gacttaccca ttcgctcggc agcgtcattg  35940
gatcgataag atagcgggta gtccgcaaaa tcggcgcgag gctgcggcta cctcgcctat  36000
tgtggctagc cggccagccg ggtatccgtt gctgcaacgc actgtcgcgg accctgctaa  36060
acggtgttac ggctgcgttc tgaccggtga agagttttt ctgactgacc accaggttaa  36120
aggtaataag gtgttgcccg gagtcgctta cctggaaatg gcgcgcgccg ctgttgaacg  36180
gattagcgct catgatgctc gagacaaagc tccactgtat ctcaagaatg ttgtttgggc  36240
tcgaccttg atggtcaacg gtgccacctc cttatatatc agccttgctc cggagcagga  36300
cgggcgggtg gcctatcgaa tttatagcga aggtgaaggg gagtcgaccg agattttgca  36360
tagccagggt agcgctattc tgcgcggctc cgagtcgggt agtgaagtcg ctaccgcccg  36420
gctggacctc gatgagttgc gcgagcgtat cacgggggga gctcctaacg cccagcggct  36480
ggagagcgcg cgttgctacg aggcttttcg cgccatgggc atcgattatg gtcctgcgca  36540
tcggtgcctg gagagtgtct atttttcagc caaggaagcg ttgcctgcgc ctgaggtttt  36600
ggcgaagctg gttctgcctg catgggctca ggagggtgcg gcggcatttg tgttacaccc  36660
cggtctgatt gattccggcc tgcaagcgtg catcggcttg atagtggggg ctggccatga  36720
gctgcctacg gaggctgaaa gtgaaatctc cggcatgacg gctacgctgc cttttgccct  36780
tgattcgttg acgctattgg cgccgccgag cgatatattg tgggtatggg tgcgttatgc  36840
cgatggtagt tccacgtcgg acaaagtgca gaagctggat atcgattttt gtgacgtgca  36900
cggccgggtc tgtatccgtt tgcgcggttt ctcctctcgt gccctagagg cagagcaagc  36960
tcccgactcc gcgaccacag tactttgtga gccgctctgg aatgaacgct ccgttgattc  37020
cagcgcccaa gtgttgtggg cacgccacga ggttttgctc tgcgatgtgc aggatgattt  37080
cgatgctgtc tttgaacaaa acttaggggt gaccctcggt gtgccctgtt cgcgcctagc  37140
gcttgacggt ccgctggaga accgttacca aaaggcggcg ctgggtgttt tcgaatggat  37200
caggcaagcc atcggcgaca agatcggtgg ctccctgttg ttacagatag tgatcccggc  37260
taccgatcga ggctgtttgc tggccggttt gtccggacta ctgaaaaccg ctaaccggga  37320
aaataaccgt ttccgcggtc agttgatcga actggagctg cgggaaacgg ctgagggagt  37380
tgctgcgaaa ctccaggctg acagccgggc tgcgcaggat acgcacatcc gtcatcggga  37440
ttcgctgcgc gaggttcggc attggcaagt ggtgccggct ggggcggtgt ccacagtgct  37500
gccatggaaa gacaacggtg tttacctgat cacgggaggt aacggtggct tggcttggct  37560
gtttgctgag catatcgccc agcatgcgcc tcatgcttcc ctggtcatgt gtggacgttc  37620
ggcattgacc tccgagcggc atcaggcgtt ggagcatttg cgtggtatgg gcccgcggct  37680
cgattatcga cgggtcgatg tgacccaggc cgcacaagtg gaggctttga tccgcgatct  37740
gacgacggtc tatgagcgca tcgacggcgt gctgcattgt gccggtctgt tgcgcgataa  37800
ctttatccag aaaaaaacgc cgcaggagtt cgctgaagtg ctagcaccca agtagccgg  37860
caccccttcat ttagaccatg caacccaggc gctggatctg gatttcttca tttttgttctc  37920
atctgctgcc ggcgtttggg gcagcgctgg acagaccgat tacgcagccg ccaatggctt  37980
```

```
cctggacgcc ttcgctagct accgccaggc gctgactgcg gcggggcggc ggcacgggcg   38040
cacgctttcg atcgattggc cattgtgggc ggaaggtggt atgcgcatgg aggccaatgc   38100
gcagatcatg atgcaacgag ctaccggatt gacggcattg cccagtgccg ctgggattga   38160
ggcgttctgt cgaatcatgg ggagcggcgc cacgcaaatg atggttatgc atgggcggc    38220 tgtgcgcatt cagcgcatgc tcgacgagtc tgccgaacct ctccgtgcgg cgcttcccgt   38280
acgctcggca acagccaccg aggagccggc ggcgcggggt cgttttgata ctcaggcttt   38340
gaaggccgga attgagcagt tgctattgca acgaatcgcg gagttgatga agttcgagct   38400
ggaagatttg gacgtcgaga cgcaattgac cgactacggt ttcaactcca tcactttgac   38460
cgacttctct aacaggttga atcagcagta ctcgttggag atgactccca cagtattctt   38520
cgaatacccg acggtaagcg agtttgccgg gtggttgagc acggaatacc cggatgtctt   38580
cgctcaggct ttgggtcttt ccatcgaaac acccgcggag ttccgtcccg aagtgcggac   38640
tgatgacgga gctagggagc cgtcatcagt cctctcatcc gtccaggccg agcggatgtt   38700
gggcggcata gccatgatgg cctctcaagc ggtatcggtt gacgatgccg ctgtcgcgat   38760
catcggcatg agtgggcgct ttccgatggc cgaggatatc caagcgttct ggagcaatct   38820
gctggagggt aaagattgta tcagtgagat tcccgaggac cgttgggatt ggcgagcgat   38880
ttatggcgat ccgaccaagg aggcgaataa gagcgatgtc aagtggggcg ggtttattga   38940
cggagtagcg catttcgatg ctcgtttctt tggcatctcg ccgcgagagg ccgagctgat   39000
ggatccccag cagcgtctgt tgatgcagta tgtctggaag gccgtagagg atgccggtta   39060
tgcgcccgct agtctgtcag gtagtcgcac ggcaatattc gtcggtacgg cgtctagtgg   39120
ttacggcgag ttgatggcgc aagagggttt agccatcgag agttacagct ctacgggtgt   39180
agtgggctcg gtagggccca accgcatgag ttatttcctc aacctgcatg gtcccagcga   39240
gcccgtggaa actgcctgct ccagctcgct ggtagcgatc catcgagcgc tgtcggcgat   39300
ggctatcggc gattgtgatc aggctatcgt cggtggcgtc aatctgctta tcagtccaca   39360
gacccatatc agcttcaaca aagccgggat gctatgcagc gatggacgct gcaagacatt   39420
ttccagcaaa gccaacggct atgtgcgtgg cgaaggtgtg ggcatgctca tgctgaagaa   39480
gctcaaggcg gcagagcagg ccggtaatca tatctatgcc gtgatacgcg gcagtgccga   39540
aaatcacggc gggcggggta gttctttgac tgctcccaat cccaaggcgc agacgcagct   39600
gatcaaggct gcttatgagc gcgccggaat cgatccgcgg agcgtgagtt atatcgaagc   39660
ccatggcaca ggtaccgagt tgggagatcc gatcgagatc aatgcgctga aggctgcttt   39720
caaagacctg tatcaggcaa ctggatcagt cgaggtgaca gcccccccact gtgcgctggg   39780 cgcggtcaag accaatatcg ggcatctgga gttagccgct ggtgtggcgg cgtcatcaa   39840 agtactgctc cagctcaagc ataagacact tgtcaaaagc ctgcattgcg atgaagtgaa   39900
tccgtatatc caattgcagg gcagcccatt ttacctgctc agcgagaccc agccgtggtc   39960
gactttgcgc gatgcacaag gacgcgagtt gccgcgtcgt gccggcatca gctcctttgg   40020
tttcggtggg gtgaatgcgc atctggtgct tgaggaatac ccacaagctg agtacatcgc   40080
cgaatcttcc atgaaagtt tacaagcgtc atcgacctgc gtagtgccgt tgtcggcgaa   40140
gaccccggag cggctcaaag tctatgcgtc cagtctactg gactttatta ccgcaccggt   40200
ggctgtgtct gggccggaag gagagggagc acatcagctc ttgactcgct ggatgcaggc   40260
catggttgcg gaaatcctag aaatagcggt cgaggagatc gagctaaccc agccgttgca   40320
```

```
ggaatacggt tttgataccg tccatgggt aattttgctg gcccgattca gggacgcatg   40380
gggagtggac gtgggtagcg cggtattact cgggcatcag accagtatta cttctttcgt   40440
tacgaccgta ttgcgcgaac agccgtcgct gcgggaacgc ttgagcgggg agcctgctgc   40500
ggtcgcagct tcacccgagc cgggccatcg ggtccggcgt gatattcgtc tggctgacct   40560
ggcttatacc ctgcaagtag ggcgtgacgc aatggcagaa cgcttagcga tgacggctga   40620
ctccatggag gagcttgagc acaagctgcg ggctttcgtt gaaggccgct ctggggaagt   40680
caaggacctg taccagggaa gtgtgaaaca gaataagcgc attttgtcag ccttcgcggg   40740
cgatgaagaa atgcaggagg cactagataa atggattcag cggggtaagc tcgccaagct   40800
actggaaatc tgggtggctg gactgaacat tgactggcag caactatatg gttcagaccg   40860
gtcgggaact ccgccgcatc gaatttccgc accgggctat ccgtttgccg aacagccgca   40920
ttggatacag actccctcca tgtcgcccgc tcctgtcccg gtgtccgcgc cggtagctgc   40980
gccgagggtc ctgcatccgc tagtgcatga aagcctttgc ggtccagggt tgactcgttt   41040
caagagccgt tttgagggca ctgagttttt cctggatgac caccgagtga aggggcgtaa   41100
ggtgatgccg ggggtcgcct atcttgaaat ggcccatgcg gcagcgcatc tggcgcaggc   41160
gatagcgccg tcttcgagag tatgtttgca ggatgttgcc tggatcagtc ctctgctggt   41220
cgaccagccg caggaagtcc tgatcgatat tgaacccggc cagggcgagc gtcgttcgtt   41280
cagtgtctac tgtatggcgg gtgatgggcg ccgtctgcat agtcagggag ggctgctgta   41340
tgttccgcag gattcggcgc agtctcgacc gtgcctggaa ctgcaagcgc tgctggcgca   41400
gtctggcatg cgtctgatta acgcggacca ttgctacgaa cggcttgctg ccggtgggct   41460
ggagtatggc cctgggcatc ggggtattca tcagctgtat gccggaaacg atcaggtgtt   41520
ggcgcatctg gttttgcccg aatcacttca ggccacggcg gggcattatg tgttgcatcc   41580
ttgtctggtg gatagcgcct tgcaggcatc tataggggttg gttctcacgg cttcggaaac   41640
tgcttctggc gggcgagagg caccattgat gctgccgttt gcagtgcaat cggtcgatgt   41700
tttcgcatct tgtgaaagcg taacctgggc gtggctacgt caccaggctg gaatcccggt   41760
gagcggacgc gtgcagaaac tcgatatcga tctatgcgac gagcggggta aagtctgcat   41820
acagatcaag ggttttcttt cgcgagtact ggctccggag ggtggacgct ctgaagcagt   41880
aacggctcat gagcggcgcg agccgttggg cgtatttgcg gcgcgcgcca caacgcccag   41940
tccggctccg gctccggctc tttcagcagt agcggaggtg gatgacgacg aactgtcgaa   42000
gcgggcgatt gattattta aagcgctttt gtcatctacc ttgaagttcc cggtggaaga   42060
aatcgcgccg gacgagacga tggatgccta tggcatcgac tcgataatgg tcgccgaact   42120
gaccagcacg ttggaaagtc attttggtcc tttgtcgaaa accctgtttt tcgaatacca   42180
gactctgggc gagctggtgg actatttcct agacgctcac cgtgcccggc tgttgcagct   42240
atgcgtaacg ggtggcgccg ggacttcgct tgccgcagac gctgtgctcg attctcctcc   42300
ctcgaccaag ccggcggttt tggtggaaca tttgccgcag ccggtgccga tggcggcggc   42360
cagcaatact gctctggata ttgccgtaat cggtatttcg gggcgctatc cgatggccaa   42420
tgatctggat gagttctggc tcaacctgcg ggaaggcaag gattgtgtga gcgaagtacc   42480
ctcgcaacgt tggaattggc gggatcatta cagcgaggag catagccggg cgggagggca   42540
tttctgtaaa tgggggcggtt ttatcgatga tattgataaa ttcgacccgc tgttttcaa   42600 catatctcca agtgctgcag aatacatgga tccccaggag cgcttattcc tcgaacatgc   42660
ctggatggcc atgaagacg ctggttaccg ccgtgaagac ctacggaagc ttgcacgtgg   42720
```

-continued

| | | | | | |
|---|---|---|---|---|---|
| ttccgctgct | gaagacctgc | cggggcaggt | gggggtctac | gccggtgtga | tgtatagcga | 42780 |
| atatcagttg | ctcggcattg | aagctgcccg | ccaggggaaa | ggcgctaccg | tggccaattt | 42840 |
| tcacgctagc | gttgccaatc | gagtgtccta | tgtgctcgac | ttgcatggcc | cgagcatgac | 42900 |
| ggtcgatacc | atgtgctcca | gttcgctgac | ggcattgcac | ctggcctgtc | aggatttgaa | 42960 |
| aacgggacgc | accgacatgg | cgttggccgg | tggagtcaat | ctcagtgtcc | atcccaataa | 43020 |
| atacagcgtc | ctgagtctta | acgaattcat | ttccagccag | gggcgctgca | ccagctttgg | 43080 |
| agagggtgga | gatggttatg | tgcccagtga | gggggttggg | gttgtactgc | tcaaacggtt | 43140 |
| ggtcgatgcc | gagcgtgata | gggaccatat | ccatgcggtg | atcaagagca | gtgttttgaa | 43200 |
| tcatggaggc | aagacacacg | gcttcagtgt | gccgaatccc | aaagcgcagc | agcatctgat | 43260 |
| cagccgggca | ttgcgcgaag | ctgaggtcga | tccccgagcc | attacgtatg | ttgaggctca | 43320 |
| tggcacaggt | actcctttgg | gcgacccgat | cgaagtgacg | gccttgagca | agccttcgc | 43380 |
| ccagtattca | ttgggtgggc | agccatactg | gatcggctcg | gtcaagtcca | atatcgggca | 43440 |
| tactgagtca | acagccggta | tcgctggttt | gagcaaagtc | attttgcaga | tgcgtgaggg | 43500 |
| ccagctcgct | ccgtcgctgc | attcacagac | cttgaatccg | aatatcgact | tcgcctcttc | 43560 |
| tcccttccaa | gtgaatcggc | aattgcgtga | gtggccgcgc | ccggtgcttg | atggacgtct | 43620 |
| ccagccacgg | gtagcgagtt | tgtcatcgtt | tggagcggga | ggctcgaacg | cgcatttggt | 43680 |
| gatttctgaa | tatatcgaac | cggtggaacg | gcgtgcgcct | gacactacgg | atagcaggcc | 43740 |
| ctgcttgatt | gtgctttcgg | ccaagagcga | agagcggctc | aaggcgtatg | ccggcaagct | 43800 |
| atgtgcattc | cttgaatctg | ccggtacgcg | gcttgagcta | tcgttacgca | atgtggccta | 43860 |
| taccctgcaa | gtcgggcggg | aagccatgca | acatcggttg | gctttcagcg | cccggtctat | 43920 |
| cgaggacgca | cggcgaatcc | tggaggcttt | tgcccagggg | cgagaagtcg | cgcggttgta | 43980 |
| ccgtggctat | gtgaaaaccg | ctcgtgatag | ccgttctggc | cggcgcgatg | agtccgttgc | 44040 |
| cgagccgata | cgtggcaagg | atcatgacgc | agtgctagcg | ctctgggtaa | aaggcgttga | 44100 |
| tgtgaattgg | caagagttgt | acgcggcgga | gagcgatcta | ccctaccgca | tcagtttgcc | 44160 |
| gacctatccg | tttgccagag | agcgctactg | gttgactttg | cctgagccac | cgccgcccgg | 44220 |
| tggggaacgc | cgtttgccga | atgcgccgat | agccttggcg | gtcctctcgg | acgcgttgct | 44280 |
| tggcagcccg | gcttggaagg | cgagggcagc | ggagcctgcc | gcggtgctgg | gcgattatgt | 44340 |
| cgagcgtcgg | ctgtacgttg | ttgggtcgtc | gatggaggtg | cccggcatcg | cctgcgtggc | 44400 |
| tttggactct | gatgggcaga | ccgtggatca | gcgcatcact | gattacgcta | cccagttgtt | 44460 |
| cggggacata | aagacactgt | tcagcgtaa | gcccaaaccc | aagggcgagg | tgttgttcca | 44520 |
| gattctactg | gcgcaggata | cgcccatggc | gggagcgcta | gccgcgctgc | tgaaaactgc | 44580 |
| ggcgatggaa | aatccgcagt | tcttcggcca | agtgctcgaa | ctgggtgcag | acatactgcc | 44640 |
| ggatccttcc | aaactgggtg | ctttgctgga | tgaaaacgcg | caggataggc | gtcatcccca | 44700 |
| tatacgctat | agccggagcg | ggcggcaagt | tccgagttgg | tcggtgctgt | cgatggcaag | 44760 |
| tgaaggcgaa | gcggtgtgga | agcagggggg | tgtatacctg | gttagcggtg | gtgtcggcgg | 44820 |
| gctaggattg | attttcgctc | gggagattat | tcgtcgggtt | agcgacgtaa | ctctaatcct | 44880 |
| gaccggtcgc | tcgcctttgg | aaggcgcgcg | cgcggcggct | gtccaggctc | tacgcgcctc | 44940 |
| aggcaccaac | gttgaatatc | gccgcgtcga | tgtcggtgac | cggcatgcgg | taacggacct | 45000 |
| gatcggcgaa | atcgagcgat | tctgtcgcga | ccgtgggtac | ggtgagttga | acggtgtcat | 45060 |

```
tcatgccgct ggagtgctcc gggataactt catcctcagg aagactcatg cgcagttcag    45120
tgaggtgatg gcggccaaag ttgccggcgt agtgaatttg gatctcgcca cacgtagcgc    45180
caacctcgat tttttcgtca tgttttcgtc tttggcaggt gtggtgggta atcctgggca    45240
gtgcgattac tcgacggcca acgcctttct cgatcattac acggtttacc gtaaccaact    45300
cgtggccaag ggtggaacat ctgcgccgaa agggcatacg ttgtcgatcg actggccgtt    45360
gtggcaggag ggcggcatgg atctggcgcc cgaacataag gaagagctgt ggcgaagcgc    45420
cggtataaag ccgatgcgca gcgagatcgg tatcgcggcg ttttatgcct gtttacaagc    45480
gggtgtcgaa caagcactgg tgcttgaggg ggatctaccg cggttgcgcc aactgttctt    45540
cgacgatcat tcccagccgg ttgttgatga agccgcacag ggcgctgaga cctgcacatc    45600
cgaacattct cctgattcct tagtccgggc ggttgagggc ttgctggtcc ggcatttgtc    45660
ggagctgctg aagttgccgg agcatcgtat cgagaccgat gtgccggtag agcattacgg    45720
catcgactcg gtgggcatga tgaggttgac cgtagaattg gaggaaacct tcggctcgct    45780
ttcgaaaact ttgttttttcg aatatcagga tgtgcaatcg ctggcagctt atttggcgca    45840
gactttccct gatcaggcac gagcattatg cggggagccg tctgcgcaag cggcgcccat    45900
ggaagtccct ataagctctg ctccagagcc gggcagtctg cccgctggtc tagttgaggc    45960
ggtggtgact gctggcgaag cagctgagtg gcagatgggc gagcgggata ttgccattat    46020
cggcatgtct ggccgtttcc cgttcgcacc ggatttggag gctttctggg aaaacttgag    46080
ccagggctgt gactgcatca ctgaaatccc gccgacacgt tggaagcatc aagagtattt    46140
cgatcctgaa aagggcaaac caggtaaaac ctactgtaaa tggggcgggt tccttgagag    46200
tatcgatcaa ttcgacccgt tattttttaa gatcccaccc gctcaagcgg aagtgctcga    46260
tccgcaggag cggcttttcc tagagaccgt gtggaatcta ttggaatcca gcggttatct    46320
gggggaaacc ttgcagcgta tcgctcagtc cagggtaggt gtgttcgtgg gatcgatgtc    46380
ccagcagtat cacgctttcc aagctgattt gacgcgggag tctttggtga cgatgtcgtc    46440
ccacagctcc atagctaaca gggtgtccta cttttttgac tttcagggtc ccagtgtagc    46500
cgtcgatacc atgtgttcgt ccgcgttggt ggctgtacac atggcctgtg aaagcctgct    46560
cagggaygac tgtaaggcgg cggtagccgg tggtgtcaac cttctattc acccgaagaa    46620 gtacataggc ctatctgcca gccagatctt gggtagccat cccgatagca gcagttttgg    46680
tcaaggtgat ggctaccttc cttccgaggg cgttggcgcc gtgctgttaa agccgttgcg    46740
cgaggcggtg gctgacaacg acactatcct gggcgtgatc aaatccacaa cgatcaatca    46800
cagcggccag tccaatggtt atttcgtgcc caatggtgcc gcccagacgg aattgatggt    46860
gagcaatttc accaaggccg ggattgatcc acggacgttg agttatgtcg agtccgcagc    46920
taatggttcg tcgttggggg atgccatcga aatcaacgcg ctaacggcag ttttggccg    46980 atacaccgcc gataagcagt tttgcgcgtt gggctcagtc aagtccaata tcggtcatgg    47040
agaagccgca tccggtattg cccaattgat caaagtacta ttgcagctca agcaccggca    47100
attggtacct actatcaagg cgcagccgtt gaattccaat attgatttca cgcatacgcc    47160
gttttgctta cagcgccgtc tcgaaccctg gcgtagacca tcgctagcac tagggatgg    47220 tccgatcgcg gaatatccgc ttcgggctac tgtcagttcg ttcggtgcgg gtggctctaa    47280
cgcccatctg atccttgagg aatttcctct ggatcgtcaa gaatcagaca acctggagca    47340
tgagcgcctg cccgattccg aagaacacct gctggtgttc agcgcaagaa ccgaggcgca    47400
gttgcaggcg gtggttcagc agatgctcgc tgagttggag aaagaacggt ctctgagcct    47460
```

```
ggccgacatt gcctttactt tgcagacagg acgtaaggcg atggattttc ggttggcggt   47520
cgtggtggaa ggcgttgaag cacgtcttcg ggccgtcgaa agtttgcggg cttatctgcg   47580
caacgaaacg cccggtccga cggtgtttgt cgacaatgta ttggaggatc actcgcgagt   47640
tagggagcag ctggtcggta gtgctggtca ggccatcttg caacgggcat taatggagcc   47700
ggatttgcgt gctctggctg gttactgggt caagggcatc aagttgccat ggcatcagtt   47760
gcatgctggt tggaagcgga aaagagtcgt cttgccgact tatccgttcg aacgcaaaag   47820
ctattggctg gggggaacg caggtcgagt cgtattgaaa gcgtctgaac atagcgagcg   47880
cgatgcagtt gagcctgaag tcgagagaaa tgggtcggcg tcgatcgagc gggtcatcgc   47940
gcaacgactg ggctcgatgc tcggtatgga tgaaggtgag atcgagatgg gccggagttt   48000
ccaggattac ggcgtagact ccatcgcgtc cagcgagttg tgccgtgcgc tggagcagac   48060
tttcaaggta cagatttcct cgcttgagct gttttccctg agttctctgg cggaactggc   48120
cgaattgatc gccgggcggc taccggagca gccattgaag aagcttaaaa aactggaaac   48180
gcccgagacg gtgtccgtaa gttcggtttc gatgccagtg tccgaagggc aaaaagggct   48240
gtggttgctc caccaacgct caccgaatat gagtgcctac aacgtacctc ttgtgttttg   48300
cttcaagggg gagttggatg tgtcgctatt ccgaaaggca tgcgaactga tgctcgaacg   48360
gcacccgata ctggggtcgg ttttccggct gactcgagag gatatccaac ggatcgagct   48420
cagggaggcg catatgggtt tcgagcatgt ctctgttgaa ctgcatcagc ggagtgagat   48480
tttggagcgg ctcagggact acagcaaaca gcccttcgat ctggagcagg gtcctctcta   48540
tcgagtatat ctattaactt cccgcacgga taacgatgcc tatgtattga tctgtgtgca   48600
ccatattgtg tttgacggca gttcggcgat gctgctgctc aaagatctgc tggctacgta   48660
tcgtaacctg ctgcatggcg gccagccggc taatatacgg cctgccgctg gttaccagtc   48720
gttcgtacat tggcagcggc aactgttgaa cagtgagaaa gggcaaacgc agctcgatta   48780
ttggaagacg cagcttttccg gcgaacaacc cgtgctctcg ttgccctacg actttccgcg   48840
tccggccatg ccgggggttcc atggagccag tgaagagctg acactttcac aggcattgtc   48900
gtccaggctt caggcgctca cgaagacgtt gcaggttaat ccttctgtag tgttttttagg   48960 tgctttcaag ctcttgttga accggtactc tggctatgac acattaggg tcggtatgcc    49020 aacttccggt cgttcgctac cggctttcca ggatcagatc ggttatttcg tcaacatgct   49080
ggtcattcgc agtcgagtga tcggacagca gtcggtcgct gattttctga aggtgttgca   49140
actgacggtc gctactgccc tggataacgc tgattgccca tttccagtcg tacttgaggc   49200
gctccgggga gacggcgagc cacaaagttc ctccttggttc caggtggtct tctcgtatca   49260
gaatttcatt cgagacggtg atagtgcctg gttgcaggct gatacgcagg gcactacagc   49320
cgtcgaactc gtttcgggta tcaaccagga aggtggaaat gatatcgccc ttgatgtata   49380
tcatgggggc gagcagttcc tactgaagat ggcgtatgac aaggatttgt tcgaggcggc   49440
taccattcgg cggatcatga cccactatgt caatctgctg gagtcgattg ccacccatcc   49500
acgaggatgc attgctgatc agacgttact ttcagcggac gagcggcaga aaattctcgg   49560
tgattggagt aatactggcg cgtctctctc catggagcgg cagaatattg tccaactgtt   49620
ccaacgccaa gttcgctcga ctccgcacaa aaccgctctg tgttcgagc agcagagttt   49680 gacattcgct gagctggacg atcagagttc gcggctgagc ctatgtctgg cgaactataa   49740
ggtggctcca ggcgatctag tcggagcctg tctaggacgt ggtgtgcgga tggtcgtggc   49800
```

```
gctgttggcg attctaaaag ccgatgcagt gtatgtgccg atagcgcccg attctccagt    49860
gcagcggatt tgccggttgc tggtagacag tggaattagt ttgctgttga gcgaattgga    49920
gctatgcaac tcttttctat ctgacctggg aacgatcgag tgcgtttgcc tagccatcga    49980
tgcaccgggg tgggagcctg aagagggcga gttacctgta ccgcctgtca tcgaagggcg    50040
gcaaccggcc tatgtcatct atacctcagg ctctaccggg cagcccaagg gggtcatcat    50100
cagccacgac tcgatcagtc accattgcca agtcatccgg gattactacc gaatcacggc    50160
acaggatgtg atcttgcaat ttgctccgat gaacgtggat gcagctttgg agcaattgtt    50220 gccgggggttg atcagcggag cgacggtagt gattcgttcg gagccgcttt ggtcgccgga    50280
catcttatgt cgcaaggtgg tggaattggg cattagtgtg ctcgatttac caccttccta    50340
tctttatgag ctactgctgg aaatccgtga tgtagcaggt tggagcaggc cgccttcatt    50400
acgtttggtg atcagtggcg gagaagcgtt gagcccggag acattgagcc tctggtgtgg    50460
ctgtgcgttg agcgaatgcc ggttagtcaa tgcctatgga ccaaccgaaa ctaccataac    50520
cagcactgtc tacgaaattg aatcgcgagc gcggacattt acgcgtctgc ccgagagcgt    50580
cccgatcggt cgtccattac ccggtgaaag cgcctatatc ctggatacccc agagaagacc    50640 gttgccggtg ggtgtgcctg gagagcttta tattggtggg gctggggtgg ccatcggtta    50700
cctgaaccgg cctgagctga ccgcctccac attcgtcgaa aatccattca tggccgggac    50760
gcgcctgtat aagaccggcg acgctgcgcg ttggctggcc gatggcaata ttgcgctgct    50820
tgggcgtttg gaccaacagg tcaagatcag gggcttccgg gtcgagtgcg gtgaaataga    50880
ggctgcttta caggcactgg atgtggtcaa gcatgtcgct gtgctagctc agcctactca    50940
gggcagtcac cggctggtgg cttttcttga gctggtgcaa ccggccctgc cagagtggaa    51000
acagcatttg aaacaggcac tgataaaaaa actgcctgaa cacatgattc cctctgtatt    51060
cgtttccctg ccacggattc cgttatcggt gagtggaaag gtggatcgta acgctctcaa    51120
gcacttggaa ctggccaaca ctgagtccga ggtattcgtt gctccacgta cttcaatgga    51180
aatccgtctg gccgaaatct ggcgtcgagt actcgatatt gatcggggttg gggtgcacga    51240 cagcttcttc gatcttgggg gacactcgtt attggcgctt cggttgatgt ccgcgatcaa    51300
gcagggattg ggatatgagt taccgatttc atccttgttc caggcaccta cgctcaccgc    51360
tcaggccgaa cttctggggc aggatgcagc cgtttggtca ccgttggtct gtctgcaagc    51420
gtcaggggag ttgtcgccct ggttctgtat tcatgcggct gctggtaatg ttttgtgcta    51480
tcgagaactg gccgaatgtc tgggaataga gcgcccattc tatgccttgc aagcgccgga    51540
tgcggttggg ggcggacatc cgggttcgat agtaggtctt gctgcgcttt acgttcgcgc    51600
catacgtata tttcagccgt ggggcccctta tttcctggct ggctggtcca tgggtggggt    51660
tgtggcctat gaaatggcgc agcaattgct ccaggcaggt gaacaggtgg aagtgctggc    51720
gcttttggaa agctatacgc ctgaagcgat cagaagtctt gaacgcaagg ctctgggggct    51780 gtcagcggag agtgacgatc gtatggataa gctcttgcgc acattcgcag tggagttggg    51840
tatcggtgaa acgccgtggg aactctctgc tgtggatttg gcacagggggc tcgaatggat    51900 actcaagcga ctcgaaggct ccaacttgtc cacagcgtcg tttgatctgg aacagttgca    51960
caagctgttc cgtctatatg aagcaaacct gaatgtctct tgatcgctatc gcctgcaacc    52020 ttactcaggc agagttgttc tgatctacgc tgaccaaacc cagcagatcg atgcggatga    52080
agctcagcac ttgggcgggt ggcagccttg gctgcgtagt ggacattgcc gcagtgctac    52140
catcgtgggt gatcattaca gtattttgca gcgcccacag gttgttcagc tcgcgaaggt    52200
```

-continued

```
gcttaccgcc ttggtgaaag atgatggctt agctactaag tatcgagaag taatggttta    52260
ttcgtaagct ccataaaccc cgtcttgcgc tgacggaacc aagctgccgc tagcagtcgt    52320
ctgcggcctg cggcaggcgc tcaataccgc tggcgcctga ccgttgttgg ccttggcgct    52380
cctccaccgg gcttctgcgc tatagaacca tctccccaaa ggtttttata aaagcttact    52440
tcacagagga ccattttca ggagcagacc aatctggctg tactaatgaa accgcccagc    52500
aagacgtgat gcaagcgttc ccaaaccccg tcgcttccc agtcttgcaa ccgccgccaa    52560
caggtcatgc ctgttccata gtccagctcc tttggcaagt cttcccaggg aatgccctgt    52620
gcatagcaca aacaagatgc cgttgaaggt agcccgatc                           52659
```

<210> SEQ ID NO 2
<211> LENGTH: 312
<212> TYPE: PRT
<213> ORGANISM: Unknown
<220> FEATURE:
<223> OTHER INFORMATION: Bacterial Symbiont of Paederus fuscipes
<220> FEATURE:
<221> NAME/KEY: MISC_FEATURE
<223> OTHER INFORMATION: PedA putative methyltransferase

<400> SEQUENCE: 2

```
Met Leu Lys Gln Arg Leu Phe Glu Cys Ile Ser Ser His Val Asp Gly
1               5                   10                  15

Ile Gly Tyr Val Pro Ile Asp Leu Gln Lys Ile Phe Asp Phe Gly Ala
            20                  25                  30

Ala Pro Ser Lys Asp Ala His Gly Ser Glu Ala Ser Asn Thr Asn Ser
        35                  40                  45

Asn Asp Glu Lys Glu Arg Leu Ala Ser His Ile Asn Gln His Tyr Asp
    50                  55                  60

His Thr Phe Phe Ser Glu Gly Leu Thr Ser Leu Leu Val Asp Gly Ser
65                  70                  75                  80

Asp Tyr Arg Asn Ile Gly Tyr Trp Asp Glu Thr Thr Thr Gln His
                85                  90                  95

Glu Ala Ser Glu Arg Leu Gln Asp Ala Leu Leu Asp Phe Ile Pro Glu
            100                 105                 110

Lys Ser Gly Arg Ile Leu Asp Ala Ala Cys Gly Met Gly Ala Ser Thr
        115                 120                 125

Arg His Leu Leu Glu Tyr Tyr Pro Ala Asp Asn Ile Trp Ala Ile Asn
    130                 135                 140

Ile Ser Glu Lys Gln Ile Glu Ala Thr Arg Arg Asn Val Pro Gly Cys
145                 150                 155                 160

His Ala Gln Val Met Asn Ala Val Asp Leu Ser Phe Glu Glu Gly Phe
                165                 170                 175

Phe Asp Asn Ile Leu Cys Ile Glu Ala Ala Phe His Phe Glu Thr Arg
            180                 185                 190

Gln Lys Phe Leu Glu Glu Ala Arg Arg Ile Leu Arg Pro Gly Gly Arg
        195                 200                 205

Leu Val Leu Ser Asp Val Leu Phe Ser Ser Glu Arg Leu Glu Gln
    210                 215                 220

Tyr Pro Ile Phe Pro Ser Ala Ile Asn His Leu Asn Asp Thr Glu Glu
225                 230                 235                 240

Tyr Arg Arg Leu Leu Lys Asp Thr Gly Phe Ser Gln Val Glu Ile Glu
                245                 250                 255

Asp Val Ser Asp Glu Val Trp Gly Ala His Phe Ile Tyr Ala Val Lys
```

```
                260                 265                 270
Arg Val His Glu Ala Phe Tyr Lys Gly Glu Leu Asp Ile Val Gln Leu
            275                 280                 285

Thr Glu Met Leu Trp Ser Tyr Tyr Gln Leu Asn Ser Ile Thr Lys His
        290                 295                 300

Cys Leu Phe Ile Cys Ala Gln Lys
305                 310

<210> SEQ ID NO 3
<211> LENGTH: 464
<212> TYPE: PRT
<213> ORGANISM: Unknown
<220> FEATURE:
<223> OTHER INFORMATION: Bacterial Symbiont of Paederus fuscipes
<220> FEATURE:
<221> NAME/KEY: MISC_FEATURE
<223> OTHER INFORMATION: PedB putative FMN-dependent oxidoreductase

<400> SEQUENCE: 3

Met Ile Thr Ala Glu Lys Leu Gly Ser Arg Leu Phe Lys Glu Asp Tyr
1               5                   10                  15

Gln Val Arg Tyr Ala Tyr Val Ala Gly Ala Met Ala Lys Ala Ile Gly
            20                  25                  30

Ser Ser Asp Leu Val Ile Ala Met Gly Lys Ala Gly Tyr Val Gly Phe
        35                  40                  45

Tyr Gly Ala Gly Gly Met Thr Leu Glu Glu Ile Glu Thr Ala Ile Gln
    50                  55                  60

Arg Ile Gln Gln Gly Leu Asn Arg Gly Glu Pro Tyr Gly Ile Asn Val
65                  70                  75                  80

Leu Ala Asn Leu Ala Asp Leu Glu Lys Glu Asn His Leu Ile Asp Leu
                85                  90                  95

Leu Leu Arg Tyr Gly Val Arg His Ile Glu Ala Ala Ala Phe Met Gln
            100                 105                 110

Ile Thr Pro Ala Leu Val Thr Phe Arg Leu Lys Gly Leu His Leu Asp
        115                 120                 125

Ala Ser Gly Lys Val Gln Ala Ala Asn Thr Leu Met Ala Lys Val Ser
    130                 135                 140

Arg Pro Glu Ile Ala Gln Leu Phe Leu Ser Pro Val Pro Ala Ser Ile
145                 150                 155                 160

Val Ser Leu Leu Leu Thr Glu Gly Arg Ile Asn Glu Gln Glu Ala Glu
                165                 170                 175

Leu Ala Gly Arg Ile Ala Val Ala Ser Asp Val Cys Val Glu Ala Asp
            180                 185                 190

Ser Gly Gly His Thr Asp Met Ala Val Thr Ser Val Val Leu Pro Arg
        195                 200                 205

Ile Ile Arg Leu Arg Asp Thr Leu Gln Gln Tyr Arg Phe Gln Ser
    210                 215                 220

Pro Val Arg Val Gly Ser Ala Gly Gly Ile Gly Thr Pro Glu Ser Ala
225                 230                 235                 240

Ala Ser Ala Phe Met Leu Gly Ala Glu Phe Ile Val Thr Gly Ser Ile
                245                 250                 255

Asn Gln Cys Thr Val Gln Ala Gly Thr Ser Glu Thr Val Lys Lys Met
            260                 265                 270

Leu Gln Ser Ile Asp Val Gln Asp Thr Ala Tyr Ala Pro Ala Gly Asp
        275                 280                 285

Met Phe Glu Leu Gly Ser Lys Ile Gln Val Leu Lys Lys Ser Val Phe
```

-continued

```
                290                 295                 300
Phe Pro Val Arg Ala Asn Arg Leu Tyr Asp Leu Trp Arg Asn Asn Gly
305                 310                 315                 320

Ser Leu Glu Gln Leu Ala Pro Thr Val Arg Lys Glu Leu Gln Asp Lys
                325                 330                 335

Tyr Phe Lys Arg Ser Phe Asp Asp Ile Tyr Gln Glu Thr Glu Arg Tyr
                340                 345                 350

Tyr Arg Lys Ala Ser Pro Ala His Ile Glu Lys Ala Glu Arg Asp Pro
                355                 360                 365

Lys Leu Lys Met Ala Leu Ile Phe Arg Trp Tyr Phe Val His Thr Met
370                 375                 380

Arg Leu Ala Leu Glu Gly Asn His Glu Gln Arg Thr Asp Tyr Gln Ile
385                 390                 395                 400

His Thr Gly Pro Ala Leu Gly Ala Phe Asn Arg Trp Val Lys Asp Thr
                405                 410                 415

Pro Leu Glu Asp Trp Lys Asn Arg Asp Val Thr Lys Met Ala Asp Tyr
                420                 425                 430

Leu Met Asp Ala Cys Ala Glu Tyr Leu Asn Lys Arg Ile Ala Ser Leu
                435                 440                 445

Thr Thr Asn Arg Met Ser Phe Thr His Asp His Ala Ala Val Ser Thr
450                 455                 460
```

<210> SEQ ID NO 4
<211> LENGTH: 334
<212> TYPE: PRT
<213> ORGANISM: Unknown
<220> FEATURE:
<223> OTHER INFORMATION: Bacterial Symbiont of Paederus fuscipes
<220> FEATURE:
<221> NAME/KEY: MISC_FEATURE
<223> OTHER INFORMATION: PedC putative acyltransferase

<400> SEQUENCE: 4

```
Met Lys Asp Leu Gln Asn Ile Gln Asn Thr His Pro Val Val Trp Met
1               5                   10                  15

Phe Ser Gly Gln Gly Ser Gln Tyr Phe Gln Met Gly Arg Gln Leu Tyr
                20                  25                  30

Glu Gln Asp Glu Thr Phe His Ala Trp Met Lys Ser Leu Asp Asp Asn
                35                  40                  45

Val Arg Asp Tyr Ile Gly Gln Ser Leu Leu Asp Ile Ile Tyr Asp Thr
        50                  55                  60

Gly His Glu Arg Ser Leu Pro Phe Asp Arg Leu Ile His Thr His Pro
65                  70                  75                  80

Ala Leu Phe Met Val Gln Tyr Ala Leu Ala Lys Ser Leu Leu Ala Arg
                85                  90                  95

Gly Leu Pro Ala Pro Asp Phe Leu Ile Gly Ala Ser Leu Gly Glu Phe
                100                 105                 110

Ile Ala Ile Ser Leu Ala Gly Asp Thr His Val Glu Asn Ile Leu Phe
                115                 120                 125

Asn Leu Ile Lys Gln Ala Arg Leu Phe Asp Glu Tyr Cys Asn Ala Gly
                130                 135                 140

Ala Met Leu Leu Val Ile Asp His Ile Asp Thr Phe Ser Thr Thr Pro
145                 150                 155                 160

Ala Phe Ser Lys Asp Cys Glu Leu Ala Gly Ile Asn Phe Asp His Cys
                165                 170                 175

Phe Val Val Ser Gly Pro Arg Thr Gly Ile Leu Gln Thr Arg Lys Ser
```

-continued

```
                180                 185                 190
Leu Thr Lys Gln Asn Ile Ala Cys Gln Leu Leu Pro Val Ser Ile Ala
        195                 200                 205

Phe His Ser Ser Trp Met Asp Glu Val His Glu Ile Phe Ile Gln Gln
    210                 215                 220

Phe Pro Glu Gln Ile Cys Arg Arg Leu His Thr Pro Val Ile Ser Cys
225                 230                 235                 240

Ala Leu Pro Val Pro Glu Gln Leu Thr Arg Phe Ser Ser Thr Tyr Trp
                245                 250                 255

Trp His Val Ile Arg Gln Pro Ile Ala Phe His Leu Ala Ile Asn Thr
            260                 265                 270

Phe His Gln Ser Ser Pro Asn Ala Val Tyr Leu Asp Leu Gly Pro Ala
        275                 280                 285

Gly Asn Met Ala Ala Ala Thr Lys Tyr Asn Leu Pro Ser Ser Ile His
    290                 295                 300

Tyr Arg Ile Leu Pro Thr Met Thr Pro Phe Gly Arg Asp Leu Glu Asn
305                 310                 315                 320

Ile Glu Ile Ala Arg Leu Arg Leu Leu Glu Leu Asp Gln Arg
                325                 330

<210> SEQ ID NO 5
<211> LENGTH: 364
<212> TYPE: PRT
<213> ORGANISM: Unknown
<220> FEATURE:
<223> OTHER INFORMATION: Bacterial Symbiont of Paederus fuscipes
<220> FEATURE:
<221> NAME/KEY: MISC_FEATURE
<223> OTHER INFORMATION: PedD putative acyltransferase

<400> SEQUENCE: 5

Met Lys Ser Tyr Leu Phe Pro Gly Gln Gly Ser Gln His Leu Gly Met
1               5                   10                  15

Gly Glu Gln Leu Phe Asp Arg Phe Pro Asn Ile Ile Glu Ala Ala Asn
            20                  25                  30

Asp Ile Leu Gly Tyr Ser Ile Lys Thr Leu Cys Leu Glu Asp Pro Gln
        35                  40                  45

Arg Gln Leu Arg Leu Thr Gln Tyr Thr Gln Val Ala Leu Tyr Val Val
    50                  55                  60

Asn Ala Leu Thr Tyr Arg Gln His Leu Gln Gln Gly Gly Leu Pro
65                  70                  75                  80

Asp Phe Val Ala Gly His Ser Leu Gly Glu Tyr Asn Ala Leu Glu Ser
                85                  90                  95

Ala Gly Val Phe Ser Phe Glu Asp Gly Leu Arg Leu Val Gln Lys Arg
            100                 105                 110

Gly Asp Leu Met Ser Gln Ala Pro Arg Gly Ala Met Ala Ala Ile Leu
        115                 120                 125

Gly Ile Ser Ala Asp Ser Val Ala Gly Ile Leu Ala Glu Gln Gly Leu
    130                 135                 140

Thr Arg Ile Asp Ile Ala Asn Tyr Asn Ala Pro Thr Gln Thr Ile Ile
145                 150                 155                 160

Ser Gly Leu Glu Ala Asp Ile Arg Asp Ala Gln Ala Val Phe Glu Ser
                165                 170                 175

Cys Gln Ala Met Tyr Val Pro Leu Asn Thr Ser Gly Ala Phe His Ser
            180                 185                 190

Arg Tyr Met Gln Ser Ala Arg Asp Glu Phe Ala Gln Phe Leu Glu Ala
```

-continued

```
                195                 200                 205
Phe Glu Phe Arg Asp Pro Gln Ile Pro Val Val Ala Asn Val Thr Ala
    210                 215                 220

Lys Pro Tyr Val Gly Thr Glu Val Val Arg Thr Leu Ala Asp Gln Leu
225                 230                 235                 240

Thr Gly Ser Val Arg Trp Leu Asp Ser Met Arg Phe Leu Leu Asp Gln
                245                 250                 255

Gly Val Thr Glu Phe Arg Glu Leu Gly Pro Gly Asp Val Leu Ser Lys
            260                 265                 270

Leu Val Glu Ser Ile Arg Ser Ser Ala Met Ser Lys Pro Val Ser Glu
        275                 280                 285

Phe Ala Ala Glu Asn Ser Gln Gln Leu Val Asp Glu Trp Asn Arg Thr
    290                 295                 300

Cys Pro Ile Gly Ser Arg Val Arg Val Lys Gly Tyr Asp Asp Ile Leu
305                 310                 315                 320

Val Thr Lys Ser Arg Ala Val Leu Leu Phe Gly His Arg Ala Ala Ile
                325                 330                 335

Tyr Met Glu Asn Tyr Gln Gly Tyr Phe Ala Leu Ser Glu Val Glu Pro
            340                 345                 350

Leu Ile Glu Gln Gln Pro Leu Val Glu Lys Val Trp
        355                 360

<210> SEQ ID NO 6
<211> LENGTH: 273
<212> TYPE: PRT
<213> ORGANISM: Unknown
<220> FEATURE:
<223> OTHER INFORMATION: Bacterial Symbiont of Paederus fuscipes
<220> FEATURE:
<221> NAME/KEY: MISC_FEATURE
<223> OTHER INFORMATION: PedE putative methyltransferase

<400> SEQUENCE: 6

Met Gln Thr Ala Ile Ala Asp Val Glu Lys Val Ala Thr Leu Tyr Asp
1               5                   10                  15

Ser Ala Glu Gly Gln Val Gly Pro Ile Leu Phe Gly Gly His Met His
            20                  25                  30

Trp Gly Tyr Trp Asp Glu Val Thr Gly Glu Gly Asn Phe Ala Asn Ala
        35                  40                  45

Ala Glu Arg Leu Ala Gln Ile Met Ile Ala Lys Ala Pro Ile Lys Ala
    50                  55                  60

Gly Gln Lys Phe Ile Asp Met Gly Cys Gly Phe Gly Glu Ser Ala Leu
65                  70                  75                  80

Lys Leu Ala Lys Ala Lys Gly Cys Phe Val Asp Gly Ile Thr Ile Ser
                85                  90                  95

Lys Glu Gln Gln Leu Ser Ala Ile Thr Arg Ala Glu Ala Glu Gln Leu
            100                 105                 110

Gln Glu Arg Val Arg Phe Ile His Gly Ser Ala Leu Asn Ile Pro Cys
        115                 120                 125

Glu Asp Gln Ser Tyr Asp Gly Gly Trp Phe Phe Glu Ser Ile Phe His
    130                 135                 140

Met Gly His Arg Lys Ala Leu His Glu Ala Ala Arg Val Leu Lys Pro
145                 150                 155                 160

Gly Ser Thr Leu Leu Leu Thr Asp Leu Pro Leu Leu Pro Glu Ser Thr
                165                 170                 175

Glu Ala Phe Lys Glu Phe Val Trp Glu His Ile His Ser Arg Phe Val
```

-continued

```
                180                 185                 190
Ser Arg Glu Asp Tyr Pro Glu Leu Leu Ala Glu Ala Glu Phe Glu Leu
        195                 200                 205

Ile Glu Ile Asp Asp Ile Thr Asp Asn Val Met Pro Trp Leu Glu Pro
210                 215                 220

Lys Leu Lys Glu Ala Ile Glu Leu His Arg Pro Gln Val Glu Ala Ile
225                 230                 235                 240

Ile Pro Asn Asp Thr Glu Lys Ala Ile Asp Asp Trp Leu Tyr Leu Phe
                245                 250                 255

Glu Tyr Met Ser Glu Asn Leu Gly Tyr Met Ile Val Met Ala Lys Lys
        260                 265                 270

Leu

<210> SEQ ID NO 7
<211> LENGTH: 8601
<212> TYPE: PRT
<213> ORGANISM: Unknown
<220> FEATURE:
<223> OTHER INFORMATION: Bacterial Symbiont of Paederus fuscipes
<220> FEATURE:
<221> NAME/KEY: MISC_FEATURE
<223> OTHER INFORMATION: PedF mixed type I polyketide
      synthase/nonribosomal peptide synthase
<220> FEATURE:
<221> NAME/KEY: misc_feature
<222> LOCATION: (7136)..(7136)
<223> OTHER INFORMATION: Xaa can be any naturally occurring amino acid

<400> SEQUENCE: 7

Met Ser Val Asn Ile His Gln Gln Leu Lys Glu Ile Glu Asp Ala Leu
1               5                   10                  15

Leu Asn Asn Ser Gly Val Ala Val Thr Leu Asp Val Glu Ser Ser Asp
                20                  25                  30

Lys Leu Arg Lys Arg Glu Ala Glu Asp Ser Pro Glu Ala Ile Ala Ile
        35                  40                  45

Val Gly Leu Ser Gly Tyr Phe Pro Gln Ser Ala Ser Val Asp Glu Phe
    50                  55                  60

Trp Arg His Leu Asp Gln Asp Ala Thr Leu Ile Glu Glu Ile Pro Asp
65                  70                  75                  80

Ser Arg Phe Asp Trp Arg Lys Val Phe Asp Pro Thr Gly Glu Arg Pro
                85                  90                  95

Gly Ser Ser Cys Ser Lys Trp Gly Gly Phe Ile Pro Asp Ile Arg Gly
            100                 105                 110

Phe Asp Pro Ala Phe Phe Asn Ile Pro Gly Ala Glu Ala Ile Thr Leu
        115                 120                 125

Asp Pro Arg Gln Arg Leu Leu Leu Met Ser Ala Tyr Gln Thr Leu Asn
    130                 135                 140

Asp Ala Gly Tyr Ala Ser Gln Ala Leu Arg Gln Ser Lys Thr Gly Val
145                 150                 155                 160

Phe Val Ala Leu Gln Asp Asn Glu Tyr Leu Gln Leu Leu Ala Asp Ala
                165                 170                 175

Gly Ile Asp Pro Gly Gln Trp Tyr Ala Gln Thr Cys Leu Leu Ala Asn
            180                 185                 190

Arg Ile Ser Tyr Phe Phe Asp Trp Arg Gly Thr Ser Glu Val Val Asp
        195                 200                 205

Ala Gln Cys Pro Gly Ala Ala Val Ala Ile His Arg Ala Val Ser Ala
    210                 215                 220
```

```
Leu Arg Asn Gly Glu Ile Glu Leu Ala Leu Val Gly Ala Ala Asn Leu
225                 230                 235                 240

Leu Leu Arg Pro Glu Pro Phe Val Leu Ser Glu Ser Gly Gln Leu
            245                 250                 255

Ser Glu Ser Ala Ser Val His Ser Phe Gly Ala Gln Ala Gln Gly His
        260                 265                 270

Leu Arg Ala Glu Gly Val Cys Ser Leu Leu Lys Pro Leu Thr Lys
        275                 280                 285

Ala Leu Ala Asp Gly Asp Pro Ile Tyr Ala Ser Ile Lys His Ser Ala
        290                 295                 300

Val Asn Phe Asn Gly Gln Gly Gly Ala Ser Ile Ala Ala Pro Asn Val
305                 310                 315                 320

Asp Ser His Val Asp Leu Ile Lys Ser Cys Tyr Gln Gln Ala Arg Val
                325                 330                 335

Asp Pro Arg Gln Val Arg Tyr Ile Glu Ala Gln Gly Met Gly Asn Val
                340                 345                 350

Leu Ala Asp Leu Val Glu Trp Gln Ala Phe Asn Arg Ala Leu Thr Asp
        355                 360                 365

Ile Ala Arg Gln Gln Arg Val Ser Leu Pro Pro Gly Asn Cys Leu Ile
370                 375                 380

Ser Thr Leu Lys Pro Met Met Gly His Met Glu Ser Ala Ser Ala Leu
385                 390                 395                 400

Gly Ala Leu Phe Lys Val Ile Arg Ser Leu His Thr Arg Thr Ile His
                405                 410                 415

Lys Ile Ala His Phe Thr Gln Tyr His Pro Asp Met Asp Tyr Gln Gly
                420                 425                 430

Gln Pro Cys Ala Ile Ala Gly Glu Thr Val Ala Trp Pro Gln Met Glu
        435                 440                 445

Gly Leu Arg Leu Ala Gly Ile His Cys Tyr Gly Met Gly Gly Val Asn
    450                 455                 460

Ala His Leu Leu Val Glu Glu Ser Val Ala Gly Tyr Tyr Asp Asp Ser
465                 470                 475                 480

Glu Leu Gly Thr Val Ser Ser Leu Leu Glu His Val Leu Ile Val Leu
                485                 490                 495

Ser Ala Lys Thr Ser Glu Ser Leu Arg Met Met Ala Arg Arg Leu Gln
            500                 505                 510

Gln Phe Leu Gln Lys Ala Asp Ala Val Pro Ala Leu Arg Asp Ile Ala
        515                 520                 525

Tyr Thr Leu Gln Val Gly Arg Asp Ala Phe Glu His Arg Leu Ala Leu
        530                 535                 540

Val Val Asp Ser Gln Gln Gln Leu Ile Glu Gly Leu Glu Cys Tyr Leu
545                 550                 555                 560

Glu Glu Arg Gln Pro Ser Gln Gly Glu Gly Ala Val Tyr Gln Gly Gln
                565                 570                 575

Val Ala Ser Glu Ser Gln Ser Leu Pro Phe Thr Glu Asp Asp Leu Ala
            580                 585                 590

Ala Val Ala Arg Cys Trp Val Gly Gly Ala Val Leu Trp Pro Val
        595                 600                 605

Pro Val Gly Pro Lys Lys Pro Arg Arg Val Arg Leu Pro Ala Tyr Pro
    610                 615                 620

Phe Asp Lys Arg Ala Tyr Trp Val Asp Ser Ala Val Val Glu Ala Glu
625                 630                 635                 640

Arg Ala Pro Asn Ser Lys Ala Pro Ala Ser Met Leu Ser Gly Glu Arg
```

```
                    645                 650                 655
Ser Ile Gly Asp Tyr Leu Arg Ala Lys Leu Gly Glu Val Leu Gln Val
            660                 665                 670
Pro Val Glu Arg Ile Asp Pro Gln Gln His Leu Tyr Asp Leu Gly Val
            675                 680                 685
Asp Ser Ile Val Ala Met Lys Leu Leu Arg Asn Leu Ala Arg Ala Phe
690                 695                 700
Gly Ile Pro Val Arg Gly Arg Asp Leu Leu Gln Tyr Ser Thr Val Gln
705                 710                 715                 720
Ala Leu Ser Arg His Leu Ala Gln Tyr Leu Asp Arg Asp Gln Val Glu
            725                 730                 735
Ser Val Gly Glu Asp Glu Pro Arg Gln Leu Met Ala Ser Arg Arg
            740                 745                 750
Cys Ser Leu Ser Glu Gly Gln Lys Gly Leu Trp Val Leu Gln Gln Leu
            755                 760                 765
Ala Ser Arg Met Thr Ala Tyr Asn Ile Pro Leu Cys Val Arg Ile Ala
            770                 775                 780
Gln Val Leu Asp Ile Thr Ala Leu Arg Glu Ala Phe Ala Trp Leu Leu
785                 790                 795                 800
Glu Gln Tyr Pro Ile Leu Thr Ser Val Phe Val Gln Asp Asn Gly Glu
            805                 810                 815
Leu Phe Arg Glu Cys His Val Ala Ala Ala Leu Pro Phe Trp Gln Glu
            820                 825                 830
Glu Thr Asn Thr Leu Asp Gln Ala Gln Val Arg Met Arg Leu Lys Cys
            835                 840                 845
Leu Ala Lys Gln Pro Phe Glu Leu Glu Lys Gly Pro Leu Val Arg Leu
850                 855                 860
His Val Leu Ser Cys Gly Glu His Asp His Tyr Leu Leu Leu Cys Val
865                 870                 875                 880
His His Ile Val Phe Asp Gly Gly Ser Phe Leu Pro Val Phe Gly Gly
            885                 890                 895
Leu Leu Gln Thr Tyr Gln Leu Ile Ser Gln Gly Gln Thr Leu Ala Lys
            900                 905                 910
Ser Thr Arg Thr Gly Glu Gln Tyr Ala Asp Phe Val Leu Trp Glu Gln
            915                 920                 925
Arg Met Leu Ala Ser Ala Glu Gly Gln Arg His Arg Ala Tyr Trp Lys
            930                 935                 940
Arg Gln Leu Ser Gly Glu Leu Pro Val Leu Ser Leu Phe Thr Asp Asn
945                 950                 955                 960
Pro Arg Asp Ala Gly Gln Arg Phe Thr Gly Asp Thr Tyr Gly Phe Gln
            965                 970                 975
Leu Asp Val Asn Leu Ser Arg Lys Ile Arg Asn Phe Ala Lys Gln Gln
            980                 985                 990
Arg Leu Asn Leu Ser Thr Leu Phe Leu Ala Leu Phe Lys Leu Leu Leu
            995                 1000                1005
His Arg Tyr Ser Gly Gln Ser Glu Leu Ile Ile Gly Met Pro Glu
            1010                1015                1020
Gln Gly Arg Ser Glu Glu Arg Phe Glu Gly Val Val Gly Tyr Phe
            1025                1030                1035
Val Asn Met Leu Pro Ile Arg Ser Arg Gly Val Gly Ser Lys Pro
            1040                1045                1050
Leu Ala Glu Phe Ala Arg Asp Leu Gln Leu Ser Met Ala Asp Ala
            1055                1060                1065
```

-continued

```
Met Asp His Ala Val Tyr Pro Phe Pro Val Met Val Arg Asp Leu
    1070                1075                1080

Gly Arg Ala Pro Ala Glu Asp Leu Ala Pro Ile Phe Gln Val Ala
    1085                1090                1095

Phe Glu Tyr Gln Asn Val Phe Ser Ala Gln Asp Leu Arg Leu Phe
    1100                1105                1110

Asn Gln Ser Tyr Arg Glu Ser Leu Gly Val Thr Phe Leu Glu Glu
    1115                1120                1125

Phe Val Gln Glu Gly Glu Tyr Glu Leu Ala Leu Glu Val Arg Glu
    1130                1135                1140

Gly Glu Ile Asp Phe Ala Leu Asn Leu Lys Phe Asn Pro Thr Leu
    1145                1150                1155

Tyr Arg Met Ala Thr Ile Ala Arg Met Ala Glu His Leu Leu Ile
    1160                1165                1170

Leu Ala Glu His Ala Ile Asp Ala Pro Leu Ser Pro Cys Arg Glu
    1175                1180                1185

Leu Thr Met Leu Ser Glu Arg Glu Arg His Leu Leu His Glu
    1190                1195                1200

Trp Asn Ala Thr Thr Glu Pro Tyr Pro Ser Cys Cys Phe His Gln
    1205                1210                1215

Leu Phe Glu Lys Gln Ala Arg Ala Met Pro Gln Ala Ile Ala Ala
    1220                1225                1230

Ile Phe Gln Glu Gln Arg Leu Ser Tyr Ala Glu Leu Asp Glu Arg
    1235                1240                1245

Ser Glu Arg Leu Ala Ile Tyr Leu Gln Gln Cys Gly Val Gln Pro
    1250                1255                1260

Asn Arg Ile Val Ala Val Cys Leu Glu Arg Ser Leu Asp Met Leu
    1265                1270                1275

Val Ala Leu Ile Gly Ile Ala Arg Ser Gly Ala Ala Trp Leu Pro
    1280                1285                1290

Leu Asp Pro Asn Tyr Pro Asp Arg Leu Arg Phe Met Leu Ser
    1295                1300                1305

Asp Ser Gln Ala Gln Leu Leu Leu Thr Glu Glu Gly Leu Arg Asp
    1310                1315                1320

Lys Thr Ala Ala Ile Val Ser Gln Ala Val Gly Glu Arg Leu Gln
    1325                1330                1335

Ile Val Ala Met Asp Gly His Trp Pro Glu Ile Glu Arg Gln Ala
    1340                1345                1350

Arg Thr Ser Glu Leu Gln Met Arg Asp Asp Pro Arg Asn Leu Ala
    1355                1360                1365

Tyr Val Ile Tyr Thr Ser Gly Ser Thr Gly Ile Pro Lys Gly Val
    1370                1375                1380

Met Ile Glu His Arg Ser Leu Val Asn Phe Leu Tyr Ser Met Leu
    1385                1390                1395

Asn Arg Pro Gly Leu Arg Ala Asn Asp Arg Leu Leu Ala Val Thr
    1400                1405                1410

Thr Tyr Cys Phe Asp Ile Ala Gly Leu Glu Leu Leu Val Pro Leu
    1415                1420                1425

Leu Cys Gly Ala Cys Cys Cys Ile Cys Ala Thr Asp Lys Leu Asn
    1430                1435                1440

Asp Ser Glu Ala Leu Gln Gly Glu Ile Glu Arg Leu Gln Pro Thr
    1445                1450                1455
```

```
Val Met Gln Ala Thr Pro Ser Thr Trp Thr Leu Leu Phe His Gly
1460                1465                1470

Gly Trp Asn Asn Arg Gln Gly Val Lys Ile Leu Cys Gly Gly Glu
    1475                1480                1485

Pro Leu Pro Pro Ala Leu Arg Gln Arg Phe Ala Glu Ser Ala Ser
1490                1495                1500

Gln Thr Trp Asn Leu Phe Gly Pro Thr Glu Thr Thr Ile Trp Ser
1505                1510                1515

Thr Val Ser Arg Leu Asp Leu Thr Lys Asp Ser Val Asp Ile Gly
1520                1525                1530

Thr Pro Ile Ala Asn Thr Arg Val Tyr Ile Leu Asn Gly Asp Asp
1535                1540                1545

Gln Leu Val Pro Ile Gly Val Pro Gly Glu Leu Cys Ile Ala Gly
1550                1555                1560

Asp Gly Leu Ala Arg Gly Tyr Leu Gly Asn Pro Gln Leu Thr Ala
1565                1570                1575

Gln Lys Phe Ile Ala Asn Pro Phe Glu Pro Gly Asn Arg Leu Tyr
1580                1585                1590

Arg Thr Gly Asp Leu Ala Arg Trp Arg Glu Asp Gly Val Leu Glu
1595                1600                1605

His Leu Gly Arg Leu Asp Gln Gln Val Lys Val Arg Gly Tyr Arg
1610                1615                1620

Ile Glu Leu Ser Asp Ile Glu Thr Trp Leu Asn Arg His Pro Ser
1625                1630                1635

Val Ala Gln Ser Leu Val Val Gly His Glu Gln Ala Gly Gly Met
1640                1645                1650

Leu Leu Val Ala Tyr Tyr Val Lys Asp Ser Glu Trp Ala Ser Val
1655                1660                1665

Ser Ser Thr Glu Leu Arg Asn Tyr Leu Ala Glu His Leu Pro Glu
1670                1675                1680

Tyr Met Val Pro Ala Phe Phe Arg Ala Leu Ser Asn Met Pro Leu
1685                1690                1695

Met Pro Asn Gly Lys Val Asp Arg Lys Ala Leu Ser Ala Arg Glu
1700                1705                1710

Leu Val Ala Glu Glu Ser Glu Ser Gly Gly Arg Leu Pro Cys Ser
1715                1720                1725

Asp Ile Glu Arg Glu Val Leu Asp Ile Trp Arg Ser Leu Leu Ala
1730                1735                1740

Val Glu Gly Ile Gly Val Ser Val Gly Phe Phe Glu Val Gly Gly
1745                1750                1755

Asn Ser Ile Leu Ser Val Met Leu Ala Gln Gln Ile Ser Glu Ala
1760                1765                1770

Phe Gly Ile Arg Phe Ala Ala Thr Asp Leu Phe Lys Tyr Pro Thr
1775                1780                1785

Ile Arg Asp Ile Ser Leu Leu Ile Gly Glu Thr Arg Glu Arg Ser
1790                1795                1800

Glu Thr Lys Thr Gly Thr Met Ala Gly Asp Gly Ser Gly Lys Ala
1805                1810                1815

Asp Ser Val Leu Gln Ala Gln Ala Arg Gly Arg Gln Ser Val Thr
1820                1825                1830

Gly Tyr Pro Asp Tyr Tyr Gln Asp Ser Leu Ala Ile Ile Gly Ile
1835                1840                1845

Ser Cys Asn Met Pro Gly Ala Arg Thr Leu Arg Gln Phe Trp Glu
```

```
                1850                1855                1860

Asn Leu Arg Gln Gly Lys Glu Ser Ser Thr Arg Leu Ser Glu Arg
    1865                1870                1875

Glu Leu Arg Arg Ala Gly Val Pro Glu Glu Leu Ile Arg His Pro
    1880                1885                1890

Asp Phe Val Pro Met Gln Tyr Ser Met Glu Gly Lys Glu Leu Phe
    1895                1900                1905

Asp Pro Asp Phe Phe Asn Leu Ser Ala Lys Asn Ala Leu Phe Met
    1910                1915                1920

Asp Pro Gln Tyr Arg Val Leu Leu Gln Gln Ala Trp Gln Ala Ile
    1925                1930                1935

Glu Asp Ala Gly Tyr Val Ala Gln Asp Ile Pro Glu Thr Ala Val
    1940                1945                1950

Phe Met Ser Ala Ser Asn Asn Phe Tyr Lys Thr Leu Leu His Ser
    1955                1960                1965

Ala Gly Ala Val Glu Thr Thr Asp Glu Tyr Ala Ala Trp Ile Ala
    1970                1975                1980

Gly Gln Gly Thr Ile Pro Thr Met Ile Ser Tyr Gln Leu Gly
    1985                1990                1995

Phe Lys Gly Pro Ser Phe Ala Val His Ser Asn Cys Ser Ser Ser
    2000                2005                2010

Leu Val Gly Leu Tyr Leu Ala Ser Gln Cys Leu Arg Leu Lys Glu
    2015                2020                2025

Ala Lys Tyr Ala Leu Val Gly Gly Ala Thr Leu Phe Pro Val Ala
    2030                2035                2040

Gly Thr Gly His Leu Tyr Thr Pro Asp Met Asn Leu Ser Ser Asp
    2045                2050                2055

Gly His Cys Lys Ala Phe Asp Ala Asp Ala Asp Gly Leu Val Gly
    2060                2065                2070

Gly Glu Gly Ala Val Val Leu Met Val Arg Lys Ala Leu Asp Ala
    2075                2080                2085

Ile Arg Asp Gly Asp Pro Ile Tyr Ala Leu Ile Arg Gly Val Ala
    2090                2095                2100

Val Asn Asn Asp Gly Ser Asp Lys Val Gly Phe Tyr Ala Pro Ser
    2105                2110                2115

Val Asn Gly Gln Ala Ala Val Ile Gln Lys Ala Leu Asp Ile Thr
    2120                2125                2130

Gly Val Asp Pro Gln Ser Val Ala Tyr Val Glu Ala His Gly Thr
    2135                2140                2145

Gly Thr Arg Leu Gly Asp Pro Val Glu Ile Met Ala Leu Asn Glu
    2150                2155                2160

Val Tyr Arg Arg Tyr Thr Glu Lys Arg Gln Phe Cys Arg Ile Gly
    2165                2170                2175

Ser Val Lys Pro Asn Ile Gly His Leu Asp Thr Val Ala Gly Leu
    2180                2185                2190

Ala Gly Met Leu Lys Val Val Leu Ser Leu Lys His Ala Glu Phe
    2195                2200                2205

Phe Pro Ser Ile Asn Tyr Arg Glu Pro Asn Pro Ala Ile Asp Phe
    2210                2215                2220

Thr Ser Ser Pro Phe Glu Val Val Thr Gln Leu Thr Pro Trp Pro
    2225                2230                2235

Ala Gly Asn Glu Pro Arg Arg Ala Ala Leu Ser Ser Phe Gly Ile
    2240                2245                2250
```

-continued

```
Gly Gly Thr Asn Thr His Ala Ile Leu Glu Glu Tyr Val Ala Arg
2255                 2260                 2265

Thr Asp Ala Asp Arg Trp Glu Asp Asn Gln Gly Val Pro Leu Pro
2270                 2275                 2280

Glu Gln Val Val Val Leu Ser Ala Lys Thr Gln Asp Arg Leu Gln
2285                 2290                 2295

Ala Ser Val Val Lys Leu Tyr Glu Tyr Leu Leu Arg Ala Gln Ala
2300                 2305                 2310

Thr Thr Glu Gln Leu Asp Leu Gln Asp Leu Ala Tyr Thr Leu Gln
2315                 2320                 2325

Val Gly Arg Gln Ala Met Asp Trp Arg Val Ala Phe Leu Val Lys
2330                 2335                 2340

Asp Leu His Asp Leu Ser Glu Lys Leu Glu Arg Phe Leu Gln Gly
2345                 2350                 2355

Asp Ser Leu Val Gln Asp Cys Phe Gln Gly Arg Val Ala Thr Ser
2360                 2365                 2370

Val Met Asp Ala Ala Ala Thr Pro Leu Pro Val Ala Gln Asp Arg
2375                 2380                 2385

Glu Gln Ala Ala Ile Ala Lys Ala Trp Val Thr Gly Arg Leu Val
2390                 2395                 2400

Asp Trp Lys Glu Leu Pro Arg Arg Gly Thr Pro His Arg Ile Ser
2405                 2410                 2415

Leu Pro Thr Tyr Pro Phe Ala Glu Glu Arg Tyr Trp Val Glu Met
2420                 2425                 2430

Pro Glu Leu Pro Gly Arg Ser Glu Ser Glu Gln Thr Lys Glu
2435                 2440                 2445

Trp Ile Glu Gly Gln Ala Glu Arg Thr Leu Leu Val Val His Pro
2450                 2455                 2460

Leu Trp Gln Ala His Ala Val Val Lys Arg Glu Arg Pro Leu Ile
2465                 2470                 2475

Phe Thr Glu His Leu Val Trp Leu Cys Gly Phe Asp Val Ser Leu
2480                 2485                 2490

Val Arg Ala Leu Thr Arg Cys Leu Pro Glu Gly Tyr Arg Ile Val
2495                 2500                 2505

Ser Leu Thr Pro Glu Gly Arg Gly Val Ala Gln Arg Tyr Gln Ser
2510                 2515                 2520

Leu Cys Leu Gln Met Leu Glu Arg Leu Gln Lys Cys Ile Gly Asp
2525                 2530                 2535

Ala Thr Lys Leu Thr Leu Ile Gln Leu Val Leu Pro Asp Glu Gly
2540                 2545                 2550

Glu Tyr Ser Leu Phe Ser Gly Leu His Ala Leu Leu Lys Thr Val
2555                 2560                 2565

Ser Gln Glu Asn Pro Gln Lys Val Ala Gln Leu Ile Arg Val Ser
2570                 2575                 2580

Ser Gly Glu Thr Ala Arg Ser Leu Ala Asp Lys Leu Ile Glu Asn
2585                 2590                 2595

Thr Phe Ala Pro Asp Asp Ser His Leu Arg Tyr Ala Pro Ser Arg
2600                 2605                 2610

Met Arg Leu Asp Trp Gln Thr Leu Arg Gln Glu Glu Thr Val Leu
2615                 2620                 2625

Asp Met Pro Trp Lys Glu Gly Gly Val Tyr Leu Leu Thr Gly Gly
2630                 2635                 2640
```

```
Ala Gly Gly Leu Gly Val Leu Phe Ala Glu Glu Ile  Ala Arg Arg
    2645                2650                2655

Val Arg Lys Ala Thr Leu Val Leu Val Gln Arg Ser  Pro Leu Ser
    2660                2665                2670

Ala Ala Ala Arg Arg Ala Glu Arg Ile Ala Ala Leu  Arg Ser Asp
    2675                2680                2685

Ser Ile Thr Val Ile Cys Arg Gln Ala Asp Ile Ser  Cys Ala Thr
    2690                2695                2700

Ser Cys Ser Gln Leu Ile Ala Asp Ile Ala Glu Gln  Cys Gly Thr
    2705                2710                2715

Ile Asp Gly Ile Leu His Thr Ala Gly Val Val Arg  Asp Ala Phe
    2720                2725                2730

Ile Leu Asn Lys Ser Ala Ala Glu Phe Gln Glu Val  Leu Ala Ala
    2735                2740                2745

Lys Val Ala Gly Thr Val Asn Leu Asp Arg Ala Thr  Gln Ala Leu
    2750                2755                2760

Gly Leu Asp Phe Phe Leu Leu Phe Ser Ser Ala Ala  Ala Ala Phe
    2765                2770                2775

Gly Asn Ala Gly Gln Ala Asp Tyr Cys Ala Ala Asn  Ala Phe Leu
    2780                2785                2790

Asp Ala Tyr Ala Tyr Glu Arg Asn Gln Arg Val Ala  Ala Gly Gln
    2795                2800                2805

Cys Arg Gly His Thr Leu Ser Val Gly Trp Pro Leu  Trp Arg Asp
    2810                2815                2820

Gly Gly Met Arg Leu Asn Glu Glu Ala Gln Gln Ala  Met Arg Tyr
    2825                2830                2835

Thr Thr Gly Leu Val Pro Met Asp Ser Arg Ser Gly  Ile Arg Gly
    2840                2845                2850

Leu Tyr Arg Ser Leu Ala Ala Arg Leu Gly His Thr  Leu Val Leu
    2855                2860                2865

Glu Gly Asp Ala Thr Ala Ile Gly Ser Leu Leu Ala  Asn Gly Thr
    2870                2875                2880

Ala Arg Ser Val Ser Glu Leu Gly Val Pro Ala Ala  Asn Gly Asn
    2885                2890                2895

Asp Leu Asp Glu Thr Leu Lys Asp Lys Thr Ile Tyr  Gln Leu Lys
    2900                2905                2910

Arg Leu Leu Ala Gln Val Ile Gly Arg Ala Val Glu  Arg Ile Glu
    2915                2920                2925

Ser Cys Glu Pro Met Asp Arg Tyr Gly Leu Asp Ser  Ile Ala Ile
    2930                2935                2940

Thr Gln Leu Asn Arg Lys Leu Glu Glu Gln Phe Gly  Gly Leu Ser
    2945                2950                2955

Lys Thr Leu Phe Tyr Gln Tyr Gln Thr Val Glu Ala  Leu Ala Glu
    2960                2965                2970

Tyr Leu Val Leu Asn Lys Thr Val Ser Cys Arg Ala  Trp Thr Gly
    2975                2980                2985

Leu Arg Asp Glu Ser Val Leu Val Ala Asp Ala Ala  Arg Arg Gly
    2990                2995                3000

Leu Pro Leu Pro Glu Thr Ala Pro Val Val Glu Arg  Asn Val Leu
    3005                3010                3015

Pro Val Gly Asn Ala Val Gln Glu Pro Ile Ala Ile  Ile Gly Leu
    3020                3025                3030

Ser Gly Arg Tyr Pro Gln Ala Glu Thr Leu Glu Glu  Phe Trp Glu
```

-continued

```
                   3035                3040                3045
Asn Leu Gln Ala Gly Lys Asp Cys Val Ser Glu Ile Pro Glu Asp
3050                3055                3060
Arg Trp Arg Leu Glu Asn Phe Phe His Pro Asp Pro Lys Glu Ala
3065                3070                3075
Val Ala Gln Gly Lys Ser Tyr Ser Lys Trp Gly Gly Phe Ile Glu
3080                3085                3090
Gly Phe Ala Glu Phe Asp Pro Leu Phe Phe Asn Ile Ser Pro Arg
3095                3100                3105
Glu Ala Leu Ala Met Asp Pro Gln Glu Arg Leu Phe Leu Gln Cys
3110                3115                3120
Ala Trp His Val Leu Glu Asp Ala Gly Tyr Thr Arg Gln Ser Leu
3125                3130                3135
Gln Gln Gly Gly His Lys Val Gly Val Phe Val Gly Ile Thr Lys
3140                3145                3150
Thr Gly Phe Asp Leu Tyr Gly Pro Glu Leu Trp His Arg Gly Glu
3155                3160                3165
Arg Leu Phe Pro His Thr Ser Phe Ser Ser Val Ala Asn Arg Val
3170                3175                3180
Ser Tyr Cys Leu Asn Leu Lys Gly Pro Ser Met Pro Ile Asp Thr
3185                3190                3195
Met Cys Ser Ser Ser Leu Thr Ala Ile His Glu Ala Cys Gln His
3200                3205                3210
Leu Arg Gln Gly Asp Cys Asp Met Ala Ile Val Gly Gly Val Asn
3215                3220                3225
Met Tyr Val His Pro Ser Thr Tyr Val Gly Leu Cys Ser Ala Tyr
3230                3235                3240
Met Leu Ser Arg Asp Gly Gln Cys Arg Ser Phe Gly Gln Gly Gly
3245                3250                3255
Asn Gly Phe Val Pro Gly Glu Gly Ile Gly Ala Val Leu Leu Lys
3260                3265                3270
Pro Leu Ala Arg Ala Gln Glu Asp Asp Asp Leu Ile His Ala Val
3275                3280                3285
Ile Arg Ser Ser Ser Val Asn His Gly Gly Arg Thr Asn Gly Tyr
3290                3295                3300
Thr Val Pro Asn Pro Asn Ala Gln Ala Glu Leu Ile Gly Asp Cys
3305                3310                3315
Leu Lys Lys Ala Gly Val Asp Ala Arg Ser Ile Gly Tyr Ile Glu
3320                3325                3330
Ala His Gly Thr Gly Thr Glu Leu Gly Asp Pro Ile Glu Val Asn
3335                3340                3345
Gly Leu Ala Gln Ala Phe Gly Gln Glu Ala Gly Glu His Ser Arg
3350                3355                3360
Cys Phe Leu Gly Ser Val Lys Ser Asn Leu Gly His Leu Glu Ala
3365                3370                3375
Ala Ala Gly Met Ala Gly Leu Thr Lys Val Ile Leu Gln Met Arg
3380                3385                3390
His Gly Gln Ile Val Pro Ser Leu His Ala Gln Val Leu Asn Pro
3395                3400                3405
Asn Ile Asp Phe Ala Ala Thr Pro Phe Thr Val Pro Gln Gln Leu
3410                3415                3420
Val Glu Trp Arg Arg Thr Ile Leu Gln Glu Ser Gly Arg Ser Arg
3425                3430                3435
```

-continued

Glu Leu Pro Arg Arg Ala Gly Leu Ser Ser Phe Gly Ala Gly Gly
3440                3445                3450

Ser Asn Ala His Leu Ile Leu Glu Glu Tyr Ile Ala Pro Glu Pro
3455                3460                3465

Ala Gln Arg Pro Arg Phe Gly Glu Pro Gly Thr Ala Ala Val Ile
3470                3475                3480

Leu Leu Ser Ala Lys Thr Pro Glu Cys Leu Arg Arg Val Val Ser
3485                3490                3495

Asp Leu Leu Ala Phe Ile Glu Ser Glu Leu Thr Arg Thr Val Asp
3500                3505                3510

Pro Asp Gln Thr Leu Phe Asp Ile Ala Tyr Thr Leu Gln Val Gly
3515                3520                3525

Arg Glu Ala Leu Asp Glu Arg Leu Gly Leu Val Ala Val Ser Leu
3530                3535                3540

Gln Glu Leu Ser Arg Gln Leu Ala Ala Phe Leu Gly Glu Glu Ala
3545                3550                3555

Glu Gln Pro Leu Leu Tyr Arg Gly Arg Val Gln Arg Asn Lys Asp
3560                3565                3570

Ala Leu Gln Ala Leu Ala Asn Asp Glu Glu Phe Gln Glu Thr Val
3575                3580                3585

Asp Lys Trp Leu Ala Arg Arg Lys Tyr Ser Lys Leu Leu Lys Phe
3590                3595                3600

Trp Val Thr Gly Leu Ser Val Asp Trp Thr Arg Leu Tyr Ser Asp
3605                3610                3615

Val Leu Pro Arg Arg Ile Arg Leu Pro Val Tyr Pro Phe Val Arg
3620                3625                3630

Gln Arg Tyr Trp Leu Asp Ala Tyr Ser Leu Glu Pro Met Val Pro
3635                3640                3645

Thr Glu Gln Pro Ser Val Val Pro Val Asp Ala Glu Val Ser Gly
3650                3655                3660

Ser Asp Ala Gly Arg Glu Ala Asp Leu Met Met Leu Gly Pro Val
3665                3670                3675

Trp Asp Ala Val Val Glu Gln Gly Thr Glu Asp Phe Pro Pro Ala
3680                3685                3690

Gly Ala Arg Ile Ala Met Val Gly Gly Ser Glu Ala Gln Lys Arg
3695                3700                3705

Ala Val Phe Glu Gln Tyr Pro Lys Ala Leu Glu Leu Ala Ala Gly
3710                3715                3720

Ala Val Gly Ala Ala Ser Ile Ala Arg Leu Gly Arg Leu Asp His
3725                3730                3735

Val Val Trp Phe Ala Pro Ala Ser Gln Thr Gln Gly Met Ala Asp
3740                3745                3750

Glu Arg Ile Ile Asp Ala Gln Arg Asp Gly Val Leu Ala Leu Phe
3755                3760                3765

Gln Leu Val Lys Val Leu Leu Ala Glu Gly Tyr Gly Val Ala Glu
3770                3775                3780

Phe Gly Met Thr Val Ile Thr Thr Gln Ala Leu Ala Thr Cys Asp
3785                3790                3795

Thr Glu Arg Ile Asp Pro Thr His Ala Ala Val His Gly Leu Val
3800                3805                3810

Gly Ser Leu Ala Lys Glu Tyr Pro Lys Trp Arg Leu Arg Ala Leu
3815                3820                3825

```
Asp Ile Asp Ala Arg Ala Glu Trp Pro Val Pro Gly Leu Trp Arg
3830            3835                3840

Leu Leu Pro His Thr Arg Gly Glu Ser Arg Val Trp Arg Gly Cys
3845            3850                3855

Glu Trp Leu Arg Gln Arg Leu Val Ala Leu Asn Gly Met Pro Val
3860            3865                3870

Ala Lys Gly Arg Ala Tyr Arg Arg Gln Gly Val Tyr Val Val Ile
3875            3880                3885

Gly Gly Ala Gly Gly Leu Gly Met Thr Trp Ser Arg Met Met Ile
3890            3895                3900

Arg Asp His Gln Ala Gln Ile Val Trp Leu Gly Arg Ser Ala Lys
3905            3910                3915

Asp Ala Thr Val Arg Ala Lys Leu Asp Glu Val Ala Asp Asp Gly
3920            3925                3930

Leu Ala Pro Asp Tyr Trp Gln Ile Asp Ala Arg Asp Ala Asp Ala
3935            3940                3945

Leu Arg Gln Thr Phe Arg Gln Val Arg Glu Arg Tyr Gly Gln Ile
3950            3955                3960

His Gly Val Ile Val Ser Thr Leu Gly Asp Tyr Asp Gln Ser Val
3965            3970                3975

Ala Gln Met Ser Glu Ala Leu Phe Arg Glu Ile Leu Ser Ser Lys
3980            3985                3990

Leu Asp Ile Gly Val Arg Leu Ser Gln Cys Leu Arg Asp Glu Ala
3995            4000                4005

Leu Asp Phe Val Val Phe Phe Ser Ser Met Val Ala Phe Gly Arg
4010            4015                4020

Ser Gly Gly Met Ala Ala Tyr Ser Ala Ala Cys Ala Phe Asn Asp
4025            4030                4035

Thr Phe Ala Arg Gln Leu Gly Asn Glu Leu Ala Cys Ala Val Lys
4040            4045                4050

Val Ile Asn Trp Gly Tyr Trp Asn Leu Gly Gly Gly Thr Arg Ile
4055            4060                4065

Ser Ala Ala Leu Lys Arg Leu Val Glu Gln Arg Gly Val Arg Pro
4070            4075                4080

Ile Glu Ala Arg Glu Gly Leu Cys Ala Leu Ala Val Leu Leu Asp
4085            4090                4095

Gly Pro Leu Arg Gln Leu Ala Val Thr Arg Thr Cys Gln Pro Ala
4100            4105                4110

Ala Ile Glu Thr Phe Glu Ala Gly Gln Trp Leu Thr Val Lys Ala
4115            4120                4125

Gly Thr His Ser Cys Phe Ala Asn Val Glu Ala Tyr Gln Pro Thr
4130            4135                4140

Gln Pro Met Pro Gln Glu Ser Pro Asp Ala Ala Arg Leu Asn Leu
4145            4150                4155

Trp Ile Val Arg Leu Leu Phe Val Gln Leu Gln Ser Leu Gly Leu
4160            4165                4170

Phe Gln Glu Thr Gly Phe Gln Asn Ala Thr Ala Ile Arg Arg Gln
4175            4180                4185

Ala Gly Ile Val Asp Lys Tyr Glu Arg Trp Trp Arg Glu Ser Leu
4190            4195                4200

Asn Ile Leu Ala Glu His Gly Tyr Leu Arg Leu Ala Gly Asp Glu
4205            4210                4215

Val Ala Arg Ile Ala Ser Ala Asp Glu Ile Gly Glu Ser Ser Arg
```

```
                      4220                4225               4230
Glu Arg Leu Trp Gln Glu Trp Arg Glu Cys Lys Thr Arg Phe Leu
    4235                4240               4245
Glu Gln Pro Gln Thr His Thr Leu Ala Val Leu Val Glu Asp Cys
    4250                4255               4260
Leu Ser Gln Leu Pro Glu Val Leu Arg Gly Thr Arg Leu Val Thr
    4265                4270               4275
Asp Ile Leu Phe Pro Asn Gly Ser Met Glu Lys Ile Glu Gly Leu
    4280                4285               4290
Tyr Lys Asn Asn Leu Ile Cys Asp Tyr Phe Asn Asp Val Val Ala
    4295                4300               4305
Gly Val Ala Gln Ala Tyr Ile Gln Arg Arg Leu Glu Asn Glu Pro
    4310                4315               4320
Asn Ala Glu Ile Arg Leu Leu Glu Val Gly Ala Gly Thr Gly Gly
    4325                4330               4335
Thr Thr Ser Thr Val Leu Pro Gln Leu Asn Leu Trp Arg Ala Phe
    4340                4345               4350
Ile Ala Glu Tyr Ala Tyr Thr Asp Leu Ser Lys Ser Phe Phe Asn
    4355                4360               4365
His Ala Arg Leu Arg Tyr Gly Thr Asp Tyr Pro Tyr Ile Thr Tyr
    4370                4375               4380
Arg Leu Leu Asn Ile Glu Glu Pro Leu Ile Gln Gln Asp Ile Glu
    4385                4390               4395
Ile Gly Thr Tyr Asp Ile Leu Ile Ala Thr Asn Val Leu His Ala
    4400                4405               4410
Thr Arg Asn Met Arg Asn Thr Leu Arg Asn Ala Lys Ala Ala Leu
    4415                4420               4425
Arg Gly Asn Gly Ile Leu Ile Leu Asn Glu Ile Ser Asp Lys Thr
    4430                4435               4440
Ile Phe Ala Ser Val Leu Phe Gly Leu Ile Asp Gly Trp Ser Leu
    4445                4450               4455
Ala Glu Asp Glu His Trp Arg Ile Pro Gly Ser Pro Gly Leu Phe
    4460                4465               4470
Ala Glu Asn Trp Gln Ala Leu Leu Leu Gln Glu Gly Phe Asp Lys
    4475                4480               4485
Val Ser Phe Pro Ala Gln Val Ala His Asp Leu Gly Gln Gln Ile
    4490                4495               4500
Ile Val Ala Gln Thr Asn Gly Val Ile His Gln His Gly Ala Gly
    4505                4510               4515
Pro Val Leu Glu Thr Ala Val Ala Asp Lys Pro Leu Pro Thr Leu
    4520                4525               4530
Glu Ser Ala Val Ala Ala Glu Arg Leu Val Asp Arg Ser Ser Val
    4535                4540               4545
Pro Ala Arg Arg Gln Asp Val Ala Ala Arg Val Arg Glu Leu Ile
    4550                4555               4560
Leu Asp Ser Leu Ala Gln Ala Leu Ser Ile Gly Arg Glu Gln Ile
    4565                4570               4575
Glu Gln Asp Ile Pro Phe Ser Asp Tyr Gly Ile Asp Ser Ile Leu
    4580                4585               4590
Gly Val Gly Phe Val Gln Arg Leu Asn Asp Glu Leu Gly Leu Ser
    4595                4600               4605
Leu Asn Thr Thr Leu Leu Phe Asp Tyr Thr Thr Val Gln Arg Leu
    4610                4615               4620
```

-continued

```
Ala Glu His Ile Val Ala Glu Tyr Gly His Thr Leu Asp Val Pro
    4625                4630                4635

Ala Ala Leu Pro Gly Pro Glu Leu Ser Val Ser Glu Pro Ala Met
    4640                4645                4650

Asp Ile Pro Leu Pro Ala Val Gln Ala Val Pro Ser Ser Leu Pro
    4655                4660                4665

Arg Arg Glu Ala Val Val Gln Thr Asp Gly Ile Ala Val Ile Gly
    4670                4675                4680

Met Ala Gly Gln Phe Pro Gly Ala Asp Ser Val Asp Ala Leu Trp
    4685                4690                4695

Gln Asn Met Val Ala Gly Val Asn Pro Val Thr Glu Leu Ser Glu
    4700                4705                4710

Leu Tyr Leu Pro Tyr His Ala Tyr Ser Pro Glu Lys Gln Pro Gly
    4715                4720                4725

Lys Ser Tyr Cys Lys Trp Gly Gly Ala Leu Gln Gly Arg Asp Cys
    4730                4735                4740

Phe Asp Pro Leu Phe Phe Asn Ile Ser Pro Arg Glu Ala Glu Ser
    4745                4750                4755

Met Asn Pro His Gln Arg Leu Ile Leu Gln Glu Ser Trp Lys Ala
    4760                4765                4770

Leu Glu Asp Ala Gly Tyr Ala Pro Arg Ser Leu Ser Asp Ser Arg
    4775                4780                4785

Thr Gly Ile Phe Val Gly Ala Glu Pro Ser Ala Tyr Val His Glu
    4790                4795                4800

Ser Phe Val Gly Ala Ser Asp Ala Ile Val Ala Ser Arg Leu Ser
    4805                4810                4815

Tyr Phe Leu Asp Leu Lys Gly Pro Ala Phe Val Asn Thr Gly
    4820                4825                4830

Cys Ser Ser Ser Gly Val Ala Leu His Leu Ala Cys Glu Ser Leu
    4835                4840                4845

Arg Asn Gly Glu Thr Glu Val Ala Leu Ala Gly Gly Val Phe Ala
    4850                4855                4860

Val Met Gly Gln Thr Ile Leu Val Gly Leu Ala Gln Thr Asp Met
    4865                4870                4875

Leu Ser Arg Thr Gly Cys Cys Cys Thr Phe Asp Ala Asp Ala Asp
    4880                4885                4890

Gly Met Val Met Ser Glu Gly Val Gly Met Val Val Leu Lys Arg
    4895                4900                4905

Leu Asp Gln Ala Leu Ser Asp Gly Asp Thr Ile Tyr Gly Val Ile
    4910                4915                4920

Arg Ala Ser Gly Ile Asn Gln Asp Gly Ala Ser Asn Gly Ile Thr
    4925                4930                4935

Ala Pro Ser Gly Ile Ala Gln Gln Gln Leu Ile Thr Asp Val Tyr
    4940                4945                4950

Arg Arg Tyr Ala Ile Asp Pro Arg Arg Ile Thr Tyr Val Glu Ala
    4955                4960                4965

His Gly Thr Gly Thr Arg Leu Gly Asp Pro Val Glu Ala Asn Ala
    4970                4975                4980

Leu Val Arg Ala Phe Arg Ser Phe Thr Glu Ser Thr Gly Tyr Cys
    4985                4990                4995

Ala Val Gly Ser Ile Lys Ser His Ile Gly His Thr Ser Ser Ser
    5000                5005                5010
```

-continued

```
Ser Gly Val Ile Gly Leu Ile Ser Ile Leu Leu Cys Leu Lys His
5015                5020                5025

His Gln Leu Pro Gly Met Arg His Phe Lys Arg Leu Asn Pro Leu
5030                5035                5040

Ile Glu Phe Glu Arg Ser Pro Phe Tyr Val Asn Ala Arg Met Met
5045                5050                5055

Pro Trp Arg Ser Gly Ser Gly Glu Pro Leu Met Ala Ala Leu Asn
5060                5065                5070

Ser Phe Gly His Ser Gly Thr Asn Val His Leu Val Val Glu Glu
5075                5080                5085

Phe Val Arg Ser Asn Ser Glu Asp Pro Arg Val Leu Asp Asp Val
5090                5095                5100

Ser Ser Thr Ala Gln Pro Glu Leu Ile Leu Leu Ser Thr Lys Asp
5105                5110                5115

Ala Glu Arg Leu Ser Glu Val Leu Asn Asn Leu Ala His Phe Val
5120                5125                5130

Arg Gln Ala Gln Asn Gln Pro Ala Asp Leu Glu Arg Leu Ser Leu
5135                5140                5145

Ala Asp Leu Ala Tyr Thr Leu Gln Thr Gly Arg Glu Ala Met Glu
5150                5155                5160

Gln Arg Val Ala Leu Leu Val Gly Asp Leu Ala Gly Leu Leu Glu
5165                5170                5175

Ala Leu Ser Ala Leu Arg Glu Glu Arg Pro Cys Pro Val Ser Val
5180                5185                5190

Trp Ser Gly Arg Val Glu Pro Gly Pro Ser Arg Gly Ala Glu Thr
5195                5200                5205

Val Asn Ala Asp Gln Pro Ala Ala Glu Leu Leu Gln Arg Ile Pro
5210                5215                5220

Gln Trp Leu Ala Glu Gly Ala Leu Asp Glu Leu Ala Gln Ala Trp
5225                5230                5235

Val Ala Gly Ala Pro Ile Asp Trp Cys Gln Leu Arg Arg Arg Arg
5240                5245                5250

Pro Pro Arg Arg Val His Leu Pro Ser Tyr Pro Phe Ala Arg Glu
5255                5260                5265

Arg Tyr Trp Arg Ser Glu Pro Ala Val His Ser Pro Val Val Ala
5270                5275                5280

Ala Gly Leu His Pro Leu Val Gln Arg Asn Thr Ser Thr Leu Asp
5285                5290                5295

Arg His Cys Phe Glu Ser Ser Phe Asp Gly Ser Glu Phe Phe Phe
5300                5305                5310

Arg Asp His Arg Val Gln Gly Gln Pro Leu Leu Pro Ala Val Ala
5315                5320                5325

Tyr Leu Glu Trp Ala Arg Ala Ala Ala Gln Ile Ala Leu Gly Asn
5330                5335                5340

Ala Cys Pro Asp Val Ala Leu Lys Leu Ser Asn Val Val Trp Ile
5345                5350                5355

Gly Pro Leu Leu Ala Glu Gln Pro Ile Val Gly Thr Ile Thr Leu
5360                5365                5370

Gln Ala Arg Glu Asp Arg Gly Ile Asp Tyr Gln Ile Ser Ser Val
5375                5380                5385

Ser Ala Ala Gly Gln Gln Pro Val Val His Cys Gln Gly Ile Ala
5390                5395                5400

Thr Thr Glu Thr Glu Lys Glu Ala Ala Pro Val Leu Asp Leu Asp
```

-continued

```
            5405                5410                5415

Ala Leu Arg Ser Arg Leu Thr Gln Lys Glu Ile Gly Val Glu Arg
    5420                5425                5430

Cys Tyr Ala Ala Leu Glu Ala Ala Gly Val Asn His Gly Pro Ala
    5435                5440                5445

Met Arg Gly Leu Gln Ala Val Ser Arg Asn Ala Glu Glu Val Leu
    5450                5455                5460

Ala Thr Leu Arg Leu Pro Ala Glu Thr Val Gly Glu Ala Ser Ala
    5465                5470                5475

Tyr Val Leu His Pro Ala Ile Leu Asp Ala Ala Leu Gln Ala Ser
    5480                5485                5490

Ile Ala Leu Thr Leu Arg Asp Asp Glu Val Glu Pro Ser Pro Glu
    5495                5500                5505

Thr Ser Pro Arg Pro Val Leu Leu Pro Phe Ala Leu Glu Ser Leu
    5510                5515                5520

Arg Val Tyr Ala Pro Cys Cys Ala Ser Met Trp Ala Trp Ile Arg
    5525                5530                5535

Leu Val Ala Val Glu His Ala Gly Gln Ala Leu Gln Arg Leu Asp
    5540                5545                5550

Val Asp Ile Cys Thr Lys Glu Gly Glu Val Cys Val Ala Leu Arg
    5555                5560                5565

Gly Phe Thr Ser Arg Ser Leu Pro Pro Ser Gly Ala Thr Glu Ser
    5570                5575                5580

Arg Ala Ser Ala Ser Ala Ala Ser Ser Thr Leu Val Ser Thr Glu
    5585                5590                5595

Gly Val Ser Arg Phe Lys Gly Glu Glu Phe Phe Leu Arg Asp His
    5600                5605                5610

Ser Gly Met Leu Pro Ala Ala Val Tyr Leu Glu Met Val Arg Ala
    5615                5620                5625

Phe Ala Glu Gly Lys His Glu Arg Lys Ile Thr Gly Leu Ser His
    5630                5635                5640

Val Val Trp Pro Lys Val Leu Leu Val Ser Gly Glu Gly Arg Glu
    5645                5650                5655

Val Arg Thr Cys Leu Thr Asn Val Asp Arg Ser Ala Phe Leu Ile
    5660                5665                5670

Ser Ala Cys Glu Gln Ser Ser Glu Gly Pro Gln Glu Val Thr Tyr
    5675                5680                5685

Cys Gln Gly Asn Leu Leu Pro Glu Val Met Glu Glu Pro Gly
    5690                5695                5700

Ala Ala Leu Ala Ile Glu Ala Ile Ala Tyr Arg Cys Pro Ser Val
    5705                5710                5715

Leu Glu Ala Lys Gln Cys Asp Arg Leu Leu Gln Ser Thr His Gly
    5720                5725                5730

Pro Ala Leu Met Ser Val Gln Gln Leu Arg Tyr Ser Asp Arg Glu
    5735                5740                5745

Ala Leu Ala Leu Leu Gln Leu Pro Asp Glu Leu Gln Met Gly Trp
    5750                5755                5760

Asp Asp Tyr Gly Trp His Pro Ser Leu Leu Asn Gly Ala Ile Leu
    5765                5770                5775

Ala Ser Val Val Trp Cys Leu Ala Arg Ala Pro Arg Ser Arg Ala
    5780                5785                5790

Gly Leu Pro Met Pro Phe Ser Leu Asp Arg Leu Arg Val Phe Gln
    5795                5800                5805
```

```
Pro Phe Glu Arg Gln Met Gln Ala Tyr Val Arg Arg His Gly Ser
    5810            5815                5820

Ala Arg Ser Leu Gly Glu Asn Leu Glu Lys Val Asp Ile Asp Leu
    5825            5830                5835

Leu Asp Ser Gln Gly Arg Cys Leu Ala Ser Leu Glu Gly Phe Thr
    5840            5845                5850

Leu Val Phe Ala Pro Asp Ala Asn Arg Leu Val Tyr Ala Ile Pro
    5855            5860                5865

Gln Trp Val Glu Gln Ala Leu Pro Ala Arg Val Ala Ala Ser Ala
    5870            5875                5880

Pro Leu Ala Val Gln Ala Pro Val Phe Ile Leu Ala Gly Ala Gly
    5885            5890                5895

Glu Pro Leu Arg Arg Ala Leu His Asp Ser Trp Pro Asp Ala Leu
    5900            5905                5910

Leu His Glu Leu Pro Glu Ser Ala Phe Glu Val Gly Asp Gly Leu
    5915            5920                5925

Arg Gln Ala Val Val Glu Val Phe Gly Trp Cys Arg Arg Leu Leu
    5930            5935                5940

Pro Tyr Lys Gly Ala Ala Leu Gln Pro Leu Leu Val Leu Leu Pro
    5945            5950                5955

Glu Ala Glu Arg Glu Val Thr Pro Gln Ala Leu Leu Gly Gly Ala
    5960            5965                5970

Leu Ser Gly Leu Leu Lys Thr Val Arg Leu Glu His Pro Arg Ile
    5975            5980                5985

Thr Ala Arg Ile Ile Ser Tyr Pro Val Asp Asp Thr Val Thr Ala
    5990            5995                6000

Gly Trp Met Lys Val Leu Ala Ala Glu Ile Ala Ser Pro Glu Gly
    6005            6010                6015

Asp Val Glu Ile Arg Tyr Asp Arg Gln Ala Arg Arg His Ile Lys
    6020            6025                6030

Val Leu His Glu Ile Thr Leu Ser Ala Gly Glu His Gly Asp Ser
    6035            6040                6045

Leu Phe Arg Pro Asp Asp Val Val Trp Leu Thr Gly Gly Leu Gly
    6050            6055                6060

Gly Ile Gly Arg Gln Ile Ala Arg Tyr Leu Gly Val Glu Arg Arg
    6065            6070                6075

Val Arg Leu Ala Leu Ser Gly Arg Ser Ala Ile Asp Asp Lys Gly
    6080            6085                6090

Glu Arg Phe Leu Gln Glu Leu Arg Arg Glu Gly Ala Val Val Ser
    6095            6100                6105

Tyr Leu Arg Val Asp Val Ala Asp Ala Asp Ala Val Gly Arg Ala
    6110            6115                6120

Leu Leu Ala Ile Glu Gln Glu His Gly Gly Leu Thr Gly Ile Ile
    6125            6130                6135

His Ser Ala Gly Ile Ile Ala Asp Asp Tyr Leu Asn Ser Lys Thr
    6140            6145                6150

Thr Ala Gln Phe Glu Gln Val Leu Lys Pro Lys Val Ser Gly Val
    6155            6160                6165

Val Asn Leu Asp Ala Ala Thr Ala Asn Arg Ser Leu Arg Tyr Leu
    6170            6175                6180

Leu Val Phe Ser Ser Ile Ala Gly Val Leu Gly Asn Met Gly Gln
    6185            6190                6195
```

```
Ala Asp Tyr Ala Ala Ala Asn Gly Phe Leu Asp Ser Phe Ala His
    6200            6205                6210

Tyr Arg Glu Ala Leu Val Arg Gln Gly Leu Arg Ser Gly Lys Ser
    6215            6220                6225

Leu Ser Leu Asn Trp Pro Leu Trp Arg Glu Gly Met Gln Met
    6230            6235                6240

Gly Arg His Gly Glu Ala Leu Met Gln Gln Ala Thr Gly Met Leu
    6245            6250                6255

Ala Met Glu Ser Ala Gln Gly Phe Glu Ala Leu Glu Ala Gly Leu
    6260            6265                6270

Arg Ser Ala Gln Ala Gln Ile Leu Val Ala Phe Gly Glu Pro Val
    6275            6280                6285

Ser Ile Arg Asn Arg Leu Leu Thr Phe Arg Met Asp Ala Pro Glu
    6290            6295                6300

Pro Pro Ala Pro Ser Val Val Glu Met Asp Arg Ala Pro Gly Glu
    6305            6310                6315

Glu Val Gly Glu Gln Glu Thr Gln Gln Leu Val Arg Ser Val Glu
    6320            6325                6330

Ala Glu Leu Ile Arg Ile Val Ala Phe Val Gln Arg Ile Pro Ala
    6335            6340                6345

Glu Lys Ile Asn Val Arg Arg Asp Ile Ser Ala Tyr Gly Phe Asp
    6350            6355                6360

Ser Ile Ser Phe Thr Glu Phe Ala Asn Ala Leu Asn Lys Ala Tyr
    6365            6370                6375

Lys Leu Ser Leu Met Pro Thr Leu Phe Phe Glu Ile Ala Ser Leu
    6380            6385                6390

Ala Asp Leu Ala Gly His Leu Leu Thr Gln His Arg Pro Ala Leu
    6395            6400                6405

Leu Glu Lys His Ala Val Asp Val Glu Lys Pro Ser Glu Cys His
    6410            6415                6420

Ser Gly Val Ala Ala Gln Ile Pro Ile Pro Thr Met Pro Lys Ser
    6425            6430                6435

Glu Cys Ile Ala Thr Leu Pro Leu Leu Pro Val Gly Ser Ile Glu
    6440            6445                6450

Pro Glu Pro Gln Ala Asp Leu Glu Ala Val Ala Val Ile Gly Met
    6455            6460                6465

Ala Gly Lys Phe Pro Gly Cys Glu Asp Leu Glu Asp Phe Trp Thr
    6470            6475                6480

Cys Leu Gln Ser Cys Gln Asp Leu Ile Ser Glu Val Pro Glu Gln
    6485            6490                6495

Arg Trp Asp Trp Arg Arg Phe Tyr Gly Asp Pro His Gln Glu Pro
    6500            6505                6510

Gly Lys Thr Lys Ile Lys Trp Gly Gly Phe Val Ala Asp Ala Asp
    6515            6520                6525

Cys Phe Asp Ala Arg Phe Phe Gly Ile Ser Pro Val Glu Ala Glu
    6530            6535                6540

Val Met Asp Pro Gln Leu Arg Leu Phe Leu Glu Thr Val Trp Ala
    6545            6550                6555

Ala Leu Glu Asp Ala Gly Tyr Pro Ala Gly Arg Leu Ala Gly Ser
    6560            6565                6570

Arg Thr Gly Val Phe Ala Gly Val Ala Thr Ala Asp Tyr Lys Asp
    6575            6580                6585

Leu Leu Ile Glu Ala Arg Ala Arg Gly Leu Val Gln Thr Pro Ser
```

-continued

```
            6590                6595                6600
Glu Pro Phe Pro Phe Met Ile Ala Asn Arg Ile Ser Tyr Trp Phe
    6605                6610                6615
Asn Phe Asn Gly Pro Ser Glu Ala Ile Asp Thr Ala Cys Ser Ser
    6620                6625                6630
Ser Leu Ile Ala Val His Lys Ala Ile Glu Ser Leu Arg Leu Gly
    6635                6640                6645
Ser Cys Glu Met Ala Leu Ala Gly Gly Val Asn Val Leu Gly Ser
    6650                6655                6660
Pro Arg Ile Thr Ile Ala Ser Ser Gln Ala Gly Met Leu Ser Glu
    6665                6670                6675
Asp Gly Arg Cys Met Thr Phe Asp Glu Arg Ala Asn Gly Tyr Val
    6680                6685                6690
Arg Ser Glu Gly Val Ala Ile Leu Leu Leu Lys Pro Leu Arg Lys
    6695                6700                6705
Ala Ile Ala Asp Asn Asp Arg Ile His Gly Leu Ile Arg Gly Ser
    6710                6715                6720
Gly Glu Asn His Gly Gly Arg Ser Ala Ser Pro Thr Ala Pro Asn
    6725                6730                6735
Gly Asn Ala Gln Lys Arg Leu Leu Val Asp Ile Tyr Ser Arg Ala
    6740                6745                6750
Asp Ile Asp Pro Arg Thr Ile Ser Tyr Ile Glu Ala His Gly Thr
    6755                6760                6765
Gly Thr Val Leu Gly Asp Pro Val Glu Val Asn Gly Leu Lys Ala
    6770                6775                6780
Ala Phe Gln Glu Leu Tyr Gln Ser Arg Gly Leu Asp Val Pro Glu
    6785                6790                6795
Gln Pro His Cys Gly Leu Asn Ser Val Lys Ala Asn Val Gly His
    6800                6805                6810
Leu Glu Ala Ala Ala Gly Ala Val Gly Ile Val Lys Val Leu Leu
    6815                6820                6825
Met Leu Lys His Arg Lys Ile Pro Gly Asn Pro His Leu Arg Arg
    6830                6835                6840
Pro Asn Pro Tyr Leu Gln Leu Glu Gly Thr Pro Phe Tyr Leu Val
    6845                6850                6855
Arg Glu Thr Leu Asp Trp Pro Gln Pro Thr Asp Val Arg Gly Asn
    6860                6865                6870
Pro Leu Ala Arg Arg Ala Gly Val Ser Ser Phe Gly Val Gly Gly
    6875                6880                6885
Ser Asn Ala His Val Ile Leu Glu Glu Tyr Gln Glu Pro Glu Arg
    6890                6895                6900
Gln Gly Trp Gly Ser Glu Pro Ala Tyr Pro Ala Leu Ile Val Leu
    6905                6910                6915
Ser Ala Lys Asp Glu Glu Arg Leu Val Cys Val Ala Gln Arg Leu
    6920                6925                6930
Leu Arg Phe Ile Arg Asp Tyr Gly Ser Glu Leu Tyr Leu His Asp
    6935                6940                6945
Ile Ala Tyr Thr Leu Gln Val Gly Arg Glu Ala Met Pro Arg Arg
    6950                6955                6960
Leu Ala Leu Ala Val Thr Ser Leu Ala Gln Leu Ala Asp Arg Leu
    6965                6970                6975
Gln Thr Trp Leu Glu Gln Pro Thr Gln Thr Glu Gly Val Gln Gln
    6980                6985                6990
```

```
-continued

Gly Leu Val Thr Gln Glu Ala Glu Glu Gln Phe Asp Thr Val Leu
    6995                7000                7005

Gly Asp Glu Asp Arg Ala Ala Val Glu Arg Trp Val Glu Lys
    7010                7015                7020

Gly Gln Tyr Glu Lys Leu Leu Asp Ala Trp Thr Arg Gly Trp Ala
    7025                7030                7035

Ile Asp Trp Asn Val Leu Tyr Cys Thr Asp Thr Arg Pro Arg Arg
    7040                7045                7050

Ile Gly Leu Pro Thr Tyr Pro Phe Ala Arg Arg Tyr Trp Val
    7055                7060                7065

Ala Ser Val Pro Gln Ala Glu Asp Arg Gly Asn Ser Thr Leu Ser
    7070                7075                7080

Glu Pro Glu Pro Glu Gln Arg Ser Ala Lys Ser Asp Leu Leu Thr
    7085                7090                7095

Phe Glu Glu Tyr Trp Ala Glu Val Pro Leu Ala Ala Pro Ala Thr
    7100                7105                7110

Asp Arg Val Lys Thr Leu Leu Cys Leu Cys Ser Asp Pro Glu His
    7115                7120                7125

Gln Arg Arg Ile Ala Glu Gln Xaa Asp Ser Arg Asp Pro Gly Val
    7130                7135                7140

Gln Leu Ile Phe Ile Glu Gln Gly Asp Ala Pro Ala Glu Pro Asp
    7145                7150                7155

Glu Ala Arg Gln Arg Ile Asp Pro Leu Gln Pro Ser Ser Tyr Ser
    7160                7165                7170

Arg Ala Leu Thr Thr Ile Ala Lys Ala Leu Gly Arg Val Asp Ala
    7175                7180                7185

Leu Leu Tyr Leu Trp Pro Cys Glu Asp Arg Arg Trp Ile Ser Asn
    7190                7195                7200

Val Leu Pro Val Leu His Leu Leu Gln Ala Leu Tyr Glu Thr Gly
    7205                7210                7215

Leu Arg Pro Arg Lys Leu Leu Leu Ser Gly Glu Tyr Ala Asp Ala
    7220                7225                7230

Leu Glu Arg Cys His Leu Asp Ser Trp Val Ala Phe Glu Arg Ser
    7235                7240                7245

Leu Gly Val Val Met Pro Glu Thr Gln Val Ala Val Phe Arg
    7250                7255                7260

Glu Arg Ala Ala Asp Thr Gly Glu Ser Ser Pro Thr Trp Asp Trp
    7265                7270                7275

Leu Glu Val Leu Val Ala Glu Leu Phe Ala Glu Lys Leu Arg Ser
    7280                7285                7290

Ala Cys Tyr Arg Gln Gly Val Arg His Val Pro Leu Ile Arg Pro
    7295                7300                7305

Leu Ala Trp Gln Pro Gly Ser Ala Ser Pro Phe Lys Gln Gly Gly
    7310                7315                7320

Val Tyr Leu Ile Thr Gly Gly Gly Gly Leu Gly Met Ile Val
    7325                7330                7335

Ala Glu His Leu Ala Thr Val Tyr Ala Ala Arg Leu Val Leu Ser
    7340                7345                7350

Gly Arg Ser Ser Ser Leu Ala Ala Glu Lys Tyr Glu Leu Leu Gln
    7355                7360                7365

Ala Arg Gly Ala Gln Val Leu Tyr Val Gly Ala Asp Val Thr Asp
    7370                7375                7380
```

```
Val His Ala Met Gln Glu Val Val Asp Gln Ala Arg Arg His Phe
7385                7390                7395

Ser Pro Leu Asn Gly Val Leu His Ile Ala Gly Leu Asn Gly Thr
7400                7405                7410

Ala Glu Val Leu Lys Ala Glu Ala Asp Ala Phe Gln Arg Val Leu
7415                7420                7425

Asp Ala Lys Ile Thr Gly Ser Gln Val Leu Asp Gln Val Leu Arg
7430                7435                7440

Arg Glu Ser Leu Asp Phe Ile Cys Tyr Phe Cys Ser Ser Ser Ala
7445                7450                7455

Ile Ile Gly Asp Phe Gly Ser Cys Asp Tyr Ala Leu Gly Asn Arg
7460                7465                7470

Phe Gln Ser Ala Tyr Ala Leu Tyr Arg Ala Gln Met Val Glu Ser
7475                7480                7485

Ser Ala Leu Ser Gly Lys Thr Leu Ala Ile Asn Trp Pro Leu Trp
7490                7495                7500

Gln Asp Gly Gly Leu Gly Val Gly Asp Ala Glu Gln Thr Arg Phe
7505                7510                7515

Tyr Leu Gln Ser Ser Gly Gln Arg Ser Leu Cys Ser Gln Glu Ala
7520                7525                7530

Leu Ala Leu Leu Glu Gln Leu Leu Thr Gln Asp Arg Ala Gln Cys
7535                7540                7545

Leu Val Trp Ala Gly Gln Pro Asp Arg Leu Leu Arg Trp Val Asn
7550                7555                7560

Gln Glu Pro Leu Glu Ala Ala Thr Val Thr Val Pro Glu Pro Val
7565                7570                7575

Arg Ala Ala Lys Ala Val Ala Glu Arg Ala Glu Leu Gly Gly Gly
7580                7585                7590

Leu Asp Leu Gln Gln Cys Leu Leu Arg Asp Leu Lys Thr Lys Ile
7595                7600                7605

Cys Glu Leu Leu Gly Thr Gln Tyr Asn Glu Leu Glu Asn His Ala
7610                7615                7620

Asn Leu Val Asp Phe Gly Phe Asp Ser Ile Ser Leu Ala Glu Phe
7625                7630                7635

Ser Arg Val Leu Ser Arg Phe Tyr Ser Leu Asp Ile Ser Pro Ser
7640                7645                7650

Val Phe Phe Ser His Ser Thr Leu Asn Arg Leu Thr Ala Tyr Phe
7655                7660                7665

Leu Ala Glu His Arg Gln Thr Leu Glu Gly Phe Tyr Gln Gln Pro
7670                7675                7680

Gln Pro Ala Gly Pro Glu His Ala Pro Val Pro Thr Glu Val Ala
7685                7690                7695

Gln Val Ser Val Pro Val Pro Val Thr Ala Leu Leu Pro Thr Gly
7700                7705                7710

Thr Ser Ile Gly Ser Ala Ser Gln Gly Gln Asp Glu Pro Ile Ala
7715                7720                7725

Ile Ile Gly Leu Ser Gly Arg Phe Pro Gln Ala Arg Thr Ile Glu
7730                7735                7740

Glu Leu Trp Arg Ile Leu Glu Gln Gly Arg Asp Ala Ile Gln Glu
7745                7750                7755

Val Pro Ile Asp Arg Phe Asp Trp Arg Ser Tyr Tyr Ser Pro Ser
7760                7765                7770

Gln Glu Met Ser Lys Ser Asn Ser Lys Trp Gly Gly Cys Ile Pro
```

-continued

```
            7775                7780                 7785
Gly Ile Ala Glu Phe Asp Pro Leu Phe Phe Glu Ile Ser Pro Leu
            7790                7795                 7800
Glu Ala Glu Arg Met Asp Pro Arg Gln Arg His Leu Met Gln Glu
            7805                7810                 7815
Ala Trp Leu Ala Leu Glu Asp Ala Gly Tyr Gly Pro Glu Gln Leu
            7820                7825                 7830
Glu Cys Asn Lys Ile Ser Met Phe Val Gly Val Glu Glu Gly Cys
            7835                7840                 7845
Asp Tyr Gln Arg Arg Leu Thr Gln Gln Thr Ser Leu Thr Ser Met
            7850                7855                 7860
His Asn Gly Ile Leu Ala Ser Arg Leu Ala Tyr Phe Leu Asn Leu
            7865                7870                 7875
Lys Gly Pro Val Met Ala Ile Asn Thr Ala Cys Ser Ser Ala Leu
            7880                7885                 7890
Val Ala Val His Gln Ala Cys Gln Ser Leu Arg His Gly Glu Cys
            7895                7900                 7905
Asp Thr Ala Ile Ala Ala Gly Val Asn Leu Leu Val Ala Pro Glu
            7910                7915                 7920
Ala Tyr Val Gly Met Thr Gln Ala Gly Met Leu Ser Pro Asp Gly
            7925                7930                 7935
Lys Cys Tyr Val Phe Asp Lys Arg Ala Asn Gly Leu Val Pro Gly
            7940                7945                 7950
Glu Ala Val Ala Val Val Leu Lys Arg Leu Ser Lys Ala Leu
            7955                7960                 7965
Ala Asp Gly Asp Pro Ile Lys Ala Leu Ile Arg Gly Ser Gly Ile
            7970                7975                 7980
Asn Tyr Asp Gly Lys Thr Asn Gly Ile Thr Ala Pro Ser Gly Ala
            7985                7990                 7995
Ser Gln Thr Glu Leu Leu Glu Gly Ile Tyr Arg Gln Cys Ala Leu
            8000                8005                 8010
Gln Pro Gln Asp Ile Ser Tyr Ile Val Thr His Gly Thr Gly Thr
            8015                8020                 8025
Gln Leu Gly Asp Pro Ile Glu Ile Asn Ala Leu Tyr Asp Val Phe
            8030                8035                 8040
Lys Gly Lys Thr Asp Lys Gln Gly Phe Cys Ala Leu Thr Ser Ile
            8045                8050                 8055
Lys Ser Asn Leu Gly His Thr Phe Ala Ala Ser Gly Leu Val Ser
            8060                8065                 8070
Leu Ile Ser Leu Val Leu Ala Ile Arg His Arg Thr Ile Pro Ser
            8075                8080                 8085
Ser Leu His Cys Glu Gln Lys Asn Asp Tyr Ile Arg Trp Gln Glu
            8090                8095                 8100
Ser Pro Phe Tyr Val Asn Thr Arg Lys Lys His Trp Glu Cys Ala
            8105                8110                 8115
Leu Gly Gln Pro Arg Ile Gly Ala Val Ser Ala Phe Gly Met Ser
            8120                8125                 8130
Gly Thr Asn Ala His Val Val Gln Glu His Gln Pro Ala Glu
            8135                8140                 8145
Pro Ser Arg Trp Ser Thr Ala Ala Pro Tyr Tyr Leu Trp Val Val
            8150                8155                 8160
Ser Ala Lys Thr Glu Thr Thr Leu Gln Glu Gln Ile Arg Gln Trp
            8165                8170                 8175
```

-continued

```
Glu Asp Tyr Leu Ser Arg His Pro Asp Leu Asp Phe Glu Ala Val
    8180                8185                8190

Ser Tyr Thr Leu Leu Lys Gly Arg His His Phe Lys Tyr Arg Cys
    8195                8200                8205

Ala Ile Val Ala Lys Asp Leu Ser Gln Val Leu Gln Ala Leu Arg
    8210                8215                8220

Gln Ala Leu Asp Arg Gln Thr Gln Ala Asn Leu Cys Met Gly Cys
    8225                8230                8235

Val Asp Arg Asp Phe Ser Gly Gln Lys Ala Ile Arg Asp Phe Ile
    8240                8245                8250

Ala Ser Leu Ala Ala Gln Gly Glu Ala Leu Arg Asp Lys Pro Asp
    8255                8260                8265

Asp Tyr Arg Asp Asn Leu Ile Ala Leu Ala Asp Phe Tyr Cys Gln
    8270                8275                8280

Gly Tyr Glu Val Ala Asp Val His Leu Phe Ala Gly Arg Pro Gln
    8285                8290                8295

Arg Leu Ser Leu Pro Gly Tyr Pro Phe Ala Arg Glu His Tyr Trp
    8300                8305                8310

Ile Asp Glu Pro Ser Ala Ala His Arg Ala Glu Leu Ser Glu Arg
    8315                8320                8325

Ser Phe Asp Thr Gln Leu Asn Pro Leu Leu Gln Arg Asn Leu Ser
    8330                8335                8340

Thr Leu Ser Glu Gln Arg Tyr Ala Ser Ala Phe Lys Gly Asp Glu
    8345                8350                8355

Arg Phe Met Leu Arg Ile Ala His Gly Gln Glu Leu Leu Ile Pro
    8360                8365                8370

Thr Leu Phe Tyr Leu Glu Met Ala Arg Leu Ala Ala Gln Gln Ser
    8375                8380                8385

Leu Asp Met Pro Val Arg Ala Leu Lys Asn Met Val Trp Ala Cys
    8390                8395                8400

Pro Leu Tyr Tyr Gln Gln Gly Ser Asp Tyr Glu Leu Phe Leu Ser
    8405                8410                8415

Leu His Glu Lys Asp Ser Asp Leu Leu Tyr Thr Val Glu Met Gln
    8420                8425                8430

Gly Glu Pro Val Val Cys Gly His Phe Gly Glu Ile Asp Ser Thr
    8435                8440                8445

Glu Ala Ala Leu Gln Leu Pro Val Val Pro Asp Ile Ala Arg Leu
    8450                8455                8460

Arg Ala Ser Leu Pro Val Val Pro Asp Val Ala Leu Gly Ala Pro
    8465                8470                8475

Glu Met Gly Val Ala Arg Ile Ser Asp Val Gln Ala Asp Ala Thr
    8480                8485                8490

Thr Leu Leu Ala Thr Leu Asn Val Pro Ala Asp Gly Glu Asp Arg
    8495                8500                8505

Ser Met Trp Phe His Pro Leu Leu Ile Asn Ala Gly Trp Trp Leu
    8510                8515                8520

Leu Gln Gln Phe Val Gly Asp Arg Ala Glu Gly Gly Pro Leu Leu
    8525                8530                8535

Pro Phe Ser Leu Lys Gln Ile Thr Ala Pro Ala Ala Pro Pro Asp
    8540                8545                8550

Gln Ser Leu Leu Leu Leu Arg Arg His Val Arg Asp Val Glu Gln
    8555                8560                8565
```

```
Gly Leu Thr Cys Asp Met Ile Phe Tyr Asn Ser Lys Gly Glu Thr
    8570            8575            8580

Cys Leu Tyr Leu Gln Glu Leu Asn Val Thr Thr Leu Asp Arg Leu
    8585            8590            8595

Phe Asp Leu
    8600

<210> SEQ ID NO 8
<211> LENGTH: 433
<212> TYPE: PRT
<213> ORGANISM: Unknown
<220> FEATURE:
<223> OTHER INFORMATION: Bacterial Symbiont of Paederus fuscipes
<220> FEATURE:
<221> NAME/KEY: MISC_FEATURE
<223> OTHER INFORMATION: PedG putative flavin-binding monooxygenase

<400> SEQUENCE: 8

Met Asn Gln Lys Phe Arg Leu Cys Ile Ile Gly Gly Gly Pro Leu Gly
1               5                   10                  15

Ile Gly Leu Gly Arg Glu Leu Ser Glu Gly Ala Ile Asp Tyr Asp Leu
            20                  25                  30

Tyr Glu Ala Glu Ser Asp Leu Gly Gly Val Trp Asn Arg Glu Gly Lys
        35                  40                  45

Cys Gly Arg Val Tyr Pro Ser Leu His Leu Ile Ser Pro Lys Phe Asn
    50                  55                  60

Thr Gln Val Pro Asp Tyr Pro Met Pro Asp His Tyr Pro Val Tyr Pro
65                  70                  75                  80

Asn His Lys Met Met Leu Ala Tyr Met Arg Ser Tyr Ala Arg Asp Phe
                85                  90                  95

Gly Val Tyr Glu His Ala Ile Phe Asn Thr Ser Val Thr Arg Leu Glu
            100                 105                 110

Pro Asp Gly Glu Gly Trp Glu Val Glu Leu Ser Ser Gly Glu Arg Lys
        115                 120                 125

Arg Tyr Glu Val Val Ala Val Cys Asn Gly Ala Gln Arg Val Ala Arg
    130                 135                 140

Phe Pro Asp Pro Pro His Pro Gly Thr Phe Gln Gly Lys Val Leu His
145                 150                 155                 160

Ser Met Asp Tyr Lys Ser Pro Asp Leu Val Arg Asp Lys Arg Val Leu
                165                 170                 175

Val Val Gly Ala Gly Asn Ser Gly Cys Asp Ile Ala Val Asp Ala Ser
            180                 185                 190

His His Ala Glu Gln Val Tyr His Ser Thr Arg Arg Gly Tyr His Tyr
        195                 200                 205

Phe Pro Lys Phe Ile Asp Gly Lys Pro Thr Pro Gln Trp Met Leu Gln
    210                 215                 220

Leu Gly Asn Lys Phe Glu Thr Lys Glu Gln Thr Leu Ala Tyr Met Gln
225                 230                 235                 240

Gln Val Phe Lys Val Ala Gly Phe Asp Gly Met Asp Tyr Gly Leu Lys
                245                 250                 255

Lys Pro Asp His Pro Leu Asp Gly Ala His Pro Ile Met Asn Ser Gln
            260                 265                 270

Ile Leu Tyr His Ile Gly His Gly Asp Ile Leu Pro Lys Asp Asn Ile
        275                 280                 285

Glu Tyr Phe Glu Gly Asn Thr Val Phe Phe Ile Asp Gly Thr Lys Ala
    290                 295                 300
```

-continued

```
Asp Val Asp Leu Ile Ile Tyr Ala Thr Gly Tyr Asp Arg Asp Phe Pro
305                 310                 315                 320

Phe Ile Asp His Ala Leu Leu Glu Trp Lys Asp Gly Leu Pro Asp Leu
                325                 330                 335

Phe Ile His Ile Val Pro Arg Asn Leu Asp Asn Ile Phe Phe Phe Gly
                340                 345                 350

Phe Val Asn Ala Ala Ala Gly Leu Gly Asp Gly Leu Arg Leu Gln Gly
                355                 360                 365

Gln Phe Val Arg Ser Tyr Val Arg Ala Leu Gln Gln Lys Ser Lys Gly
                370                 375                 380

Tyr Phe Lys Phe Ile Gln Thr Lys Gln Asn Asp Asn Pro Asp Leu Gly
385                 390                 395                 400

Gln Asp Tyr Phe Leu Asp Ser His Arg His Arg Trp Glu Val Asp Phe
                405                 410                 415

Trp Lys Phe Ile Lys Cys Ala Arg Arg Tyr Arg Glu Met Leu Asp Glu
                420                 425                 430

Ile
```

<210> SEQ ID NO 9
<211> LENGTH: 6266
<212> TYPE: PRT
<213> ORGANISM: Unknown
<220> FEATURE:
<223> OTHER INFORMATION: Bacterial Symbiont of Paederus fuscipes
<220> FEATURE:
<221> NAME/KEY: MISC_FEATURE
<223> OTHER INFORMATION: PedH mixed type I polyketide
      synthase/nonribosomal peptide synthetase

<400> SEQUENCE: 9

```
Met Thr Phe Asn Thr Ser Asn Asp Gln Asp Ala Ala Ala Arg Glu Phe
1               5                   10                  15

Leu Glu His Glu Leu Ala Lys Ala Val Leu Asp Gln Phe Thr Glu Thr
                20                  25                  30

Gln Ser Ser Pro Ser Val Ala Gln Ile Ile Asp Val Ala Thr Asn Ser
                35                  40                  45

Val Lys Asn Ile Ser Pro Ala Ala Asp Glu Thr Leu Val Lys Phe Lys
50                  55                  60

Glu Glu Ile Ala Gln Ile Ala Ser Thr Val Leu Lys Ile Pro Ala Glu
65                  70                  75                  80

Arg Leu Asp Val Arg Glu Asn Met Ser Arg Tyr Gly Val Asp Ser Ile
                85                  90                  95

Val Val Thr Glu Ile Met Arg Cys Ile Ser Asp His Leu Asp Leu Pro
                100                 105                 110

Ile Ala Pro Thr Val Phe Phe Glu Ala Gly Asn Phe Glu Glu Leu Ala
                115                 120                 125

Thr Ile Leu Tyr Gln Arg Tyr His Lys Arg Ile Asp Glu Arg Tyr Gln
                130                 135                 140

Thr Gln Ala Arg Ala Gln Glu Arg Glu Ser Lys Val Ala Pro Leu
145                 150                 155                 160

His Glu Arg Gly Arg Ala Val Gln Lys Asn Gly Glu Leu Gly Val Met
                165                 170                 175

Glu Ala Leu Gly Ser Asp Ala Leu Ala Trp Ile Gln Arg Phe Arg Ser
                180                 185                 190

Val Thr Ser Ser Glu Val Ala Arg Pro Gln Ala Gln Val Arg Arg Val
                195                 200                 205
```

-continued

```
Thr Lys Ala Ala Arg Ala Asp Gly Glu Ile Leu Tyr Glu Pro Ile Ala
    210                 215                 220

Ile Ile Ala Met Asp Gly Val Phe Pro Gln Ser Ala Asp Leu Leu Glu
225                 230                 235                 240

Phe Glu Arg His Leu Arg Gln Gly Asp Cys Ile Ser Glu Ile Pro
                245                 250                 255

Ala Asp Arg Trp Asp Trp Arg Glu Val Tyr Gly Asp Pro Lys Glu Gly
            260                 265                 270

Glu Phe Thr Arg Val Lys Tyr Gly Gly Phe Ala Pro Asp Ile Asp Lys
        275                 280                 285

Phe Asp Pro Leu Phe Phe Gly Met Ser Pro Arg Glu Ala Gln Leu Met
290                 295                 300

Asp Pro Gln His Arg Gln Phe Ile Gln Cys Val Trp Arg Leu Ile Glu
305                 310                 315                 320

Ser Ala Gly Tyr Ala Pro Lys Ala Leu Ser Gly Ser Lys Val Gly Leu
                325                 330                 335

Phe Ile Gly Ile Asn Leu Gln Asp Tyr Ala His Leu Val Asp Arg Ala
            340                 345                 350

Asp Ala Met Asp Ala Leu His Leu Thr Ser Leu Gly His Met Phe Cys
        355                 360                 365

Pro Asn Arg Leu Ser Phe Leu Leu Asn Leu His Gly Pro Ser Gln Val
370                 375                 380

Ile Asp Thr Ala Cys Ser Ser Ser Val Ala Leu His Arg Ala Val
385                 390                 395                 400

Leu Ser Ile Gln Tyr Glu Gly Cys Glu Met Ala Ile Ala Gly Gly Ala
                405                 410                 415

Asn Leu Leu Ile Ser Pro Asp Met His Ile Met Tyr Ser Lys Val Gly
            420                 425                 430

Met Ile Cys Glu Asp Gly Arg Cys Lys Thr Phe Ser Lys Glu Ala Asn
        435                 440                 445

Gly Tyr Val Arg Ser Asp Gly Ile Gly Ala Val Leu Leu Lys Ser Leu
450                 455                 460

His Arg Ala Glu Glu Asp Gly Asp Ile Ile Leu Ala Val Ile Arg Gly
465                 470                 475                 480

Ser Ala Glu Asn His Gly Gly Met Ser Thr Ser Leu Thr Ala Pro Asn
                485                 490                 495

Pro Lys Ala Gln Ala Ser Leu Ile Val Glu Ala His Arg Lys Ala Lys
            500                 505                 510

Val Asp Pro Arg Ser Ile Gly Tyr Ile Glu Cys His Gly Thr Gly Thr
        515                 520                 525

Ser Leu Gly Asp Pro Ile Glu Ile Asn Gly Leu Lys Leu Ala Phe Glu
530                 535                 540

Gln Leu Tyr Arg Glu Ala Gly His Glu Leu Pro Met Arg Pro Ser Cys
545                 550                 555                 560

Gly Leu Gly Ser Val Lys Ser Asn Ile Gly His Ala Glu Thr Ser Ala
                565                 570                 575

Gly Ile Ala Gly Val Ile Lys Thr Val Leu Ser Leu Arg Asn Lys Arg
            580                 585                 590

Leu Tyr Gln Ser Leu His Ser Ala Asp Ile Asn Pro Met Ile Asp Leu
        595                 600                 605

Glu Gln Ser Pro Phe Phe Ile Leu Gln Gln Gly Arg Asp Trp Gln Arg
610                 615                 620

Pro Leu Ile Glu Gly Gln Glu Gln Pro Arg Arg Ala Gly Ile Ser Ser
```

-continued

```
            625                 630                 635                 640
        Phe Gly Ala Gly Gly Ser Asn Ala His Ile Val Ile Glu Glu Tyr Leu
                        645                 650                 655

Val Pro Pro Leu Pro Glu Pro Val Leu Gln Gly Pro Leu Ile Ile Leu
                        660                 665                 670

Leu Ser Ala Lys Asn Ala Ala Arg Leu Asp Asp Met Thr Arg Gln Leu
                        675                 680                 685

Leu His Trp Leu Glu Ser Thr Glu Arg Val Pro Ser Ile Val Asp Ile
                        690                 695                 700

Ala Tyr Thr Leu Gln Val Gly Arg Glu Ala Leu Ser Gln Arg Leu Ala
        705                 710                 715                 720

Leu Ile Val Thr Asp Leu Val Asp Leu Lys Thr Arg Leu Arg Ser Leu
                        725                 730                 735

Leu Glu Gly Gly Glu Pro Ser Gly Val Tyr Arg Gly Asp Thr Lys
                        740                 745                 750

Ala Asn Lys Ala Ala Leu Gln Glu Ile Asp Asp Asp Arg Ser Leu
                        755                 760                 765

Glu Lys Leu Ile Ala Tyr Phe Ser Gln Asp Asp Val His Lys Leu Ala
                770                 775                 780

Lys Leu Trp Thr Gln Gly Val Glu Val Asp Trp Pro Ser Leu Tyr Ala
        785                 790                 795                 800

Arg Met Pro Phe Ala Gly Arg Ser Pro Arg Arg Val Ala Leu Pro Thr
                        805                 810                 815

Tyr Pro Phe Ala Arg Gln Arg His Trp Ile Asp Lys Ile Ala Gly Ser
                        820                 825                 830

Pro Gln Asn Arg Arg Glu Ala Ala Ala Thr Ser Pro Ile Val Ala Ser
                        835                 840                 845

Arg Pro Ala Gly Tyr Pro Leu Leu Gln Arg Thr Val Ala Asp Pro Ala
        850                 855                 860

Lys Arg Cys Tyr Gly Cys Val Leu Thr Gly Glu Glu Phe Phe Leu Thr
        865                 870                 875                 880

Asp His Gln Val Lys Gly Asn Lys Val Leu Pro Gly Val Ala Tyr Leu
                        885                 890                 895

Glu Met Ala Arg Ala Ala Val Glu Arg Ile Ser Ala His Asp Ala Arg
                        900                 905                 910

Asp Lys Ala Pro Leu Tyr Leu Lys Asn Val Val Trp Ala Arg Pro Leu
                        915                 920                 925

Met Val Asn Gly Ala Thr Ser Leu Tyr Ile Ser Leu Ala Pro Glu Gln
                        930                 935                 940

Asp Gly Arg Val Ala Tyr Arg Ile Tyr Ser Glu Gly Glu Gly Glu Ser
        945                 950                 955                 960

Thr Glu Ile Leu His Ser Gln Gly Ser Ala Ile Leu Arg Gly Ser Glu
                        965                 970                 975

Ser Gly Ser Glu Val Ala Thr Ala Arg Leu Asp Leu Asp Glu Leu Arg
                        980                 985                 990

Glu Arg Ile Thr Gly Gly Ala Pro Asn Ala Gln Arg Leu Glu Ser Ala
                        995                 1000                1005

Arg Cys Tyr Glu Ala Phe Arg Ala Met Gly Ile Asp Tyr Gly Pro
                        1010                1015                1020

Ala His Arg Cys Leu Glu Ser Val Tyr Phe Ser Ala Lys Glu Ala
                        1025                1030                1035

Leu Pro Ala Pro Glu Val Leu Ala Lys Leu Val Leu Pro Ala Trp
                        1040                1045                1050
```

-continued

```
Ala Gln Glu Gly Ala Ala Ala Phe Val Leu His Pro Gly Leu Ile
    1055                1060                1065

Asp Ser Gly Leu Gln Ala Cys Ile Gly Leu Ile Val Gly Ala Gly
    1070                1075                1080

His Glu Leu Pro Thr Glu Ala Glu Ser Glu Ile Ser Gly Met Thr
    1085                1090                1095

Ala Thr Leu Pro Phe Ala Leu Asp Ser Leu Thr Leu Leu Ala Pro
    1100                1105                1110

Pro Ser Asp Ile Leu Trp Val Trp Val Arg Tyr Ala Asp Gly Ser
    1115                1120                1125

Ser Thr Ser Asp Lys Val Gln Lys Leu Asp Ile Asp Phe Cys Asp
    1130                1135                1140

Val His Gly Arg Val Cys Ile Arg Leu Arg Gly Phe Ser Ser Arg
    1145                1150                1155

Ala Leu Glu Ala Glu Gln Ala Pro Asp Ser Ala Thr Thr Val Leu
    1160                1165                1170

Cys Glu Pro Leu Trp Asn Glu Arg Ser Val Asp Ser Ser Ala Gln
    1175                1180                1185

Val Leu Trp Ala Arg His Glu Val Leu Leu Cys Asp Val Gln Asp
    1190                1195                1200

Asp Phe Asp Ala Val Phe Glu Gln Asn Leu Gly Val Thr Leu Gly
    1205                1210                1215

Val Pro Cys Ser Arg Leu Ala Leu Asp Gly Pro Leu Glu Asn Arg
    1220                1225                1230

Tyr Gln Lys Ala Ala Leu Gly Val Phe Glu Trp Ile Arg Gln Ala
    1235                1240                1245

Ile Gly Asp Lys Ile Gly Gly Ser Leu Leu Leu Gln Ile Val Ile
    1250                1255                1260

Pro Ala Thr Asp Arg Gly Cys Leu Leu Ala Gly Leu Ser Gly Leu
    1265                1270                1275

Leu Lys Thr Ala Asn Arg Glu Asn Asn Arg Phe Arg Gly Gln Leu
    1280                1285                1290

Ile Glu Leu Glu Leu Arg Glu Thr Ala Glu Gly Val Ala Ala Lys
    1295                1300                1305

Leu Gln Ala Asp Ser Arg Ala Ala Gln Asp Thr His Ile Arg His
    1310                1315                1320

Arg Asp Ser Leu Arg Glu Val Arg His Trp Gln Val Val Pro Ala
    1325                1330                1335

Gly Ala Val Ser Thr Val Leu Pro Trp Lys Asp Asn Gly Val Tyr
    1340                1345                1350

Leu Ile Thr Gly Gly Asn Gly Gly Leu Ala Trp Leu Phe Ala Glu
    1355                1360                1365

His Ile Ala Gln His Ala Pro His Ala Ser Leu Val Met Cys Gly
    1370                1375                1380

Arg Ser Ala Leu Thr Ser Glu Arg His Gln Ala Leu Glu His Leu
    1385                1390                1395

Arg Gly Met Gly Pro Arg Leu Asp Tyr Arg Arg Val Asp Val Thr
    1400                1405                1410

Gln Ala Ala Gln Val Glu Ala Leu Ile Arg Asp Leu Thr Thr Val
    1415                1420                1425

Tyr Glu Arg Ile Asp Gly Val Leu His Cys Ala Gly Leu Leu Arg
    1430                1435                1440
```

-continued

```
Asp Asn Phe Ile Gln Lys Lys Thr Pro Gln Glu Phe Ala Glu Val
    1445                1450                1455

Leu Ala Pro Lys Val Ala Gly Thr Leu His Leu Asp His Ala Thr
    1460                1465                1470

Gln Ala Leu Asp Leu Asp Phe Phe Ile Leu Phe Ser Ser Ala Ala
    1475                1480                1485

Gly Val Trp Gly Ser Ala Gly Gln Thr Asp Tyr Ala Ala Ala Asn
    1490                1495                1500

Gly Phe Leu Asp Ala Phe Ala Ser Tyr Arg Gln Ala Leu Thr Ala
    1505                1510                1515

Ala Gly Arg Arg His Gly Arg Thr Leu Ser Ile Asp Trp Pro Leu
    1520                1525                1530

Trp Ala Glu Gly Gly Met Arg Met Glu Ala Asn Ala Gln Ile Met
    1535                1540                1545

Met Gln Arg Ala Thr Gly Leu Thr Ala Leu Pro Ser Ala Ala Gly
    1550                1555                1560

Ile Glu Ala Phe Cys Arg Ile Met Gly Ser Gly Ala Thr Gln Met
    1565                1570                1575

Met Val Met His Gly Ala Ala Val Arg Ile Gln Arg Met Leu Asp
    1580                1585                1590

Glu Ser Ala Glu Pro Leu Arg Ala Ala Leu Pro Val Arg Ser Ala
    1595                1600                1605

Thr Ala Thr Glu Glu Pro Ala Ala Arg Gly Arg Phe Asp Thr Gln
    1610                1615                1620

Ala Leu Lys Ala Gly Ile Glu Gln Leu Leu Leu Gln Arg Ile Ala
    1625                1630                1635

Glu Leu Met Lys Phe Glu Leu Glu Asp Leu Asp Val Glu Thr Gln
    1640                1645                1650

Leu Thr Asp Tyr Gly Phe Asn Ser Ile Thr Leu Thr Asp Phe Ser
    1655                1660                1665

Asn Arg Leu Asn Gln Gln Tyr Ser Leu Glu Met Thr Pro Thr Val
    1670                1675                1680

Phe Phe Glu Tyr Pro Thr Val Ser Glu Phe Ala Gly Trp Leu Ser
    1685                1690                1695

Thr Glu Tyr Pro Asp Val Phe Ala Gln Ala Leu Gly Leu Ser Ile
    1700                1705                1710

Glu Thr Pro Ala Glu Phe Arg Pro Glu Val Arg Thr Asp Asp Gly
    1715                1720                1725

Ala Arg Glu Pro Ser Ser Val Leu Ser Ser Val Gln Ala Glu Arg
    1730                1735                1740

Met Leu Gly Gly Ile Ala Met Met Ala Ser Gln Ala Val Ser Val
    1745                1750                1755

Asp Asp Ala Ala Val Ala Ile Ile Gly Met Ser Gly Arg Phe Pro
    1760                1765                1770

Met Ala Glu Asp Ile Gln Ala Phe Trp Ser Asn Leu Leu Glu Gly
    1775                1780                1785

Lys Asp Cys Ile Ser Glu Ile Pro Glu Asp Arg Trp Asp Trp Arg
    1790                1795                1800

Ala Ile Tyr Gly Asp Pro Thr Lys Glu Ala Asn Lys Ser Asp Val
    1805                1810                1815

Lys Trp Gly Gly Phe Ile Asp Gly Val Ala His Phe Asp Ala Arg
    1820                1825                1830

Phe Phe Gly Ile Ser Pro Arg Glu Ala Glu Leu Met Asp Pro Gln
```

```
              1835                1840                1845
Gln Arg Leu Leu Met Gln Tyr Val Trp Lys Ala Val Glu Asp Ala
    1850                1855                1860
Gly Tyr Ala Pro Ala Ser Leu Ser Gly Ser Arg Thr Ala Ile Phe
    1865                1870                1875
Val Gly Thr Ala Ser Ser Gly Tyr Gly Glu Leu Met Ala Gln Glu
    1880                1885                1890
Gly Leu Ala Ile Glu Ser Tyr Ser Ser Thr Gly Val Val Gly Ser
    1895                1900                1905
Val Gly Pro Asn Arg Met Ser Tyr Phe Leu Asn Leu His Gly Pro
    1910                1915                1920
Ser Glu Pro Val Glu Thr Ala Cys Ser Ser Ser Leu Val Ala Ile
    1925                1930                1935
His Arg Ala Leu Ser Ala Met Ala Ile Gly Asp Cys Asp Gln Ala
    1940                1945                1950
Ile Val Gly Gly Val Asn Leu Leu Ile Ser Pro Gln Thr His Ile
    1955                1960                1965
Ser Phe Asn Lys Ala Gly Met Leu Cys Ser Asp Gly Arg Cys Lys
    1970                1975                1980
Thr Phe Ser Ser Lys Ala Asn Gly Tyr Val Arg Gly Glu Gly Val
    1985                1990                1995
Gly Met Leu Met Leu Lys Lys Leu Lys Ala Ala Glu Gln Ala Gly
    2000                2005                2010
Asn His Ile Tyr Ala Val Ile Arg Gly Ser Ala Glu Asn His Gly
    2015                2020                2025
Gly Arg Gly Ser Ser Leu Thr Ala Pro Asn Pro Lys Ala Gln Thr
    2030                2035                2040
Gln Leu Ile Lys Ala Ala Tyr Glu Arg Ala Gly Ile Asp Pro Arg
    2045                2050                2055
Ser Val Ser Tyr Ile Glu Ala His Gly Thr Gly Thr Glu Leu Gly
    2060                2065                2070
Asp Pro Ile Glu Ile Asn Ala Leu Lys Ala Ala Phe Lys Asp Leu
    2075                2080                2085
Tyr Gln Ala Thr Gly Ser Val Glu Val Thr Ala Pro His Cys Ala
    2090                2095                2100
Leu Gly Ala Val Lys Thr Asn Ile Gly His Leu Glu Leu Ala Ala
    2105                2110                2115
Gly Val Ala Gly Val Ile Lys Val Leu Leu Gln Leu Lys His Lys
    2120                2125                2130
Thr Leu Val Lys Ser Leu His Cys Asp Glu Val Asn Pro Tyr Ile
    2135                2140                2145
Gln Leu Gln Gly Ser Pro Phe Tyr Leu Leu Ser Glu Thr Gln Pro
    2150                2155                2160
Trp Ser Thr Leu Arg Asp Ala Gln Gly Arg Glu Leu Pro Arg Arg
    2165                2170                2175
Ala Gly Ile Ser Ser Phe Gly Phe Gly Gly Val Asn Ala His Leu
    2180                2185                2190
Val Leu Glu Glu Tyr Pro Gln Ala Glu Tyr Ile Ala Glu Ser Ser
    2195                2200                2205
Met Glu Ser Leu Gln Ala Ser Ser Thr Cys Val Val Pro Leu Ser
    2210                2215                2220
Ala Lys Thr Pro Glu Arg Leu Lys Val Tyr Ala Ser Ser Leu Leu
    2225                2230                2235
```

-continued

```
Asp Phe Ile Thr Ala Pro Val Ala Val Ser Gly Pro Glu Gly Glu
    2240                2245                2250

Gly Ala His Gln Leu Leu Thr Arg Trp Met Gln Ala Met Val Ala
    2255                2260                2265

Glu Ile Leu Glu Ile Ala Val Glu Glu Ile Glu Leu Thr Gln Pro
    2270                2275                2280

Leu Gln Glu Tyr Gly Phe Asp Thr Val His Gly Val Ile Leu Leu
    2285                2290                2295

Ala Arg Phe Arg Asp Ala Trp Gly Val Asp Val Gly Ser Ala Val
    2300                2305                2310

Leu Leu Gly His Gln Thr Ser Ile Thr Ser Phe Val Thr Thr Val
    2315                2320                2325

Leu Arg Glu Gln Pro Ser Leu Arg Glu Arg Leu Ser Gly Glu Pro
    2330                2335                2340

Ala Ala Val Ala Ala Ser Pro Glu Pro Gly His Arg Val Arg Arg
    2345                2350                2355

Asp Ile Arg Leu Ala Asp Leu Ala Tyr Thr Leu Gln Val Gly Arg
    2360                2365                2370

Asp Ala Met Ala Glu Arg Leu Ala Met Thr Ala Asp Ser Met Glu
    2375                2380                2385

Glu Leu Glu His Lys Leu Arg Ala Phe Val Glu Gly Arg Ser Gly
    2390                2395                2400

Glu Val Lys Asp Leu Tyr Gln Gly Ser Val Lys Gln Asn Lys Arg
    2405                2410                2415

Ile Leu Ser Ala Phe Ala Gly Asp Glu Glu Met Gln Glu Ala Leu
    2420                2425                2430

Asp Lys Trp Ile Gln Arg Gly Lys Leu Ala Lys Leu Leu Glu Ile
    2435                2440                2445

Trp Val Ala Gly Leu Asn Ile Asp Trp Gln Gln Leu Tyr Gly Ser
    2450                2455                2460

Asp Arg Ser Gly Thr Pro Pro His Arg Ile Ser Ala Pro Gly Tyr
    2465                2470                2475

Pro Phe Ala Glu Gln Arg His Trp Ile Gln Thr Pro Ser Met Ser
    2480                2485                2490

Pro Ala Pro Val Pro Val Ser Ala Pro Val Ala Ala Pro Glu Val
    2495                2500                2505

Leu His Pro Leu Val His Glu Ser Leu Cys Gly Pro Gly Leu Thr
    2510                2515                2520

Arg Phe Lys Ser Arg Phe Glu Gly Thr Glu Phe Phe Leu Asp Asp
    2525                2530                2535

His Arg Val Lys Gly Arg Lys Val Met Pro Gly Val Ala Tyr Leu
    2540                2545                2550

Glu Met Ala His Ala Ala Ala His Leu Ala Gln Ala Ile Ala Pro
    2555                2560                2565

Ser Ser Arg Val Cys Leu Gln Asp Val Ala Trp Ile Ser Pro Leu
    2570                2575                2580

Leu Val Asp Gln Pro Gln Glu Val Leu Ile Asp Ile Glu Pro Gly
    2585                2590                2595

Gln Gly Glu Arg Arg Ser Phe Ser Val Tyr Cys Met Ala Gly Asp
    2600                2605                2610

Gly Arg Arg Leu His Ser Gln Gly Gly Leu Leu Tyr Val Pro Gln
    2615                2620                2625
```

-continued

```
Asp Ser Ala Gln Ser Arg Pro Cys Leu Glu Leu Gln Ala Leu Leu
    2630            2635                2640

Ala Gln Ser Gly Met Arg Leu Ile Asn Ala Asp His Cys Tyr Glu
    2645            2650                2655

Arg Leu Ala Ala Gly Gly Leu Glu Tyr Gly Pro Gly His Arg Gly
    2660            2665                2670

Ile His Gln Leu Tyr Ala Gly Asn Asp Gln Val Leu Ala His Leu
    2675            2680                2685

Val Leu Pro Glu Ser Leu Gln Ala Thr Ala Gly His Tyr Val Leu
    2690            2695                2700

His Pro Cys Leu Val Asp Ser Ala Leu Gln Ala Ser Ile Gly Leu
    2705            2710                2715

Val Leu Thr Ala Ser Glu Thr Ala Ser Gly Gly Arg Glu Ala Pro
    2720            2725                2730

Leu Met Leu Pro Phe Ala Val Gln Ser Val Asp Val Phe Ala Ser
    2735            2740                2745

Cys Glu Ser Val Thr Trp Ala Trp Leu Arg His Gln Ala Gly Ile
    2750            2755                2760

Pro Val Ser Gly Arg Val Gln Lys Leu Asp Ile Asp Leu Cys Asp
    2765            2770                2775

Glu Arg Gly Lys Val Cys Ile Gln Ile Lys Gly Phe Ser Ser Arg
    2780            2785                2790

Val Leu Ala Pro Glu Gly Gly Arg Ser Glu Ala Val Thr Ala His
    2795            2800                2805

Glu Arg Arg Glu Pro Leu Gly Val Phe Ala Ala Arg Ala Thr Thr
    2810            2815                2820

Pro Ser Pro Ala Pro Ala Pro Ala Leu Ser Ala Val Ala Glu Val
    2825            2830                2835

Asp Asp Asp Glu Leu Ser Lys Arg Ala Ile Asp Tyr Phe Lys Ala
    2840            2845                2850

Leu Leu Ser Ser Thr Leu Lys Phe Pro Val Glu Glu Ile Ala Pro
    2855            2860                2865

Asp Glu Thr Met Asp Ala Tyr Gly Ile Asp Ser Ile Met Val Ala
    2870            2875                2880

Glu Leu Thr Ser Thr Leu Glu Ser His Phe Gly Pro Leu Ser Lys
    2885            2890                2895

Thr Leu Phe Phe Glu Tyr Gln Thr Leu Gly Glu Leu Val Asp Tyr
    2900            2905                2910

Phe Leu Asp Ala His Arg Ala Arg Leu Leu Gln Leu Cys Val Thr
    2915            2920                2925

Gly Gly Ala Gly Thr Ser Leu Ala Ala Asp Ala Val Leu Asp Ser
    2930            2935                2940

Pro Pro Ser Thr Lys Pro Ala Val Leu Val Glu His Leu Pro Gln
    2945            2950                2955

Pro Val Pro Met Ala Ala Ala Ser Asn Thr Ala Leu Asp Ile Ala
    2960            2965                2970

Val Ile Gly Ile Ser Gly Arg Tyr Pro Met Ala Asn Asp Leu Asp
    2975            2980                2985

Glu Phe Trp Leu Asn Leu Arg Glu Gly Lys Asp Cys Val Ser Glu
    2990            2995                3000

Val Pro Ser Gln Arg Trp Asn Trp Arg Asp His Tyr Ser Glu Glu
    3005            3010                3015

His Ser Arg Ala Gly Gly His Phe Cys Lys Trp Gly Gly Phe Ile
```

```
                3020                3025                3030
Asp Asp Ile Asp Lys Phe Asp Pro Leu Phe Phe Asn Ile Ser Pro
    3035                3040                3045
Ser Ala Ala Glu Tyr Met Asp Pro Gln Glu Arg Leu Phe Leu Glu
    3050                3055                3060
His Ala Trp Met Ala Met Glu Asp Ala Gly Tyr Arg Arg Glu Asp
    3065                3070                3075
Leu Arg Lys Leu Ala Arg Gly Ser Ala Ala Glu Asp Leu Pro Gly
    3080                3085                3090
Gln Val Gly Val Tyr Ala Gly Val Met Tyr Ser Glu Tyr Gln Leu
    3095                3100                3105
Leu Gly Ile Glu Ala Ala Arg Gln Gly Lys Gly Ala Thr Val Ala
    3110                3115                3120
Asn Phe His Ala Ser Val Ala Asn Arg Val Ser Tyr Val Leu Asp
    3125                3130                3135
Leu His Gly Pro Ser Met Thr Val Asp Thr Met Cys Ser Ser Ser
    3140                3145                3150
Leu Thr Ala Leu His Leu Ala Cys Gln Asp Leu Lys Thr Gly Arg
    3155                3160                3165
Thr Asp Met Ala Leu Ala Gly Gly Val Asn Leu Ser Val His Pro
    3170                3175                3180
Asn Lys Tyr Ser Val Leu Ser Leu Asn Glu Phe Ile Ser Ser Gln
    3185                3190                3195
Gly Arg Cys Thr Ser Phe Gly Glu Gly Gly Asp Gly Tyr Val Pro
    3200                3205                3210
Ser Glu Gly Val Gly Val Val Leu Leu Lys Arg Leu Val Asp Ala
    3215                3220                3225
Glu Arg Asp Arg Asp His Ile His Ala Val Ile Lys Ser Ser Val
    3230                3235                3240
Leu Asn His Gly Gly Lys Thr His Gly Phe Ser Val Pro Asn Pro
    3245                3250                3255
Lys Ala Gln Gln His Leu Ile Ser Arg Ala Leu Arg Glu Ala Glu
    3260                3265                3270
Val Asp Pro Arg Ala Ile Thr Tyr Val Glu Ala His Gly Thr Gly
    3275                3280                3285
Thr Pro Leu Gly Asp Pro Ile Glu Val Thr Ala Leu Ser Lys Ala
    3290                3295                3300
Phe Ala Gln Tyr Ser Leu Gly Gly Gln Pro Tyr Trp Ile Gly Ser
    3305                3310                3315
Val Lys Ser Asn Ile Gly His Thr Glu Ser Thr Ala Gly Ile Ala
    3320                3325                3330
Gly Leu Ser Lys Val Ile Leu Gln Met Arg Glu Gly Gln Leu Ala
    3335                3340                3345
Pro Ser Leu His Ser Gln Thr Leu Asn Pro Asn Ile Asp Phe Ala
    3350                3355                3360
Ser Ser Pro Phe Gln Val Asn Arg Gln Leu Arg Glu Trp Pro Arg
    3365                3370                3375
Pro Val Leu Asp Gly Arg Leu Gln Pro Arg Val Ala Ser Leu Ser
    3380                3385                3390
Ser Phe Gly Ala Gly Gly Ser Asn Ala His Leu Val Ile Ser Glu
    3395                3400                3405
Tyr Ile Glu Pro Val Glu Arg Arg Ala Pro Asp Thr Thr Asp Ser
    3410                3415                3420
```

-continued

```
Arg Pro Cys Leu Ile Val Leu Ser Ala Lys Ser Glu Glu Arg Leu
    3425                3430                3435

Lys Ala Tyr Ala Gly Lys Leu Cys Ala Phe Leu Glu Ser Ala Gly
    3440                3445                3450

Thr Arg Leu Glu Leu Ser Leu Arg Asn Val Ala Tyr Thr Leu Gln
    3455                3460                3465

Val Gly Arg Glu Ala Met Gln His Arg Leu Ala Phe Ser Ala Arg
    3470                3475                3480

Ser Ile Glu Asp Ala Arg Arg Ile Leu Glu Ala Phe Ala Gln Gly
    3485                3490                3495

Arg Glu Val Ala Arg Leu Tyr Arg Gly Tyr Val Lys Thr Ala Arg
    3500                3505                3510

Asp Ser Arg Ser Gly Arg Arg Asp Glu Ser Val Ala Glu Pro Ile
    3515                3520                3525

Arg Gly Lys Asp His Asp Ala Val Leu Ala Leu Trp Val Lys Gly
    3530                3535                3540

Val Asp Val Asn Trp Gln Glu Leu Tyr Ala Ala Glu Ser Asp Leu
    3545                3550                3555

Pro Tyr Arg Ile Ser Leu Pro Thr Tyr Pro Phe Ala Arg Glu Arg
    3560                3565                3570

Tyr Trp Leu Thr Leu Pro Glu Pro Pro Pro Gly Gly Glu Arg
    3575                3580                3585

Arg Leu Pro Asn Ala Pro Ile Ala Leu Ala Val Leu Ser Asp Ala
    3590                3595                3600

Leu Leu Gly Ser Pro Ala Trp Lys Ala Arg Ala Ala Glu Pro Ala
    3605                3610                3615

Ala Val Leu Gly Asp Tyr Val Glu Arg Arg Leu Tyr Val Val Gly
    3620                3625                3630

Ser Ser Met Glu Val Pro Gly Ile Ala Cys Val Ala Leu Asp Ser
    3635                3640                3645

Asp Gly Gln Thr Val Asp Gln Arg Ile Thr Asp Tyr Ala Thr Gln
    3650                3655                3660

Leu Phe Gly Asp Ile Lys Thr Leu Phe Gln Arg Lys Pro Lys Pro
    3665                3670                3675

Lys Gly Glu Val Leu Phe Gln Ile Leu Leu Ala Gln Asp Thr Pro
    3680                3685                3690

Met Ala Gly Ala Leu Ala Ala Leu Leu Lys Thr Ala Ala Met Glu
    3695                3700                3705

Asn Pro Gln Phe Phe Gly Gln Val Leu Glu Leu Gly Ala Asp Ile
    3710                3715                3720

Leu Pro Asp Pro Ser Lys Leu Gly Ala Leu Leu Asp Glu Asn Ala
    3725                3730                3735

Gln Asp Arg Arg His Pro His Ile Arg Tyr Ser Arg Ser Gly Arg
    3740                3745                3750

Gln Val Pro Ser Trp Ser Val Leu Ser Met Ala Ser Glu Gly Glu
    3755                3760                3765

Ala Val Trp Lys Gln Gly Gly Val Tyr Leu Val Ser Gly Gly Val
    3770                3775                3780

Gly Gly Leu Gly Leu Ile Phe Ala Arg Glu Ile Ile Arg Arg Val
    3785                3790                3795

Ser Asp Val Thr Leu Ile Leu Thr Gly Arg Ser Pro Leu Glu Gly
    3800                3805                3810
```

-continued

Ala Arg Ala Ala Ala Val Gln Ala Leu Arg Ala Ser Gly Thr Asn
    3815                3820            3825

Val Glu Tyr Arg Arg Val Asp Val Gly Asp Arg His Ala Val Thr
    3830                3835            3840

Asp Leu Ile Gly Glu Ile Glu Arg Phe Cys Arg Asp Arg Gly Tyr
    3845                3850            3855

Gly Glu Leu Asn Gly Val Ile His Ala Ala Gly Val Leu Arg Asp
    3860                3865            3870

Asn Phe Ile Leu Arg Lys Thr His Ala Gln Phe Ser Glu Val Met
    3875                3880            3885

Ala Ala Lys Val Ala Gly Val Val Asn Leu Asp Leu Ala Thr Arg
    3890                3895            3900

Ser Ala Asn Leu Asp Phe Phe Val Met Phe Ser Ser Leu Ala Gly
    3905                3910            3915

Val Val Gly Asn Pro Gly Gln Cys Asp Tyr Ser Thr Ala Asn Ala
    3920                3925            3930

Phe Leu Asp His Tyr Thr Val Tyr Arg Asn Gln Leu Val Ala Lys
    3935                3940            3945

Gly Gly Thr Ser Ala Pro Lys Gly His Thr Leu Ser Ile Asp Trp
    3950                3955            3960

Pro Leu Trp Gln Glu Gly Gly Met Asp Leu Ala Pro Glu His Lys
    3965                3970            3975

Glu Glu Leu Trp Arg Ser Ala Gly Ile Lys Pro Met Arg Ser Glu
    3980                3985            3990

Ile Gly Ile Ala Ala Phe Tyr Ala Cys Leu Gln Ala Gly Val Glu
    3995                4000            4005

Gln Ala Leu Val Leu Glu Gly Asp Leu Pro Arg Leu Arg Gln Leu
    4010                4015            4020

Phe Phe Asp Asp His Ser Gln Pro Val Val Asp Glu Ala Ala Gln
    4025                4030            4035

Gly Ala Glu Thr Cys Thr Ser Glu His Ser Pro Asp Ser Leu Val
    4040                4045            4050

Arg Ala Val Glu Gly Leu Leu Val Arg His Leu Ser Glu Leu Leu
    4055                4060            4065

Lys Leu Pro Glu His Arg Ile Glu Thr Asp Val Pro Val Glu His
    4070                4075            4080

Tyr Gly Ile Asp Ser Val Gly Met Met Arg Leu Thr Val Glu Leu
    4085                4090            4095

Glu Glu Thr Phe Gly Ser Leu Ser Lys Thr Leu Phe Phe Glu Tyr
    4100                4105            4110

Gln Asp Val Gln Ser Leu Ala Ala Tyr Leu Ala Gln Thr Phe Pro
    4115                4120            4125

Asp Gln Ala Arg Ala Leu Cys Gly Glu Pro Ser Ala Gln Ala Ala
    4130                4135            4140

Pro Met Glu Val Pro Ile Ser Ser Ala Pro Glu Pro Gly Ser Leu
    4145                4150            4155

Pro Ala Gly Leu Val Glu Ala Val Val Thr Ala Gly Glu Ala Ala
    4160                4165            4170

Glu Trp Gln Met Gly Glu Arg Asp Ile Ala Ile Gly Met Ser
    4175                4180            4185

Gly Arg Phe Pro Phe Ala Pro Asp Leu Glu Ala Phe Trp Glu Asn
    4190                4195            4200

Leu Ser Gln Gly Cys Asp Cys Ile Thr Glu Ile Pro Pro Thr Arg

-continued

```
            4205                4210                4215
Trp Lys His Gln Glu Tyr Phe Asp Pro Glu Lys Gly Lys Pro Gly
    4220                4225                4230
Lys Thr Tyr Cys Lys Trp Gly Gly Phe Leu Glu Ser Ile Asp Gln
    4235                4240                4245
Phe Asp Pro Leu Phe Phe Lys Ile Pro Pro Ala Gln Ala Glu Val
    4250                4255                4260
Leu Asp Pro Gln Glu Arg Leu Phe Leu Glu Thr Val Trp Asn Leu
    4265                4270                4275
Leu Glu Ser Ser Gly Tyr Leu Gly Glu Thr Leu Gln Arg Ile Ala
    4280                4285                4290
Gln Ser Arg Val Gly Val Phe Val Gly Ser Met Ser Gln Gln Tyr
    4295                4300                4305
His Ala Phe Gln Ala Asp Leu Thr Arg Glu Ser Leu Val Thr Met
    4310                4315                4320
Ser Ser His Ser Ser Ile Ala Asn Arg Val Ser Tyr Phe Phe Asp
    4325                4330                4335
Phe Gln Gly Pro Ser Val Ala Val Asp Thr Met Cys Ser Ser Ala
    4340                4345                4350
Leu Val Ala Val His Met Ala Cys Glu Ser Leu Leu Arg Asp Asp
    4355                4360                4365
Cys Lys Ala Ala Val Ala Gly Gly Val Asn Leu Ser Ile His Pro
    4370                4375                4380
Lys Lys Tyr Ile Gly Leu Ser Ala Ser Gln Ile Leu Gly Ser His
    4385                4390                4395
Pro Asp Ser Ser Ser Phe Gly Gln Gly Asp Gly Tyr Leu Pro Ser
    4400                4405                4410
Glu Gly Val Gly Ala Val Leu Leu Lys Pro Leu Arg Glu Ala Val
    4415                4420                4425
Ala Asp Asn Asp Thr Ile Leu Gly Val Ile Lys Ser Thr Thr Ile
    4430                4435                4440
Asn His Ser Gly Gln Ser Asn Gly Tyr Phe Val Pro Asn Gly Ala
    4445                4450                4455
Ala Gln Thr Glu Leu Met Val Ser Asn Phe Thr Lys Ala Gly Ile
    4460                4465                4470
Asp Pro Arg Thr Leu Ser Tyr Val Glu Ser Ala Ala Asn Gly Ser
    4475                4480                4485
Ser Leu Gly Asp Ala Ile Glu Ile Asn Ala Leu Thr Ala Gly Phe
    4490                4495                4500
Gly Arg Tyr Thr Ala Asp Lys Gln Phe Cys Ala Leu Gly Ser Val
    4505                4510                4515
Lys Ser Asn Ile Gly His Gly Glu Ala Ala Ser Gly Ile Ala Gln
    4520                4525                4530
Leu Ile Lys Val Leu Leu Gln Leu Lys His Arg Gln Leu Val Pro
    4535                4540                4545
Thr Ile Lys Ala Gln Pro Leu Asn Ser Asn Ile Asp Phe Thr His
    4550                4555                4560
Thr Pro Phe Cys Leu Gln Arg Arg Leu Glu Pro Trp Arg Arg Pro
    4565                4570                4575
Ser Leu Ala Leu Gly Asp Gly Pro Met Arg Glu Tyr Pro Leu Arg
    4580                4585                4590
Ala Thr Val Ser Ser Phe Gly Ala Gly Gly Ser Asn Ala His Leu
    4595                4600                4605
```

-continued

```
Ile Leu Glu Glu Phe Pro Leu Asp Arg Gln Glu Ser Asp Asn Leu
    4610                4615                4620

Glu His Glu Arg Leu Pro Asp Ser Glu Glu His Leu Leu Val Phe
    4625                4630                4635

Ser Ala Arg Thr Glu Ala Gln Leu Gln Ala Val Val Gln Gln Met
    4640                4645                4650

Leu Ala Glu Leu Glu Lys Glu Arg Ser Leu Ser Leu Ala Asp Ile
    4655                4660                4665

Ala Phe Thr Leu Gln Thr Gly Arg Lys Ala Met Asp Phe Arg Leu
    4670                4675                4680

Ala Val Val Val Glu Gly Val Glu Ala Arg Leu Arg Ala Val Glu
    4685                4690                4695

Ser Leu Arg Ala Tyr Leu Arg Asn Glu Thr Pro Gly Pro Thr Val
    4700                4705                4710

Phe Val Asp Asn Val Leu Glu Asp His Ser Arg Val Arg Glu Gln
    4715                4720                4725

Leu Val Gly Ser Ala Gly Gln Ala Ile Leu Gln Arg Ala Leu Met
    4730                4735                4740

Glu Pro Asp Leu Arg Ala Leu Ala Gly Tyr Trp Val Lys Gly Ile
    4745                4750                4755

Lys Leu Pro Trp His Gln Leu His Ala Gly Trp Lys Arg Lys Arg
    4760                4765                4770

Val Val Leu Pro Thr Tyr Pro Phe Glu Arg Lys Ser Tyr Trp Leu
    4775                4780                4785

Gly Gly Asn Ala Gly Arg Val Val Leu Lys Ala Ser Glu His Ser
    4790                4795                4800

Glu Arg Asp Ala Val Glu Pro Glu Val Glu Arg Asn Gly Ser Ala
    4805                4810                4815

Ser Ile Glu Arg Val Ile Ala Gln Arg Leu Gly Ser Met Leu Gly
    4820                4825                4830

Met Asp Glu Gly Glu Ile Glu Met Gly Arg Ser Phe Gln Asp Tyr
    4835                4840                4845

Gly Val Asp Ser Ile Ala Ser Ser Glu Leu Cys Arg Ala Leu Glu
    4850                4855                4860

Gln Thr Phe Lys Val Gln Ile Ser Ser Leu Glu Leu Phe Ser Leu
    4865                4870                4875

Ser Ser Leu Ala Glu Leu Ala Glu Leu Ile Ala Gly Arg Leu Pro
    4880                4885                4890

Glu Gln Pro Leu Lys Lys Leu Lys Lys Leu Glu Thr Pro Glu Thr
    4895                4900                4905

Val Ser Val Ser Ser Val Ser Met Pro Val Ser Glu Gly Gln Lys
    4910                4915                4920

Gly Leu Trp Leu Leu His Gln Arg Ser Pro Asn Met Ser Ala Tyr
    4925                4930                4935

Asn Val Pro Leu Val Phe Cys Phe Lys Gly Glu Leu Asp Val Ser
    4940                4945                4950

Leu Phe Arg Lys Ala Cys Glu Leu Met Leu Glu Arg His Pro Ile
    4955                4960                4965

Leu Gly Ser Val Phe Arg Leu Thr Arg Glu Asp Ile Gln Arg Ile
    4970                4975                4980

Glu Leu Arg Glu Ala His Met Gly Phe Glu His Val Ser Val Glu
    4985                4990                4995
```

-continued

```
Leu His Gln Arg Ser Glu Ile Leu Glu Arg Leu Arg Asp Tyr Ser
    5000                5005                5010
Lys Gln Pro Phe Asp Leu Glu Gln Gly Pro Leu Tyr Arg Val Tyr
    5015                5020                5025
Leu Leu Thr Ser Arg Thr Asp Asn Asp Ala Tyr Val Leu Ile Cys
    5030                5035                5040
Val His His Ile Val Phe Asp Gly Ser Ser Ala Met Leu Leu Leu
    5045                5050                5055
Lys Asp Leu Leu Ala Thr Tyr Arg Asn Leu Leu His Gly Gly Gln
    5060                5065                5070
Pro Ala Asn Ile Arg Pro Ala Ala Gly Tyr Gln Ser Phe Val His
    5075                5080                5085
Trp Gln Arg Gln Leu Leu Asn Ser Glu Lys Gly Gln Thr Gln Leu
    5090                5095                5100
Asp Tyr Trp Lys Thr Gln Leu Ser Gly Glu Gln Pro Val Leu Ser
    5105                5110                5115
Leu Pro Tyr Asp Phe Pro Arg Pro Ala Met Pro Gly Phe His Gly
    5120                5125                5130
Ala Ser Glu Glu Leu Thr Leu Ser Gln Ala Leu Ser Ser Arg Leu
    5135                5140                5145
Gln Ala Leu Thr Lys Thr Leu Gln Val Asn Pro Ser Val Val Phe
    5150                5155                5160
Leu Gly Ala Phe Lys Leu Leu Leu Asn Arg Tyr Ser Gly Tyr Asp
    5165                5170                5175
Asp Ile Arg Val Gly Met Pro Thr Ser Gly Arg Ser Leu Pro Ala
    5180                5185                5190
Phe Gln Asp Gln Ile Gly Tyr Phe Val Asn Met Leu Val Ile Arg
    5195                5200                5205
Ser Arg Val Ile Gly Gln Gln Ser Val Ala Asp Phe Leu Lys Val
    5210                5215                5220
Leu Gln Leu Thr Val Ala Thr Ala Leu Asp Asn Ala Asp Cys Pro
    5225                5230                5235
Phe Pro Val Val Leu Glu Ala Leu Arg Gly Asp Gly Glu Pro Gln
    5240                5245                5250
Ser Ser Ser Trp Phe Gln Val Val Phe Ser Tyr Gln Asn Phe Ile
    5255                5260                5265
Arg Asp Gly Asp Ser Ala Trp Leu Gln Ala Asp Thr Gln Gly Thr
    5270                5275                5280
Thr Ala Val Glu Leu Val Ser Gly Ile Asn Gln Glu Gly Gly Asn
    5285                5290                5295
Asp Ile Ala Leu Asp Val Tyr His Gly Gly Glu Gln Phe Leu Leu
    5300                5305                5310
Lys Met Ala Tyr Asp Lys Asp Leu Phe Glu Ala Ala Thr Ile Arg
    5315                5320                5325
Arg Ile Met Thr His Tyr Val Asn Leu Leu Glu Ser Ile Ala Thr
    5330                5335                5340
His Pro Arg Gly Cys Ile Ala Asp Gln Thr Leu Leu Ser Ala Asp
    5345                5350                5355
Glu Arg Gln Lys Ile Leu Gly Asp Trp Ser Asn Thr Gly Ala Ser
    5360                5365                5370
Leu Ser Met Glu Arg Gln Asn Ile Val Gln Leu Phe Gln Arg Gln
    5375                5380                5385
Val Arg Ser Thr Pro His Lys Thr Ala Leu Val Phe Glu Gln Gln
```

```
                    5390                    5395                    5400

Ser Leu Thr Phe Ala Glu Leu Asp Asp Gln Ser Ser Arg Leu Ser
    5405                    5410                    5415

Leu Cys Leu Ala Asn Tyr Lys Val Ala Pro Gly Asp Leu Val Gly
    5420                    5425                    5430

Ala Cys Leu Gly Arg Gly Val Arg Met Val Val Ala Leu Leu Ala
    5435                    5440                    5445

Ile Leu Lys Ala Asp Ala Val Tyr Val Pro Ile Ala Pro Asp Ser
    5450                    5455                    5460

Pro Val Gln Arg Ile Cys Arg Leu Leu Val Asp Ser Gly Ile Ser
    5465                    5470                    5475

Leu Leu Leu Ser Glu Leu Glu Leu Cys Asn Ser Phe Leu Ser Asp
    5480                    5485                    5490

Leu Gly Thr Ile Glu Cys Val Cys Leu Ala Ile Asp Ala Pro Gly
    5495                    5500                    5505

Trp Glu Pro Glu Glu Gly Leu Pro Val Pro Val Ile Glu
    5510                    5515                    5520

Gly Arg Gln Pro Ala Tyr Val Ile Tyr Thr Ser Gly Ser Thr Gly
    5525                    5530                    5535

Gln Pro Lys Gly Val Ile Ile Ser His Asp Ser Ile Ser His His
    5540                    5545                    5550

Cys Gln Val Ile Arg Asp Tyr Tyr Arg Ile Thr Ala Gln Asp Val
    5555                    5560                    5565

Ile Leu Gln Phe Ala Pro Met Asn Val Asp Ala Ala Leu Glu Gln
    5570                    5575                    5580

Leu Leu Pro Gly Leu Ile Ser Gly Ala Thr Val Val Ile Arg Ser
    5585                    5590                    5595

Glu Pro Leu Trp Ser Pro Asp Ile Leu Cys Arg Lys Val Val Glu
    5600                    5605                    5610

Leu Gly Ile Ser Val Leu Asp Leu Pro Pro Ser Tyr Leu Tyr Glu
    5615                    5620                    5625

Leu Leu Leu Glu Ile Arg Asp Val Ala Gly Trp Ser Arg Pro Pro
    5630                    5635                    5640

Ser Leu Arg Leu Val Ile Ser Gly Gly Glu Ala Leu Ser Pro Glu
    5645                    5650                    5655

Thr Leu Ser Leu Trp Cys Gly Cys Ala Leu Ser Glu Cys Arg Leu
    5660                    5665                    5670

Val Asn Ala Tyr Gly Pro Thr Glu Thr Thr Ile Thr Ser Thr Val
    5675                    5680                    5685

Tyr Glu Ile Glu Ser Arg Ala Arg Thr Phe Thr Arg Leu Pro Glu
    5690                    5695                    5700

Ser Val Pro Ile Gly Arg Pro Leu Pro Gly Glu Ser Ala Tyr Ile
    5705                    5710                    5715

Leu Asp Thr Gln Arg Arg Pro Leu Pro Val Gly Val Pro Gly Glu
    5720                    5725                    5730

Leu Tyr Ile Gly Gly Ala Gly Val Ala Ile Gly Tyr Leu Asn Arg
    5735                    5740                    5745

Pro Glu Leu Thr Ala Ser Thr Phe Val Glu Asn Pro Phe Met Ala
    5750                    5755                    5760

Gly Thr Arg Leu Tyr Lys Thr Gly Asp Ala Ala Arg Trp Leu Ala
    5765                    5770                    5775

Asp Gly Asn Ile Ala Leu Leu Gly Arg Leu Asp Gln Gln Val Lys
    5780                    5785                    5790
```

-continued

```
Ile Arg Gly Phe Arg Val Glu Cys Gly Glu Ile Glu Ala Ala Leu
5795             5800            5805

Gln Ala Leu Asp Val Val Lys His Val Ala Val Leu Ala Gln Pro
5810             5815            5820

Thr Gln Gly Ser His Arg Leu Val Ala Phe Leu Glu Leu Val Gln
5825             5830            5835

Pro Ala Leu Pro Glu Trp Lys Gln His Leu Lys Gln Ala Leu Ile
5840             5845            5850

Lys Lys Leu Pro Glu His Met Ile Pro Ser Val Phe Val Ser Leu
5855             5860            5865

Pro Arg Ile Pro Leu Ser Val Ser Gly Lys Val Asp Arg Asn Ala
5870             5875            5880

Leu Lys His Leu Glu Leu Ala Asn Thr Glu Ser Glu Val Phe Val
5885             5890            5895

Ala Pro Arg Thr Ser Met Glu Ile Arg Leu Ala Glu Ile Trp Arg
5900             5905            5910

Arg Val Leu Asp Ile Asp Arg Val Gly Val His Asp Ser Phe Phe
5915             5920            5925

Asp Leu Gly Gly His Ser Leu Leu Ala Leu Arg Leu Met Ser Ala
5930             5935            5940

Ile Lys Gln Gly Leu Gly Tyr Glu Leu Pro Ile Ser Ser Leu Phe
5945             5950            5955

Gln Ala Pro Thr Leu Thr Ala Gln Ala Glu Leu Leu Gly Gln Asp
5960             5965            5970

Ala Ala Val Trp Ser Pro Leu Val Cys Leu Gln Ala Ser Gly Glu
5975             5980            5985

Leu Ser Pro Trp Phe Cys Ile His Ala Ala Ala Gly Asn Val Leu
5990             5995            6000

Cys Tyr Arg Glu Leu Ala Glu Cys Leu Gly Ile Glu Arg Pro Phe
6005             6010            6015

Tyr Ala Leu Gln Ala Pro Asp Ala Val Gly Gly Gly His Pro Gly
6020             6025            6030

Ser Ile Val Gly Leu Ala Ala Leu Tyr Val Arg Ala Ile Arg Ile
6035             6040            6045

Phe Gln Pro Trp Gly Pro Tyr Phe Leu Ala Gly Trp Ser Met Gly
6050             6055            6060

Gly Val Val Ala Tyr Glu Met Ala Gln Gln Leu Leu Gln Ala Gly
6065             6070            6075

Glu Gln Val Glu Val Leu Ala Leu Leu Glu Ser Tyr Thr Pro Glu
6080             6085            6090

Ala Ile Arg Ser Leu Glu Arg Lys Ala Leu Gly Leu Ser Ala Glu
6095             6100            6105

Ser Asp Asp Arg Met Asp Lys Leu Leu Arg Thr Phe Ala Val Glu
6110             6115            6120

Leu Gly Ile Gly Glu Thr Pro Trp Glu Leu Ser Ala Val Asp Leu
6125             6130            6135

Ala Gln Gly Leu Glu Trp Ile Leu Lys Arg Leu Glu Gly Ser Asn
6140             6145            6150

Leu Ser Thr Ala Ser Phe Asp Leu Glu Gln Leu His Lys Leu Phe
6155             6160            6165

Arg Leu Tyr Glu Ala Asn Leu Asn Ala Leu Asp Arg Tyr Arg Leu
6170             6175            6180
```

```
Gln Pro Tyr Ser Gly Arg Val Val Leu Ile Tyr Ala Asp Gln Thr
    6185            6190                6195

Gln Gln Ile Asp Ala Asp Glu Ala Gln His Leu Gly Gly Trp Gln
    6200            6205                6210

Pro Trp Leu Arg Ser Gly His Cys Arg Ser Ala Thr Ile Val Gly
    6215            6220                6225

Asp His Tyr Ser Ile Leu Gln Arg Pro Gln Val Val Gln Leu Ala
    6230            6235                6240

Lys Val Leu Thr Ala Leu Val Lys Asp Asp Gly Leu Ala Thr Lys
    6245            6250                6255

Tyr Arg Glu Val Met Val Tyr Ser
    6260            6265

<210> SEQ ID NO 10
<211> LENGTH: 32
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(1)
<223> OTHER INFORMATION: m is a or c
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: r is a or g
<220> FEATURE:
<221> NAME/KEY: misc_feature
<222> LOCATION: (9)..(10)
<223> OTHER INFORMATION: n is a, c, g, or t
<220> FEATURE:
<221> NAME/KEY: misc_feature
<222> LOCATION: (11)..(11)
<223> OTHER INFORMATION: w is a or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (13)..(13)
<223> OTHER INFORMATION: s is c or g
<220> FEATURE:
<221> NAME/KEY: misc_feature
<222> LOCATION: (14)..(14)
<223> OTHER INFORMATION: m is a or c
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (21)..(21)
<223> OTHER INFORMATION: y is c or t
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (27)..(27)
<223> OTHER INFORMATION: r is a or g
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
```

```
<222> LOCATION: (31)..(31)
<223> OTHER INFORMATION: m is a or c

<400> SEQUENCE: 10
mgngargcnn wnsmnatgga yccncarcan mg                                32

<210> SEQ ID NO 11
<211> LENGTH: 29
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(3)
<223> OTHER INFORMATION: r is a or g
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (11)..(11)
<223> OTHER INFORMATION: r is a or g
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (13)..(13)
<223> OTHER INFORMATION: s is c or g
<220> FEATURE:
<221> NAME/KEY: misc_feature
<222> LOCATION: (14)..(14)
<223> OTHER INFORMATION: w is a or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (27)..(27)
<223> OTHER INFORMATION: r is a or g

<400> SEQUENCE: 11
ggrtcnccna rnswngtncc ngtnccrtg                                    29

<210> SEQ ID NO 12
<211> LENGTH: 21
<212> TYPE: DNA
<213> ORGANISM: Artificial Sequence
<220> FEATURE:
<223> OTHER INFORMATION: Primer

<400> SEQUENCE: 12
tggcatcgtg gggaaaggct g                                            21
```

<210> SEQ ID NO 13
<211> LENGTH: 19
<212> TYPE: DNA
<213> ORGANISM: Artificial Sequence
<220> FEATURE:
<223> OTHER INFORMATION: Primer

<400> SEQUENCE: 13
ggcgcaggtg ctgacacgc                                              19

<210> SEQ ID NO 14
<211> LENGTH: 23
<212> TYPE: DNA
<213> ORGANISM: Artificial Sequence
<220> FEATURE:
<223> OTHER INFORMATION: Primer

<400> SEQUENCE: 14
ttagccatcg agagttacag ctc                                         23

<210> SEQ ID NO 15
<211> LENGTH: 21
<212> TYPE: DNA
<213> ORGANISM: Artificial Sequence
<220> FEATURE:
<223> OTHER INFORMATION: Primer

<400> SEQUENCE: 15
aatcgccgat agccatcgcc g                                           21

<210> SEQ ID NO 16
<211> LENGTH: 21
<212> TYPE: DNA
<213> ORGANISM: Artificial Sequence
<220> FEATURE:
<223> OTHER INFORMATION: Primer

<400> SEQUENCE: 16
gacgccatgg atgcactgca c                                           21

<210> SEQ ID NO 17
<211> LENGTH: 22
<212> TYPE: DNA
<213> ORGANISM: Artificial Sequence
<220> FEATURE:
<223> OTHER INFORMATION: Primer

<400> SEQUENCE: 17
tattggatgc tcagcaccgc ac                                          22

<210> SEQ ID NO 18
<211> LENGTH: 22
<212> TYPE: DNA
<213> ORGANISM: Artificial Sequence
<220> FEATURE:
<223> OTHER INFORMATION: Primer

<400> SEQUENCE: 18
gggctcagtt tccaccctta tg                                          22

<210> SEQ ID NO 19
<211> LENGTH: 19
<212> TYPE: DNA
<213> ORGANISM: Artificial Sequence
<220> FEATURE:
<223> OTHER INFORMATION: Primer -continued

<400> SEQUENCE: 19
ccggcgctgc agagccagg                                                  19

<210> SEQ ID NO 20
<211> LENGTH: 6
<212> TYPE: PRT
<213> ORGANISM: Artificial Sequence
<220> FEATURE:
<223> OTHER INFORMATION: Conserved motif of PedF1/AVES2-1

<400> SEQUENCE: 20

Glu Pro Ile Ala Ile Val
1               5

<210> SEQ ID NO 21
<211> LENGTH: 6
<212> TYPE: PRT
<213> ORGANISM: Artificial Sequence
<220> FEATURE:
<223> OTHER INFORMATION: Conserved motif of PedF1/AVES2-1

<400> SEQUENCE: 21

Asp Pro Gln Gln Arg Leu
1               5

<210> SEQ ID NO 22
<211> LENGTH: 4
<212> TYPE: PRT
<213> ORGANISM: Artificial Sequence
<220> FEATURE:
<223> OTHER INFORMATION: Conserved motif of PedF1/AVES2-1

<400> SEQUENCE: 22

Cys Ser Ser Ser
1

<210> SEQ ID NO 23
<211> LENGTH: 9
<212> TYPE: PRT
<213> ORGANISM: Artificial Sequence
<220> FEATURE:
<223> OTHER INFORMATION: Conserved motif of PedF1/AVES2-1
<220> FEATURE:
<221> NAME/KEY: misc_feature
<222> LOCATION: (6)..(6)
<223> OTHER INFORMATION: Xaa can be any naturally occurring amino acid

<400> SEQUENCE: 23

His Gly Thr Gly Thr Xaa Leu Gly Asp
1               5

<210> SEQ ID NO 24
<211> LENGTH: 13
<212> TYPE: PRT
<213> ORGANISM: Artificial Sequence
<220> FEATURE:
<223> OTHER INFORMATION: Conserved motif of PedF1/AVES2-1
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 24

-continued

```
Gly Xaa Gly Gly Xaa Asn Ala His Val Ile Leu Glu Glu
1               5                   10

<210> SEQ ID NO 25
<211> LENGTH: 5
<212> TYPE: PRT
<213> ORGANISM: Artificial Sequence
<220> FEATURE:
<223> OTHER INFORMATION: Conserved motiv of PedF1/AVES2-1
<220> FEATURE:
<221> NAME/KEY: misc_feature
<222> LOCATION: (4)..(4)
<223> OTHER INFORMATION: Xaa can be any naturally occurring amino acid

<400> SEQUENCE: 25

Gly His Ser Xaa Gly
1               5

<210> SEQ ID NO 26
<211> LENGTH: 4
<212> TYPE: PRT
<213> ORGANISM: Artificial Sequence
<220> FEATURE:
<223> OTHER INFORMATION: Conserved motif of PedF1/AVES2-1
<220> FEATURE:
<221> NAME/KEY: misc_feature
<222> LOCATION: (2)..(2)
<223> OTHER INFORMATION: Xaa can be any naturally occurring amino acid

<400> SEQUENCE: 26

Gly Xaa Asp Ser
1
```

GENE CLUSTER OF PEDERIN BIOSYNTHESIS GENES

The present invention relates to the cloning, sequencing and analysing of a gene cluster encoding a modular polyketide synthase enzyme involved in the biosynthesis of the antitumor compound pederin.

In particular, the present invention relates to a novel isolated nucleic acid comprising a pederin biosynthetic gene cluster, fragments of this gene cluster corresponding polypeptides vectors and recombinant host cells or transgenic organisms comprising said nucleic acids, a method for producing pederin and the use of said nucleic acids for preparing a modified pederin biosyntheisis synthesis gene cluster or modified pederin molecules.

Thus, the invention relates to novel genes and isolated nucleic acids encoding polypeptide/proteins exhibiting functional activities involved in the pederin biosynthesis, such polypetides themselves, and methods or uses prepare pederin or modified pederin derivatives.

Invertebrates, particularly those from marine environments are an important source of natural products with high therapeutic potential. The low availability of most of these metabolities however, represents a serious impediment to drug development. As many invertebrates are difficult to cultivate and chemical, synthesis is usually not economical, alternative and ecologically friendly sources of natural products are urgently needed. The actual producers of many drug candidates isolated from invertebrates may well be symbiotic bacteria, but so far no producing symbiont has ever been successfully cultured. Genes from bacterial secondary metabolism are usually clustered, which can simplify their cloning and transfer into a heterologous host. Heterologous expression in a culturable bacterium could therefore generate renewable sources of rare symbiont-derived drug candidates isolated from invertebrates.

The highly active antitumor compounds of the pederin group (FIG. 1) represents the strongest evidence the for such a bacterial biosynthesis (Narquizian, R., Kocienski, P. J., The pederin family of antitumor agents: structures, synthesis and biological activity. The Role of Natural Products in Drug Discovery. Ernst Schering Research Foundation Workshop Series, 32, Springer-Verlag, Heidelberg, Germany, 25-56 (2000)). While almost all of these metabolites were isolated from marine sponges, pederin is, exclusively known from terrestrial *Paederus* and *Paederidus* beetles. These notorious insects carry pederin as vesicant deterrent in their hemolymph and cause severe dermatitis when accidentally crushed on the human skin. In all *Paederus* species studied so far, up to 90% of the contain high levels of pederin, and only these (+) females contain high levels of pedrin, offspring, Pederin free (−)-females do not produce (+)-offspring, unless they are fed eggs of (+)-females. This non-Mendelian mode of inheritance can be prevented if the (+)-eggs are previously, treated with antibiotecs, which strongly suggests bacterially mediated pederin biosynthesis. In stark contrast to the large number of suspected symbiont drug candidates from marine invertebrates, pederin is the only terrestrial example known to date.

The structure of pedrin and early labelling studies suggest that the metabolite is largely synthesised from malonyl- and methymalonyl-coenzyme A (CoA) units by a type I polyketide synthase (PKS). Such megasynthases consist of repeated modules, along which the growing polyketide chain is processed in an assembly line-like fashion. Normally, each module minimally carries ketosynthase (KS), acyltransferase (AT) and acyl carrier protein (ACP) domains to perform exactly one chain elongation cycle, and optional additional domains to catalyze further modifications.

As pointed out above, drug development from natural sources is commonly hampered by low yields and the difficulty of sustaining invertebrate cultures. To obtain insight into the true producer and to find alternative sources for these rare drug candidates, it was the object of the present invention to establish a way to provide pederin in a more convenient and economic fashion.

This object was solved by cloning, sequencing and analysing the pederin genes.

In a first aspect, the present invention provides an isolated nucleic acid comprising a pederin biosynthetic gene cluster or being complementary to a sequence comprising a pederin biosynthetic gene cluster. This cluster represents the first example of genes from an unculturable symbiont encoding the biosynthesis of a drug candidate.

This gene cluster is preferably derived from *Paederus* or *Paederidus* rove beetles, and in particular from a bacterial symbiont of *Paederus* or *Paederidus* rove beetles.

Figure 3:
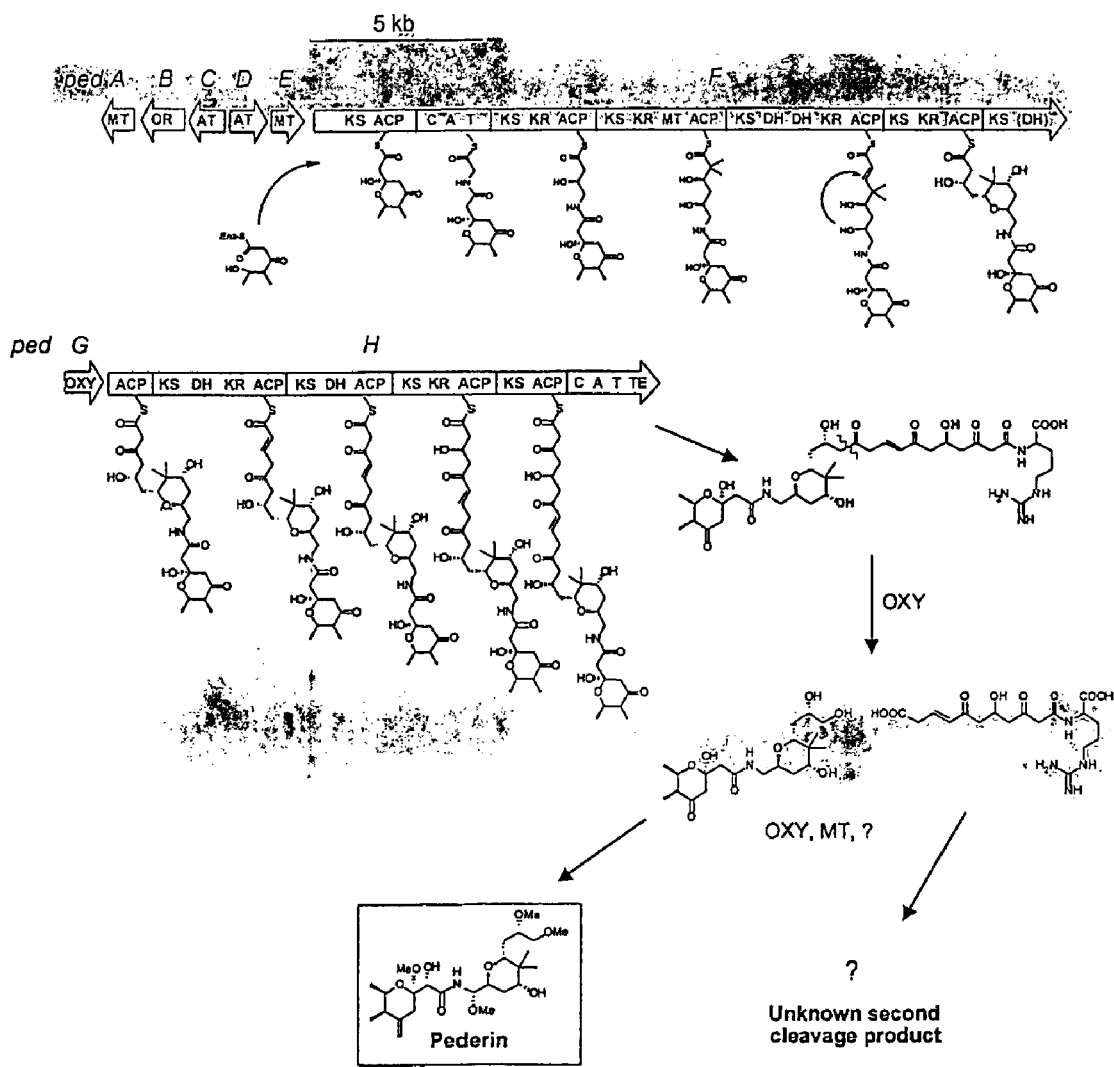

The isolated nucleic acid preferably comprises nucleic acid fragments forming individual units and/or modules of the pederin biosynthetic gene cluster as it is shown in more detail in FIG. 3. As depicted in FIG. 3, the cluster contains the units pedA to pedH which are either coding units for individual enzymes or for one or several polyketide synthase or nonribosomal peptide synthetase modules. The pedF unit, for example, comprises five polyketide synthase modules and one peptide synthetase module and/or the pedH unit comprises four polyketide synthase modules and one peptide synthetase module. Each polyketide synthase module comprises at least one ketosynthase domain and one acyl carrier protein domain. The isolated nucleic acid preferably comprises one or more of the pedA to pedH units essentially consisting of the nucleic acid sequences encoding the protein sequences shown in SEQ ID NO: 2 to 9.

In a particularly preferred embodiment, the isolated nucleic acid according to the present invention comprises:
- a nucleotide sequence as shown in SEQ ID NO:1; or
- a nucleotide sequence which is the complement of SEQ ID NO:1; or
- a nucleotide sequence hybridising under highly stringent conditions to SEQ ID NO:1 or to the complement thereof; or
- a nucleotide sequence having at least 80% sequence identity with SEQ ID NO:1 or with the complement thereof.

Under a further aspect, the present invention is directed to nucleic acid fragments selected from the group consisting of pedA, pedB, pedC, pedD, pedE, pedF, pedG and/or pedH as shown in FIG. 3. Especially important are the fragments essentially consisting of pedF and/or pedH. Further preferred are the nucleic acid fragments comprising one or more nucleotide sequences encoding the protein sequences as shown in SEQ ID NOs: 2 to 9. Also preferred are the corresponding parts of the nucleotide sequence SEQ ID NO:1.

Furthermore, the invention is directed to a polypeptide encoded by a nucleic acid as described above. The polypeptide preferably has functional activity in the synthesis of pederin and/or a polyketide and/or a peptide synthetase moiety.

In addition, the invention also provides a vector comprising a nucleic acid consisting essentially of the pederin biosynthetic gene cluster or a vector comprising a nucleic acid as described above as well as a recombinant host cell or a transgenic organism comprising said nucleic acid or containing said vector. In a preferred embodiment, the host cell used is a bacterial cell. As bacterial cells, *Pseudomonas, Acinetobacter, Bacillus* or *Streptomyces* cells are particularly preferred.

Finally, a method for producing pederin using a recombinant host cell or a transgenic organism as described above is provided, comprising the steps of:
culturing the recombinant host cell under conditions to express the pederin biosynthetic gene cluster; and
isolating the produced pederin.

The inventive nucleic acids can be used in the preparation of a modified pederin biosynthesis gene cluster or in the preparation of a modified pederin molecule. Modified pederin molecules might be used as an alternative antitumor agent and might be even more potent antitumor agents as the original pederin.

In the following, reference is made to the figures further illustrating the present invention.

FIG. 1 shows some members of the pederin family of antitumor compounds isolated from terrestrial beetles and marine sponges.

Figure 2:
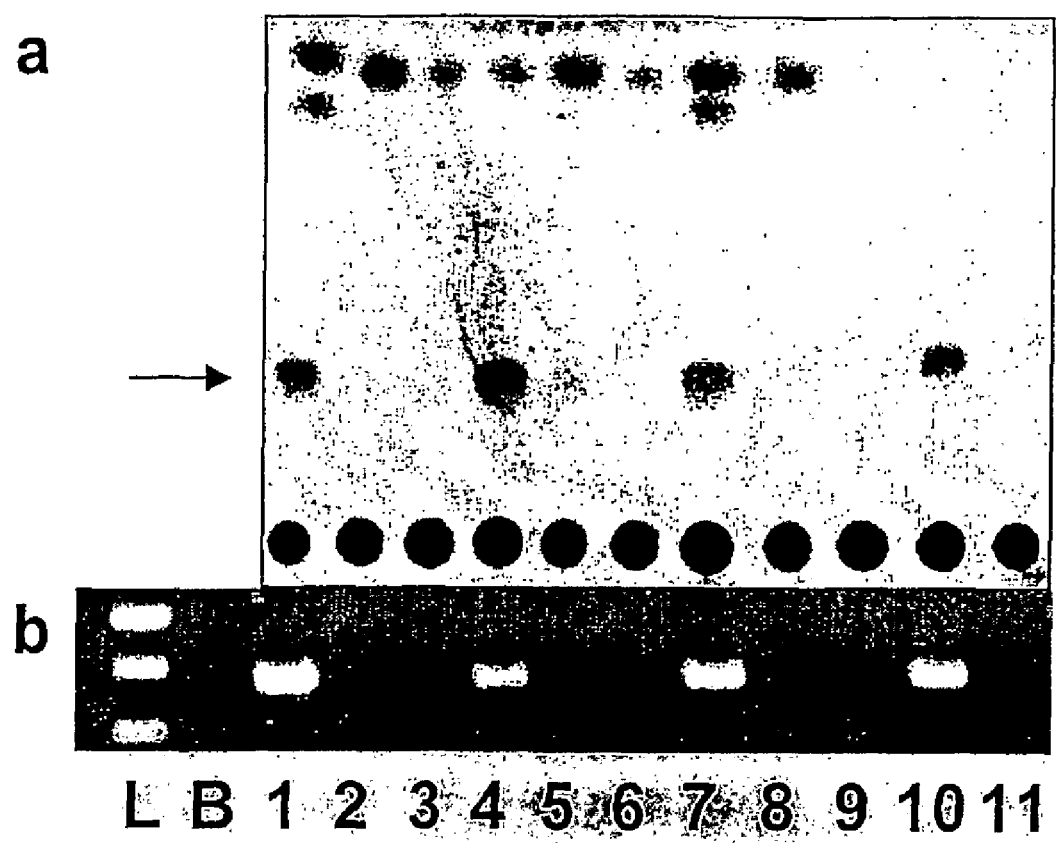

FIG. 2 illustrates the PCR amplification of PKS gene fragments from beetle total DNA. a, TLC analysis of the ethanolic beetle extracts. The arrow indicates the position of pederin. Small amounts of pederin found in males and (−)-females are due to pederin transfer from (+)-females to the offspring. b, Agarose gel of the PCR products obtained from total DNA of the same beetle specimens that were used for pederin extraction. L, 1 kb DNA ladder; B, blind PCR control without template DNA; 1 *Paederus fuscipes*, (+)-female, collected at Jena, Germany; 2 *P. fuscipes*, (−)-female, Jena; *P. fuscipes*, male, Jena; 4, *P. fuscipes*, (+)-female, collected at Aydin, Turkey; 5, *P. fuscipes*, (−)-female, Aydin; 6, *P. fuscipes*, male, Aydin; 7, *Paederidus rubrothracicus*, (+)-female, Aydin; 8, *Pd. rubrothracicus*, (−)-female, Aydin; 9, *Pd. rubrothracicus*, male, Aydin; 10, *Paederus litoralis*, (+)-female, Jena; 11, *P. litoralis*, male, Jena. No (−)-female of *P. litoralis* was available.

FIG. 3 is a map of the sequenced ped genes and the proposed pederin biosynthesis pathway. MT, methyltransferase, OR, oxidoreductase, AT, acyltransferase; KS, ketosynthase domain; ACP, acyl carrier protein domain; KR, ketoreductase domain; DH, dehydratase domain; (DH), putative nonfunctional dehydratase domain, OXY, oxygenase; C, nonribosomal peptide synthetase condensation domain; A, nonribosomal peptide synthetase adenylation domain; T, nonribosomal peptide synthetase thiolation domain, TE, thioesterase domain.

Figure 4:
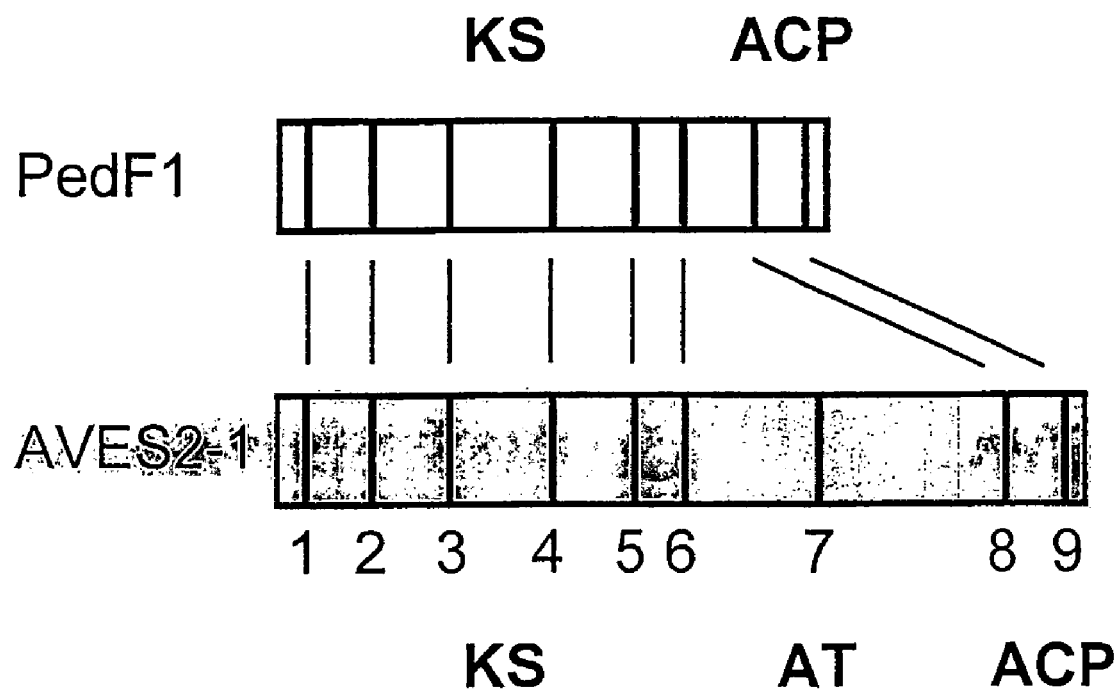

FIG. 4 shows a comparison of the first modules of PedF and the first module of the avermectin AVES2 protein which is a regular type I polyketide synthase. The shaded area in AVES2-1 indicates the AT region that is deleted in PedF1. Conserved motifs are shown as vertical bars. Motifs are: 1, EPIAIV SEQ ID NO: 20; 2, DPQQRL SEQ ID NO: 21; 3, CSSS SEQ ID NO: 22; 4, HGTGTXLGD SEQ ID NO: 23; 5, GxGGxNAHVILEE SEQ ID NO: 24; 6, YTL; 7, GHSxG SEQ ID NO: 25; 8, YPF; 9, GxDS SEQ ID NO: 26.

The sequences mentioned in this application are listed in the attached sequence listing. These sequences are shortly summarized in the following:

SEQ ID NO:1: nucleic acid sequence of the pederin biosynthetic gene cluster

SEQ ID NO:2: protein sequence of PedA putative methytransferase

SEQ ID NO:3: protein sequence of PedB putative FMN-dependent oxidoreductase

SEQ ID NO:4: protein sequence of PedC putative acetyltransferase

SEQ ID NO:5: protein sequence of PedD putative acetyltransferase

SEQ ID NO:6: protein sequence of PedE putative methyltransferase

SEQ ID NO:7: protein sequence of PedF mixed type I polyketide synthase/nonribosomal peptide synthase (module 1 PKS (KS-ACP), module 2 NRPS (C-A-T), module 3 PKS (KS-KR-ACP), module 4 PKS (KS-KR-MT-ACP), module 5 PKS (KS-KR-DH-DH-ACP), module 6 PKS (KS-KR-ACP), module 7 incomplete PKS (KS-DH))

SEQ ID NO:8: protein sequence of PedG putative flavin-binding monooxygenase

SEQ ID NO:9: protein sequence of PedH mixed type I polyketide synthase/nonribosomal peptide synthase (module 1 incomplete PKS (ACP), module 2 PKS (KS-DH-KR-ACP), KS-DH-ACP), module 3 PKS (KS-DH-ACP), module 4 PKS (KS-KR-ACP), module-5 PKS (KS-ACP), module 6 NRPS (C-A-T-TE))

SEQ ID ND:10 and SEQ ID NO:11: nucleic acid sequences of degenerate primers used during the cloning of the ped genes SEQ ID NO:12 to SEQ ID NO:19: nucleic acid sequences of primers used during the cloning of the ped genes The present invention will now be described in further detail with reference to a particular example.

According to the example of the present invention, pederin biosynthesis genes were cloned from total DNA of *Paederus fuscipes* beetles, which use this compound for chemical defense. Sequence analysis of the gene cluster and adjacent regions revealed the presence of open reading frames with typical bacterial architecture and homologies. The cluster is present only in female beetles with high pederin content and encodes a mixed modular polyketide synthase—nonribosomal peptide synthetase. Notably, none of the modules contains regions with homology to acyltransferase domains, but two copies of isolated monodomain acyltransferase genes were found at the upstream end of the cluster. This architecture suggests a novel mechanism of extender unit selection, distinct from previously described modular polyketide systems. The cluster represents the first example of cloned genes from an unculturable invertebrate symbiont that encodes the biosynthesis of a potential drug candidate.

To clone the pederin cluster, a PCR strategy was pursued involving degenerate primers based on universally conserved motifs of KS domains. Total DNA, isolated from different beetle specimens, was used as a PCR template. Analysis of three species of the genera *Paederus* and *Paederidus* collected at two different locations consistently revealed that only those adult beetles with a high pederin content gave the PCR product expected to arise from the presence of PKS genes (FIG. 2). Amplification products were also obtained by using eggs from (+)-females of a fourth species, *P. riparius*, from a third locality (data not shown). Sequencing of the amplified DNA showed, in all cases, the exclusive presence of the same group of three to four different sequences possessing strong homology to KS domains of bacterial type I PKSs. This is shown in the following Table 1.

TABLE 1

Comparison of DNA sequences obtained by PCR from different beetle specimens.

| Sequence name | P. fuscipes adults (Jena, Germany) | P. fuscipes adults (Aydin, Turkey) | P. litoralis adults (Jena, Germany) | P. riparius eggs (Bayreuth, Germany) | Paederidus rubrothoracicus (Aydin, Turkey) | Highest homology |
|---|---|---|---|---|---|---|
| PKS1 | + | + | + | + | + | B. subtilis Pks (54%) |
| PKS2 | + | + | + | + | + | B. subtilis Pks (67%) |
| PKS3 | + | + | + | − | + | B. subtilis Pks (53%) |
| PKS4 | + | − | − | + | + | B. subtilis Pks (44%) |

Note:
+ and − indicate present and absent sequences, respectively.

The perfect correlation between pederin content and PKS sequences, independent of species and locality of collection, suggests that the amplified fragments belong to different modules of the pederin cluster. These DNA fragments were therefore used to locate the cluster.

To this end, a metagenomic cosmid library was constructed from total DNA of P. fuscipes beetles. By screening this library with specific PCR primers derived from the amplified sequences (see Methods below), three positive cosmids were identified. Sequencing of a 52.7 kb region revealed the presence of ORFs homologous to type I PKS genes, designated as ped genes. All of the ampylified KS sequences could be found on these ORFs. Additional regions covering ca. 60 kb outside of the cluster were obtained on two cosmids isolated by chromosome walking and subjected to extensive spot sequencing. All putative genes present on these cosmids exhibit typical bacterial features: they are tightly packed, free of introns and polyadenylation sites, and preceded by Shine-Dalgarno patterns in appropriate distances to the start codons. Furthermore, when subjected to database homology searches, each of the translated ORFs exhibited the highest similarity to bacterial proteins. Among the homologies to 65 different ORFs analysed, 15 are exclusively known from prokaryotes, such as enzymes used in vitamin $B_{12}$ biosynthesis, type II fatty acid synthase components and regulatory proteins of the LuxR and LysR families. From these findings the inventor concluded that the ped cluster is located on a bacterial genome.

FIG. 3 summarizes the results from an analysis of the completely sequenced 52.7 kb region. The predicted gene products of the ORFs pedF and pedH are giant proteins of 8601 and 6266 amino acids (aa), respectively, resembling mixed modular PKSs/nonribosomal peptide synthetases (NRPSs). Strikingly, AT homologies are completely absent on these proteins. Alignment with other known type I PKSs revealed that a continuous ~300 aa region of each AT domain, including the active site GHS motif, are deleted in pedF and pedH, with no other homologies replacing them (FIG. 4), which leads to a considerable shortening of each module. In modular PKSs, the AT domain is crucial in the selection of the correct acyl-CoA unit in each extension cycle, raising the interesting question how this process is controlled during assembly of pederin from two different acyl-CoA units. The ORFs pedC and pedD, located upstream of pedF and encoding deduced proteins with homology to monodomain ATs, could play a possible role in selectivity control. It is tempting to speculate that each of these isolated ATs recognises a different extension unit and is bound and used iteratively by cognate PKS modules. The ped cluster would then encode a type I protein complemented by repetitive type II enzymes. Intriguingly, a similar PKS system containing such putative "super ATs" is encoded on the genome of Bacillus subtilis. The gene products of the pks cluster consist of a large number of PKS modules without AT domains and, encoded at the upstream end of the cluster, three isolated ATs. The secondary metabolite generated by these proteins is not known. Sequence comparison with other known PKS clusters reveals that the ped and the B. subtilis pks clusters are more closely related to each other than to any other known PKS cluster. The two clusters could therefore belong to a phylogenetically distinct subgroup of functionally novel type I PKS systems.

With few exceptions, the order of encoded modules in type I PKS clusters strictly correlates with the sequence of biosynthetic steps. In most cases the core structure of the metabolite can therefore be predicted from the gene architecture and vice versa. Except for the missing first three modules, which could not be found in the sequenced region, the pederin structure is perfectly mirrored in pedF (FIG. 3). The single ORF should thus be responsible for the formation of the largest part of the pederin molecule except for the six-membered ring bearing the exomethylene group. Characteristic features of the cluster include (i) O-methyltransferase and oxygenase tailoring genes upstream and downstream of pedF, most likely involved in the final biosynthetic steps, (ii) a rare methyltransferase domain in PedF that should catalyse the formation of the uncommon geminal dimethyl group, as known from epothilone biosynthesis, (iii) a repeated dehydratase domain in PedF that putatively performs a sequential elimination of water and intramolecular alcohol attack to generate the dimethylated tetrahydropyrane ring and (iv) a NRPS module in PedF that likely incorporates an amino acid to account for the amide bond. Previous studies have identified sequence patterns of NRPS activating domains that can be used to predict the amino acid incorporated by the corresponding module. The structure of pederin suggests that glycine is selected by the NRPS module of PedF. In accordance, a pattern analysis of the PedF NRPS module revealed 100% identity to the known consensus nonribosomal code for glycine.

Analysis of the modular architecture of the pederin cluster as shown in FIG. 3 further suggests that the biosynthesis of pederin proceeds via a larger intermediate that is cleaved oxidatively into two fragments. One of these fragments would be converted by further biosynthetic steps to pederin. The intermediate presumably is very similar to the longer-chain compounds derived from sponges like onnamide and icadamide B. Manipulation of the pederin cluster (e.g. by inactivating the cleaving oxygenase gene) should therefore also enable access to analogues of these marine drugs.

Taken together, these findings and the fact that the ped genes contained all of the amplified KS fragments and only occur in beetles with high pederin content, independent of species and geography, are compelling evidence that the cloned gene cluster indeed encodes pederin biosynthesis.

The present invention showed for the first time that genes responsible for the biosynthesis of rare invertebrate drug candidates can be cloned from unculturable bacterial symbionts. Since whole sets of type I PKS genes have been functionally expressed even in E. coli, a similar production of "invertebrate" natural products in a suitable host has now become a realistic scenario. The novel structure of the ped cluster, featuring small-sized modules and ATs with putatively high catalytic flexibility, furthermore offers fascinating possibilities for generating unnatural drug analogues by combinatorial biosynthesis.

Methods.

Pederin analysis. Beetle species were determined by R. 5L. L. Kellner and H. Baspinar. Beetles were stored individually in ethanol immediately after collection to preserve the DNA. For pederin analysis the ethanol was concentrated to 50 µl, and 10 µl were spotted on a silica gel TLC plate (Merck). The plate was then developed in ethyl acetate and stained with anisaldehyde reagent. A pink spot at $R_F$=0.22 was specific for pederin.

Cloning of the ped genes. A QIAAMP DNA™ mini kit (Qiagen) was used to extract DNA from adult beetles with known pederin content. This DNA was used as PCR template. For egg DNA templates, one egg was ground in PCR buffer at ° C. using a Wheaton homogenizer (previously treated with concentrated HCl for 15 min and washed with sterile $H_2O$), transferred into a PCR tube, frozen and thawed three times and subsequently boiled for 5 min, then the remaining PCR components were added. For all initial reactions, the primers KSDPQQF (5'-MGNGARGCNNWNSMNATGGAYC CNCARCANMG-3') (SEQ ID NO:10) and KSHGTGR (5'-GGRTCNCCNARNSWN GTNCCNGTNCC-RTG-3') (SEQ ID NO:11) and Platinum Taq DNA Polymerase-High Fidelity (Invitrogen) were used (M=A+C, R=A+G, W=A+T, S=C+G, Y=C+T, N=A+T+C+G). Each PCR experiment was performed at least in triplicate except for the rarer P. litoralis adults, where only two reactions could be run for each sex. PCR products were ligated into the pGEM-T Easy vector (Promega) and digested with RsaI. Plasmids showing a unique restriction pattern were sequenced using the BigDye Terminator Ready Mix (Applied Biosystems) and an ABI 3700 sequencer (Applied Biosystems). From these sequences the following primer pairs specific for single modules were designed: 5'-TGGCATCGT GGGGAAAGGCTG-3' (SEQ ID NO:12)-5'-GGCGCAGGTGCTGACACGC-3' (SEQ ID NO:13) (KSLF-KSlR), 5'-TTAGCCATCGAGAGTTA-CAGCTC-3' (SEQ ID NO:14)-5'-AATCGCCGATAGC-CATCGCCG-3' (SEQ ID NO:15) (KS2F-KS2R), 5'-GACGCCATGGATGCACTGCAC-3' (SEQ ID NO:16)-5'-TATTGGATGCTCAG CACCGCAC-3' (SEQ ID NO:17) (KS3F-KS3R) and 5'-GGGCTCAGTTTCCACC CTTATG-3' (SEQ ID NO:18)-5'-CCGGCGCTGCAGAGCCAGG-3' (SEQ ID NO:19) (KS4F-KS4R). As cosmid library was prepared from total DNA of 10 P. fuscipes (+)-females collected in Aydin, Turkey, using the pWEB cosmid cloning kit (Epicentre). The library was plated at concentrations to yield about 300 colonies per plate. The bacteria from each plate were combined, and the complete plasmid DNA isolated from 12 plate pools was screened by diagnostic PCR using the specific primers. Positive pools were plated at numbers of 50 per plate and rescreened. This procedure was repeated until single positive colonies could be identified. Positive cosmids were sonicated, end-repaired by BAL-31 and Klenow fragment and size-fractionated by gel electrophoresis to yield fragments of 1-2 kb lengths. These fragments were ligated into the EcoRV site of pBluescript II K (Stratagene) and end sequenced. Remaining gaps were filled by using specifically designed primers and by targeted subcloning. Sequence analysis was performed by using BLASTX, PROSITE, FRAMEPLOT and the Lasergene DNASTAR software package.

The invention claimed is:

1. An isolated nucleic acid comprising a pederin biosynthetic gene cluster or being fully complementary to a sequence comprising a pederin biosynthetic gene cluster, comprising a pedF nucleotide sequence, wherein the pedF nucleotide sequence is selected from the group consisting of nucleotides 6309-32114 of SEQ ID NO: 1 and fully complementary sequence of nucleotides 6309-32114 of SEQ ID NO: 1.

2. The isolated nucleic acid according to claim 1 which is derived from a bacterial symbiont of *Paederus* or *Paederidus* rove beetles.

3. The isolated nucleic acid according to claim 1, wherein the pedF encodes a protein sequence as shown in SEQ ID NO:7.

4. The isolated nucleic acid according to claim 1, comprising a nucleotide sequence selected from the group consisting of SEQ ID NO:1, and a fully complementary nucleotide sequence, wherein the complementary nucleotide sequence is the complement of SEQ ID NO:1.

5. A vector comprising the nucleic acid comprising the pederin biosynthetic gene cluster of claim 1.

6. A vector comprising the nucleic acid according to claim 1.

7. A recombinant host cell or a transgenic organism comprising the nucleic acid according to claim 1.

8. A recombinant host cell according to claim 7 which is a bacterial cell.

9. A method for producing pederin using a recombinant host cell or a transgenic organism according to claim 7 comprising the steps of: culturing the recombinant host cell or the transgenic organism under conditions to express the pederin biosynthetic gene cluster; and isolating the produced pederin.

10. The recombinant host cell according to claim 8 wherein the bacterial cell is a *Pseudomonas, Acinetobacter, Bacillus* or *Streptomyces* cell.

* * * * *